United States Patent
Brewster et al.

(10) Patent No.: US 8,268,843 B2
(45) Date of Patent: Sep. 18, 2012

(54) 5,8-DIFLUORO-4-(2-(4-(HETEROARYLOXY)-PHENYL)ETHYLAMINO)QUINAZOLINES AND THEIR USE AS AGROCHEMICALS

(75) Inventors: William K. Brewster, Indianapolis, IN (US); Carla J. R. Klittich, Zionsville, IN (US); Chenglin Yao, Westfield, IN (US); Yuanming Zhu, Carmel, IN (US); Brent J. Rieder, Greenfield, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 146 days.

(21) Appl. No.: 12/550,952

(22) Filed: Aug. 31, 2009

(65) Prior Publication Data
US 2010/0056374 A1 Mar. 4, 2010

Related U.S. Application Data

(60) Provisional application No. 61/092,968, filed on Aug. 29, 2008.

(51) Int. Cl.
*A61K 31/517* (2006.01)

(52) U.S. Cl. .................. 514/266.3; 514/266.4; 544/287; 544/293

(58) Field of Classification Search .................. 544/287, 544/293
See application file for complete search history.

(56) References Cited

U.S. PATENT DOCUMENTS

| 3,470,182 A | 9/1969 | Hardtmann | |
| 7,063,856 B2 * | 6/2006 | Ducray et al. | 424/405 |

FOREIGN PATENT DOCUMENTS

| EP | 0326328 A2 | 8/1989 |
| GB | 2036025 | 6/1980 |
| WO | WO93/04583 | 3/1993 |
| WO | WO94/04526 A | 3/1994 |
| WO | WO94/04527 A2 | 3/1994 |
| WO | WO97/38979 A | 10/1997 |
| WO | WO 97-38979 A | 10/1997 |

* cited by examiner

*Primary Examiner* — James O Wilson
*Assistant Examiner* — Brian McDowell
(74) *Attorney, Agent, or Firm* — Charles W. Arnett; Faegre Baker Daniels LLP

(57) ABSTRACT

The present disclosure relates to 5,8-difluoro-4-(2-(4-(heteroaryloxy)-phenyl)ethylamino)quinazolines and their use as agrochemicals and animal health products.

2 Claims, No Drawings

5,8-DIFLUORO-4-(2-(4-(HETEROARYLOXY)-PHENYL)ETHYLAMINO)QUINAZOLINES AND THEIR USE AS AGROCHEMICALS

CROSS REFERENCE TO RELATED APPLICATIONS

This application claims the benefit of U.S. Provisional Patent Application Ser. No. 61/092,968 filed Aug. 29, 2008.

FIELD OF THE INVENTION

The present disclosure relates to 5,8-difluoro-4-(2-(4-(heteroaryloxy)-phenyl)ethylamino)quinazolines and their use as agrochemicals and animal health products.

BACKGROUND AND SUMMARY

The present disclosure provides novel organic compounds that may demonstrate control of fungi, insects, mites, and animal parasites. The disclosure also provides novel pesticide methods and compositions utilizing the novel compounds.

More specifically, the invention provides new compounds of the formula (I):

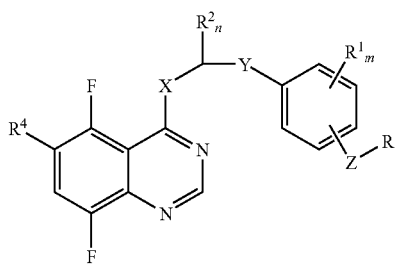

wherein:

R represents H, CH$_3$, or a heterocycle selected from the group consisting of pyridinyl, pyrazinyl, pyrimidinyl, or pyridazinyl wherein the heterocycle may be optionally substituted with one or more groups selected from halo, lower alkyl, lower alkenyl, lower alkynyl, lower alkoxy, haloalkyl, haloalkoxy, NO$_2$, CN, lower alkoxycarbonyl, and lower alkyl-SO$_q$, when q is an integer from 0 to 2;

Z represents a C-C single bond, CH$_2$, NH, O, S, —CH$_2$O—, or —OCH$_2$—;

m is 4;

R$^1$ are independently H, halo, lower alkyl, lower alkenyl, lower alkynyl, hydroxy, lower alkoxy, haloalkyl, haloalkoxy, NO$_2$, CN, lower alkoxycarbonyl, mercapto, or lower alkylthio;

Y is a C-C single bond, C(R$^7_n$)O or C(R$^7_n$);

n is 2;

R$^2$ are independently H or lower alkyl

R$^7$ are independently H or lower alkyl;

X is NR$^3$ or O, where R$^3$ is selected from H, lower alkyl, lower alkyl-carbonyl, lower alkoxycarbonyl, hydroxy, lower alkoxy, lower alkyl-SO$_q$, phenyl-SO$_q$ or substituted phenyl-SO$_q$ when q is an integer from 0 to 2; and R$^4$ is H or F;

with the proviso that when Y is C(R$^7_n$), R$^2_n$ and one of R$^1$ may be taken together to form a compound of formula (I-C)

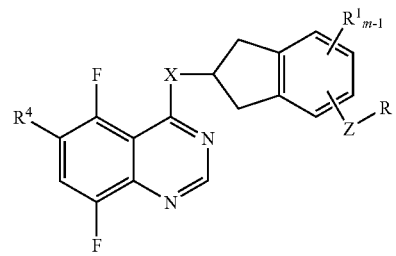

The invention also provides new pesticide methods and compositions utilizing the compounds of formula (I).

The invention includes fungicidal, insecticidal, acaricidal, and anti-parasitic compositions comprising an effective amount of a compound of the present invention in a mixture with an agriculturally acceptable or pharmaceutically acceptable adjuvant or carrier. The invention also includes methods of controlling a fungus, insect, mite, or parasite comprising applying an effective amount of a compound of the present invention to the fungus, insect or mite, soil, plant, root, foliage, seed, locus, or animal (for which purpose they may be administered orally, parenterally, percutaneously or topically) in which the infestation is to be prevented or cured.

DETAILED DESCRIPTION OF THE INVENTION

The compounds of the present invention are directed to compounds of formula (I)

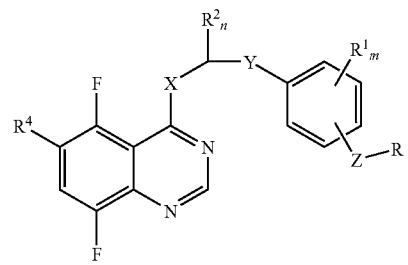

wherein R may be an optionally substituted six-membered heterocyclic system containing one or two nitrogen atoms. More specifically, R may be selected from:

optionally substituted pyridinyl

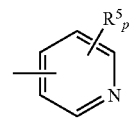

optionally substituted pyrazinyl

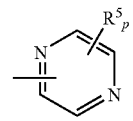

optionally substituted pyrimidinyl

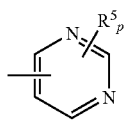

optionally substituted pyridazinyl

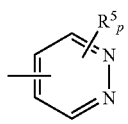

where p is 4 in the case of pyridinyl and 3 in the case of pyrazinyl, pyrimidinyl, and pyridazinyl, and $R^5$ are independently H, halo, lower alkyl, lower alkoxy, lower alkenyl, lower alkynyl, haloalkyl, haloalkoxy, $NO_2$, CN, lower alkoxycarbonyl and lower alkyl-$SO_q$ and q is an integer from 0 to 2.

Throughout this document, all temperatures are given in degrees Celsius, and all percentages are weight percentages unless otherwise stated.

The terms "alkyl", "alkenyl" and "alkynyl", as well as derivative terms such as "alkoxy" and "alkylthio", as used herein, include within their scope straight chain, branched chain and cyclic moieties. The terms "alkenyl" and "alkynyl" are intended to include one or more unsaturated bonds.

The term "halo" refers to F, Cl, Br, and I atoms.

The term "lower alkyl" refers to $C_1$ to $C_6$ straight hydrocarbon chains and $C_3$ to $C_6$ branched and cyclic hydrocarbon groups.

The terms "lower alkenyl" and "lower alkynyl" refer to $C_2$ to $C_6$ straight hydrocarbon chains and $C_3$ (or $C_4$ in the case of lower alkynyl) to $C_6$ branched hydrocarbon groups containing at least one unsaturated bond.

The terms "lower alkoxy" and "lower alkylthio" refer to O-lower alkyl and S-lower alkyl groups.

The term "haloalkyl" refers to lower alkyl groups substituted with one or more halo atoms.

The term "haloalkoxy" refers to lower alkoxy groups substituted with one or more halo atoms.

The term "substituted phenyl" refers to phenyl substituted with lower alkyl, lower alkenyl, lower alkynyl, lower alkoxy, lower alkylthio, halo, hydroxy, $NO_2$, haloalkyl, haloalkoxy, haloalkylthio, CN, phenyl, substituted phenyl, O-phenyl, O-substituted phenyl, $C_1$-$C_4$ alkanoyloxy, $C_1$-$C_4$ alkoxycarbonyl, benzyloxy, or and lower alkyl-$SO_q$ and q is an integer from 0 to 2.

In the present invention, whenever multiple substituents are independently selected it is to be understood that they are selected so as to be sterically compatible with each other. Steric compatibility refers to the absence of steric hindrance as this term is defined in The Condensed Chemical Dictionary, 7th edition, Reinhold Publishing Co., N.Y. page 893 (1966), which definition is as follows:

steric hindrance. A characteristic of molecular structure in which the molecules have a spatial arrangement of their atoms such that a given reaction with another molecule is prevented or retarded in rate.

Steric compatibility is characterized by substituents whose physical bulk does not require confinement within volumes insufficient for the exercise of their normal behavior as discussed in D. J. Cram and G. Hammond, Organic Chemistry 2nd edition, McGraw-Hill Book Company, N.Y. page 215 (1964).

The compounds of this invention are made using well known chemical procedures. The required starting materials are commercially available or are readily synthesized using standard procedures.

Synthesis of Compounds (I) Wherein X is O

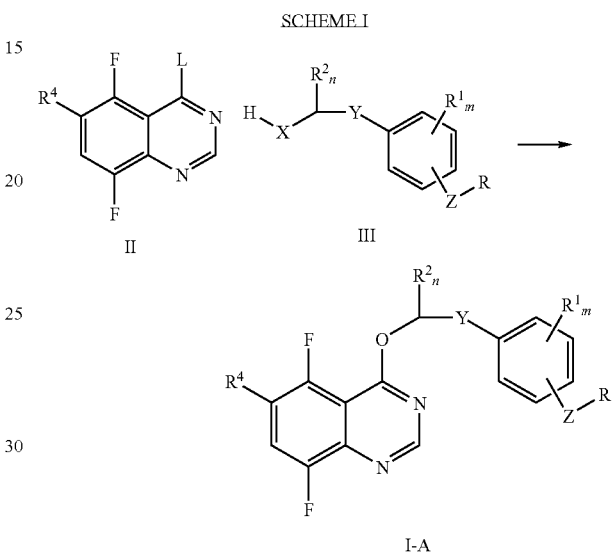

SCHEME I

The compounds of formula (I) wherein X is O (I-A) can be made by condensing a compound of formula (II)

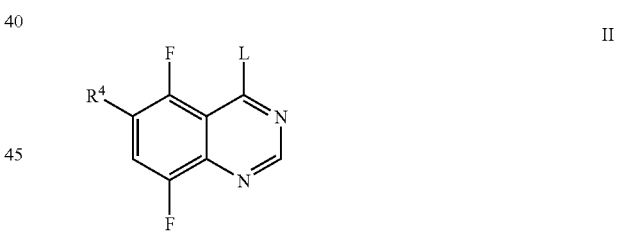

where $R^4$ is as defined as for formula (I); and L is a leaving group, such as F, Cl, Br, I, $NO_2$, 1,2,3-triazol-1-yl, 1,2,4-triazol-1-yl, $OSiMe_3$, arylthio, alkylthio, alkylsulfonyl, arylsulfonyl, alkoxy, alkylsulfinyl, or arylsulfinyl; with a compound of the formula (III)

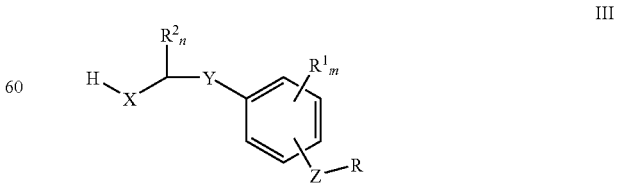

where R, Y, Z, $R^1$, $R^2$, m and n are as defined for formula (I) and X is O. The reaction is preferably carried out in the presence of a base in a non-reactive solvent, such as dichloromethane, THF or DMF, at a temperature in the range of 0° to reflux temperature.

Synthesis of Compounds (I) Wherein X is NH or N-Lower Alkyl

SCHEME II

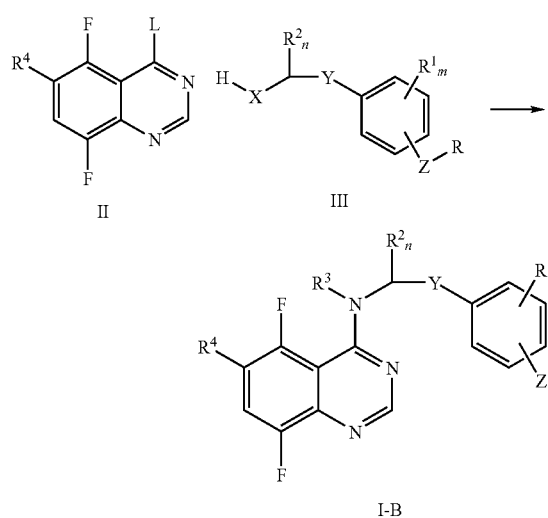

The compounds of formula (I) wherein X is NH or N-lower alkyl and Z is oxygen (I-B), can be made by condensing a compound of formula (II)

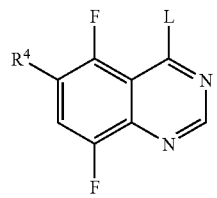

where $R^4$ is as defined as for formula (I); and L is a leaving group, such as F, Cl, Br, I, $NO_2$, 1,2,3-triazol-1-yl, 1,2,4-triazol-1-yl, $OSiMe_3$, arylthio, alkylthio, alkylsulfonyl, arylsulfonyl, alkoxy, alkylsulfinyl, or arylsulfinyl; with a compound of the formula (III)

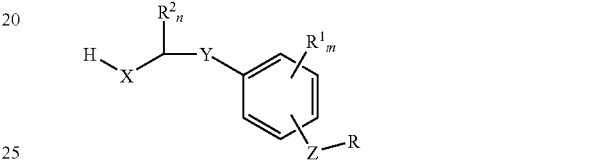

where R, Y, Z, $R^1$, $R^2$, m and n are as defined for formula (I) and X is NH or N-lower alkyl optionally as a salt (e.g., HCl). The reaction is preferably carried out in the presence of base, such as triethylamine, in a non-reactive solvent, such as dichloromethane, THF or DMF.

SCHEME III

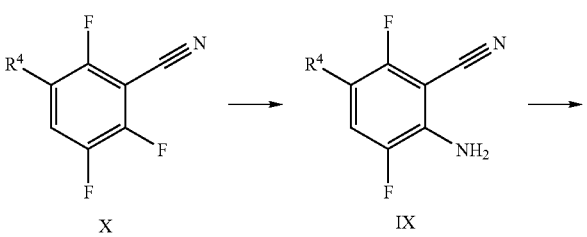

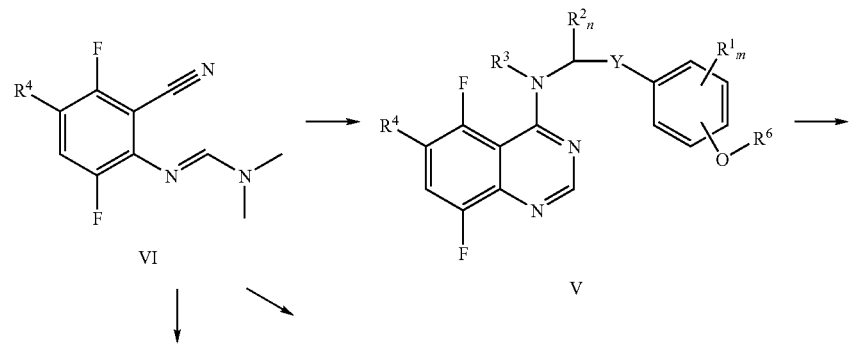

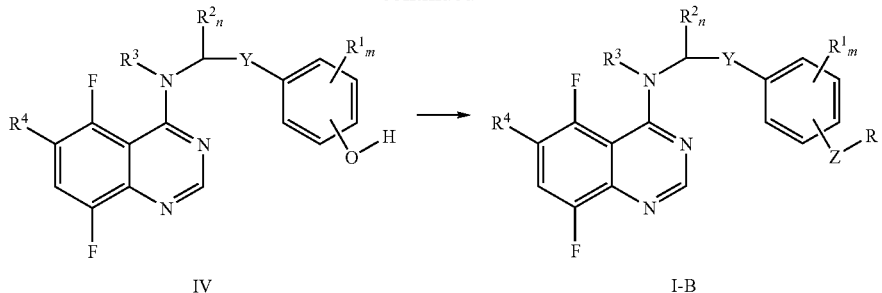

The compounds of formula (I) wherein X is NH or N-lower alkyl and Z is oxygen (I-B) where R is a heterocycle selected from the group consisting of pyridinyl, pyrazinyl, pyrimidinyl, or pyridazinyl wherein the heterocycle may be optionally substituted with one or more groups selected from halo, lower alkyl, lower alkenyl, lower alkynyl, lower alkoxy, haloalkyl, haloalkoxy, $NO_2$, CN, lower alkoxycarbonyl, and lower alkyl-$SO_q$, when q is an integer from 0 to 2;

alternatively are prepared by treatment of a compound of formula (IV)

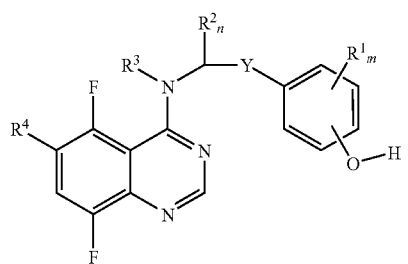

wherein $R^1$, $R^2$, $R^3$, $R^4$, Y, m and n are as defined for formula (I); with a heterocycle of formula L-Het where L is as defined for formula (II) and Het is a heterocycle selected from the group consisting of pyridinyl, pyrazinyl, pyrimidinyl, or pyridazinyl wherein the heterocycle may be optionally substituted with one or more groups selected from halo, lower alkyl, lower alkenyl, lower alkynyl, lower alkoxy, haloalkyl, haloalkoxy, $NO_2$, CN, lower alkoxycarbonyl, and lower alkyl-$SO_q$, when q is an integer from 0 to 2.

The reaction is preferably carried out in the presence of a base, such as sodium hydride, in a nonreactive solvent, such as DMF.

Certain compounds (I) are prepared by modifications of other compounds (I), as described in the Examples shown in the following section.

The compounds of formula (IV) may be prepared by treatment of compounds of formula (V)

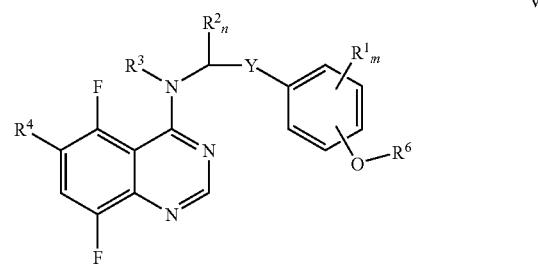

where $R^1$, $R^2$, $R^3$, $R^4$, Y, m and n are as defined for formula (I), and $R^6$ is lower alkyl; with a reagent such as $BBr_3$ in a non-reactive organic solvent, such as dichloromethane.

The compounds of formula (IV) alternatively may be prepared by treatment of compounds of formula (VI) wherein $R^4$ is as described for compound (I),

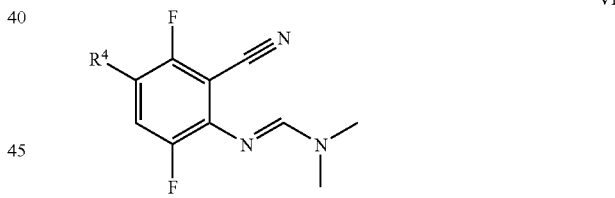

with a compound of formula (VII), optionally as a salt (e.g., HCl),

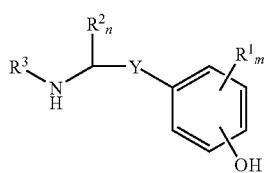

where $R^1$, $R^2$, Y, m and n are as defined for formula (I), and $R^3$ is H; in the presence of acetic acid, optionally as a solution in an appropriate solvent such as ethanol; with heating at temperatures from 25° to reflux.-

The compounds of formula (IV) alternatively may be prepared by treatment of compounds of formula (II)

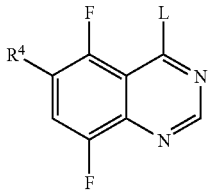

where $R^4$ is as defined as for formula (I); and L is a leaving group, such as F, Cl, Br, I, $NO_2$, 1,2,3-triazol-1-yl, 1,2,4-triazol-1-yl, $OSiMe_3$, arylthio, alkylthio, alkylsulfonyl, arylsulfonyl, alkoxy, alkylsulfinyl or arylsulfinyl; with a compound of formula (VII), optionally as a salt (e.g., HCl),

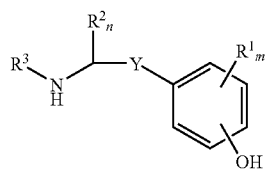

where $R^1$, $R^2$, $R^3$, Y, m and n are as defined for formula (I); optionally in the presence of a base, in a solvent such as acetonitrile, THF or DMF.

Compounds of formula (V) are prepared by the treatment of compounds of formula (VI) wherein $R^4$ is as described for compound (I); with a compound of formula (VIII), optionally as a salt (e.g., HCl),

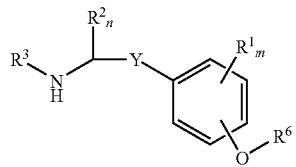

where $R^1$, $R^2$, Y, m and n are as defined for formula (I), $R^3$ is H, and $R^6$ is lower alkyl as defined for formula (I); in the presence of acetic acid, optionally as a solution in an appropriate solvent such as ethanol; with heating at temperatures from 25° to reflux.

Amines of formula (VIII) where $R^1$, $R^2$, $R^3$, Y, m and n are as defined for formula (I) and $R^6$ is lower alkyl as defined for formula (I); are commercially available or may be prepared by well-known methods. For example, compounds of formula (VIII), where $R^1$, $R^2$, m and n are as defined for formula (I), $R^6$ is lower alkyl, $R^3$ is H, and Y is $R^7{}_n$ are prepared as their hydrochloride salts by treatment of appropriately substituted (4-alkoxyphenyl)-acetonitriles with hydrogen in the presence of hydrochloric acid, a catalyst such as palladium on carbon, and an appropriate solvent such as ethanol.

Alternatively, compounds of formula (VIII), where $R^1$, $R^2$, m and n are as defined for formula (I), $R^6$ is lower alkyl, $R^3$ is H, Y is $R^7{}_n$ are prepared by treatment of appropriately substituted (4-alkoxyphenyl)-acetonitriles with borane-dimethyl sulfide complex in an appropriate solvent such as tetrahydrofuran at temperatures from 20° C. to reflux.

Alternatively, compounds of formula (VIII), where $R^1$, $R^2$, m and n are as defined for formula (I), $R^6$ is lower alkyl, $R^3$ is H, and Y is $R^7{}_n$ are prepared as their hydrochloride salts by treatment of appropriately substituted 1-alkoxy-4-((E)-2-nitrovinyl)-benzenes with hydrogen in the presence of hydrochloric acid, a catalyst such as palladium on carbon, and an appropriate solvent such as ethanol.

Alternatively, compounds of formula (VIII), where $R^1$, $R^2$, m and n are as defined for formula (I), $R^6$ is alkyl or benzyl, $R^3$ is H, and Y is $R^7{}_n$ are prepared by treatment of the appropriately substituted 1-alkoxy-4-((E)-2-nitrovinyl)-benzenes with lithium aluminum hydride in an appropriate solvent such as tetrahydrofuran.

The 1-alkoxy-4-((E)-2-nitrovinyl)-benzenes are prepared by treatment of the appropriately substituted benzaldehyde with nitromethane in the presence of ammonium acetate.

The compounds of formula (I) wherein X is NH (namely, formula I-B where $R^3$ is H) alternatively are prepared by treatment of a compound of formula (VI), as defined above, with a compound of formula (III), optionally as a salt (e.g., HCl), where R, Z, $R^1$, $R^2$, m and n are as defined for formula (I) and X is NH; in the presence of acetic acid, optionally as a solution in an appropriate solvent such as ethanol; with heating at temperatures from 25° to reflux.

Compounds of formula (VI)

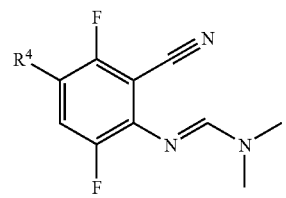

where $R^4$ is as described for compound (I) were prepared by treatment of a compound of formula (IX)

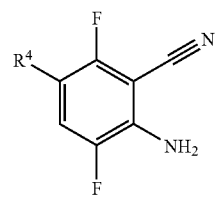

where $R^4$ is as defined for (I), with N,N-dimethylformamide dimethyl acetal in an appropriate solvent such as toluene, with heating at temperature from 25° C. up to the reflux temperature.

Compounds of formula (IX)

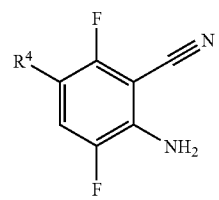

where R⁴ is as defined for (I) were prepared by treatment of compounds of formula (X)

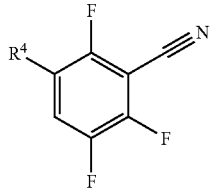

where R⁴ is as defined for (I), with ammonium hydroxide solution at a temperature of 25 to 100°.

The compounds of the present invention may have fungitoxic activity against harmful fungi including, but not limited to, fungi that are pathogens of plants, animals, and humans. They are active against fungi of a number of classes including Oomycetes, Deuteromycetes (Fungi Imperfecti), Basidiomycetes, and Ascomycetes. More particularly, one embodiment of a method of the present invention provides for activity against phytopathogenic organisms including, but not limited to, *Pyricularia oryzae, Colletotrichum* species, *Eysiphe* species, *Puccinia* species, *Helminthosporium* species, *Alternaria* species, *Septoria* species, *Rhynchosporium secalis, Cercospora* and *Cercosporella* species, and *Pyrenophora* species. Additional diseases controlled include powdery mildews incited by *Sphaerotheca fulignea* (cucurbit powdery mildew) and *Uncinula necator* (grape powdery mildew), soybean rust incited by *Phakopsora pachyrhizi*, downy mildews such as cucumber downy mildew (*Pseudoperonospora cubensis*), grape downy mildew (*Plasmopara viticola*), apple scab incited by *Venturia inaequalis*, and late blight incited by *Phytophthora infestans*.

The compounds of the present invention may have insecticidal activity against harmful insects and mites including, but not limited to, insects that are pests or parasites of plants, animals, and humans.

In other embodiments, the invention disclosed in this document may be used to control pests of Phylum Nematoda, the Phylum Arthropoda, the Subphylum Chelicerata, the Class Arachnida, the Subphylum Myriapoda, the Class Symphyla, the Subphylum Hexapoda, the Class Insecta, and Coleoptera (beetles). A non-exhaustive list of these such pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turgrass Ataenius), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp, *Cerotoma* spp. (chrysomeids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae, Hylobius pales* (pales weevil), *Hypera* spp. (weevils), *Hypera postica* (alfalfa weevil), *Hyperodes* spp. (*Hyperodes weevil*), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In another embodiment, the invention disclosed in this document may be used to control Dermaptera (earwigs).

In another embodiment, the invention disclosed in this document may be used to control Dictyoptera (cockroaches). A non-exhaustive list of such pests includes, but is not limited to, *Blattella germanica* (German cockroach), *Blatta orientalis* (oriental cockroach), *Parcoblatta pennylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In another embodiment, the invention disclosed in this document may be used to control Diptera (true flies). A non-exhaustive list of such pests includes, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranea fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumna-* lis (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document may be used to control Hemiptera (true bugs). A non-exhaustive list of such pests includes, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildingi, Poecilocapsus lineatus* (fourlined plant bug), *Psallus vaccinicola, Pseudacysta perseae, Scaptocoris castanea*, and *Triatoma* spp. (bloodsucking conenose bugs/kissing bugs).

In another embodiment, the invention disclosed in this document may be used to control Homoptera (aphids, scales, whiteflies, leafhoppers). A non-exhaustive list of such pests includes, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicoruis, Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*.

In another embodiment, the invention disclosed in this document may be used to control Hymenoptera (ants, wasps, and bees). A non-exhaustive list of such pests includes, but is not limited to, *Acromyrrmex* spp., *Athalia rosae, Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document may be used to control Isoptera (termites). A non-exhaustive list of such pests includes, but is not limited to, *Coptotermes* spp., *Coptotermes curvignathus, Coptotermes frenchii, Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus, Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi, Procornitermes* spp., *Reticulitermes* spp. (subterranean termites), *Reticulitermes banyulensis, Reticulitermes grassei, Reticulitermes flavipes* (eastern subterranean termite), *Reticulitermes hageni, Reticulitermes hesperus* (western subterranean termite), *Reticulitermes santonensis, Reticulitermes speratus, Reticulitermes tibialis, Reticulitermes virginicus, Schedorhinotermes* spp., and *Zootermopsis* spp. (rotten-wood termites).

In another embodiment, the invention disclosed in this document may be used to control Lepidoptera (moths and butterflies). A non-exhaustive list of such pests includes, but is not limited to, *Achoea janata, Adoxophyes* spp., *Adoxophyes orana, Agrotis* spp. (cutworms), *Agrotis ipsilon* (black cutworm), *Alabama argillacea* (cotton leafworm), *Amorbia cuneana, Amyelosis transitella* (navel orangeworm), *Anacamptodes defectaria, Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrana* (orange tortrix), *Autographa gamma, Bonagota cranaodes, Borbo cinnara* (rice leaf folder), *Bucculatrix thurberiella* (cotton leafperforator), *Caloptilia* spp. (leaf miners), *Capua reticulana, Carposina niponensis* (peach fruit moth), *Chilo* spp., *Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta, Diaphania* spp. (stem borers), *Diatraea* spp. (stalk borers), *Diatraea saccharalis* (sugarcane borer), *Diatraea graniosella* (southwester corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobacco moth),

*Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis cerasana* (common currant tortrix), *Pandemis heparana* (brown apple tortrix), *Papilio demodocus, Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella, Phyllonorycter* spp. (leafminers), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarpa, Prays oleae* (olive moth), *Pseudaletia* spp. (noctuid moths), *Pseudaletia unipunctata* (armyworm), *Pseudoplusia includens* (soybean looper), *Rachiplusia nu, Scirpophaga incertulas, Sesamia* spp. (stemborers), *Sesamia inferens* (pink rice stem borer), *Sesamia nonagrioides, Setora nitens, Sitotroga cerealella* (Angoumois grain moth), *Sparganothis pilleriana, Spodoptera* spp. (armyworms), *Spodoptera exigua* (beet armyworm), *Spodoptera fugiperda* (fall armyworm), *Spodoptera oridania* (southern armyworm), *Synanthedon* spp. (root borers), *Thecla basilides, Thermisia gemmatalis, Tineola bisselliella* (webbing clothes moth), *Trichoplusia ni* (cabbage looper), *Tuta absoluta, Yponomeuta* spp., *Zeuzera coffeae* (red branch borer), and *Zeuzera pyrina* (leopard moth).

In another embodiment, the invention disclosed in this document may be used to control Mallophaga (chewing lice). A non-exhaustive list of such pests includes, but is not limited to, *Bovicola ovis* (sheep biting louse), *Menacanthus stramineus* (chicken body louse), and *Menopon gallinea* (common hen house).

In another embodiment, the invention disclosed in this document may be used to control Orthoptera (grasshoppers, locusts, and crickets). A non-exhaustive list of such pests includes, but is not limited to, *Anabrus simplex* (Mormon cricket), Gryllotalpidae (mole crickets), *Locusta migratoria, Melanoplus* spp. (grasshoppers), *Microcentrum retinerve* (angularwinged katydid), *Pterophylla* spp. (kaydids), *chistocerca gregaria, Scudderia furcata* (forktailed bush katydid), and *Valanga nigricorni*.

In another embodiment, the invention disclosed in this document may be used to control Phthiraptera (sucking lice). A non-exhaustive list of such pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Phtirus pubis* (crab louse), In another embodiment, the invention disclosed in this document may be used to control Siphonaptera (fleas). A non-exhaustive list of such pests includes, but is not limited to, *Ctenocephalides canis* (dog flea), *Ctenocephalides felis* (cat flea), and *Pulex irritans* (human flea).

In another embodiment, the invention disclosed in this document may be used to control Thysanoptera (thrips). A non-exhaustive list of such pests includes, but is not limited to, *Frankliniella fusca* (tobacco thrips), *Frankliniella occidentalis* (western flower thrips), *Frankliniella shultzei Frankliniella williamsi* (corn thrips), *Heliothrips haemorrhaidalis* (greenhouse thrips), *Riphiphorothrips cruentatus, Scirtothrips* spp., *Scirtothrips citri* (citrus thrips), *Scirtothrips dorsalis* (yellow tea thrips), *Taeniothrips rhopalantennalis*, and *Thrips* spp.

In another embodiment, the invention disclosed in this document may be used to control Thysanura (bristletails). A non-exhaustive list of such pests includes, but is not limited to, *Lepisma* spp. (silverfish) and *Thermobia* spp. (firebrats).

In another embodiment, the invention disclosed in this document may be used to control Acarina (mites and ticks). A non-exhaustive list of such pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (american dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (twospotted spider mite), and *Varroa destructor* (honey bee mite).

In another embodiment, the invention disclosed in this document may be used to control Nematoda (nematodes). A non-exhaustive list of such pests includes, but is not limited to, *Aphelenchoides* spp. (bud and leaf & pine wood nematodes), *Belonolaimus* spp. (sting nematodes), *Criconemella* spp. (ring nematodes), *Dirofilaria immitis* (dog heartwom), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In another embodiment, the invention disclosed in this document may be used to control Symphyla (symphylans). A non-exhaustive list of such pests includes, but is not limited to, *Scutigerella immaculata*.

In another embodiment, the invention disclosed in this document may be used to control animal and human parasites. A non-exhaustive list of such pests includes, but is not limited to, arthropods such as mites (e.g., mesostigmatids, itch, mange, scabies, chiggers), ticks (e.g., soft-bodied and hard-bodied), lice (e.g., sucking, biting), fleas (e.g., dog flea, cat flea, oriental rat flea, human flea), true bugs (e.g., bed bugs, Triatomid bugs), bloodsucking adult flies (e.g., horn fly, horse fly, stable fly, black fly, deer fly, louse fly, tsetse fly, mosquitoes), and parasitic fly maggots (e.g, bot fly, blow fly, screwworm, cattle grub, fleeceworm); helminths such as nematodes (e.g., threadworm, lungworm, hookworm, whipworm, nodular worm, stomach worm, round worm, pinworm, heartworm), cestodes (e.g., tapeworms) and trematodes (e.g., liver fluke, blood fluke); protozoa such as coccidia, trypanosomes, trichomonads, amoebas and plasmodia; acanthocephalans such as thorny-headed worms (e.g., lingulatulida); and pentastomids such as tongueworms.

Detailed information regarding pests may be found in the "Handbook of Pest Control—The Behavior, Life History, and Control of Household Pests" by Arnold Mallis, $9^{th}$ Edition, copyright 2004 by GIE Media Inc, which is expressly incorporated by reference herein.

The present invention contemplates all vehicles by which the composition of the present invention can be formulated for delivery and use as a pesticide composition, including solutions, suspensions, emulsions, wettable powders and water dispersible granules, emulsifiable concentrates, granules, dusts, baits, and the like. Compositions suitable for administration to vertebrates or man include preparations suitable for oral, parenteral, percutaneous, e.g. pour-on, or topical administration.

Compositions for oral administration comprise one or more of the compounds of general formula I in association with pharmaceutically acceptable carriers or coatings and include, for example, tablets, pills, capsules, pastes, gels, drenches, medicated feeds, medicated drinking water, medicated dietary supplements, slow-release boluses or other slow-release devices intended to be retained within the gastro-intestinal tract. Any of these may incorporate active ingredient contained within microcapsules or coated with acid-labile or alkali-labile or other pharmaceutically acceptable enteric coatings. Feed premixes and concentrates containing compounds of the present invention for use in preparation of medicated diets, drinking water or other materials for consumption by animals may also be used.

Compositions for parenteral administration include solutions, emulsions or suspensions in any suitable pharmaceutically acceptable vehicle and solid or semisolid subcutaneous implants or pellets designed to release active ingredient over a protracted period and may be prepared and made sterile in any appropriate manner known to the art.

Compositions for percutaneous and topical administration include sprays, dusts, baths, dips, showers, jets, greases, shampoos, creams, wax-smears, or pour-on preparations and devices (e.g. ear tags) attached externally to animals in such a way as to provide local or systemic arthropod control Typically, formulations for application to plants or soil are applied following dilution of the concentrated formulation with water as aqueous solutions, suspensions or emulsions, or combinations thereof. Such solutions, suspensions or emulsions are produced from water-soluble, water-suspended or water-suspendable, water-emulsified or water-emulsifiable formulations or combinations thereof which are solids, including and usually known as wettable powders or water dispersible granules; or liquids including and usually known as emulsifiable concentrates, aqueous suspensions or suspension concentrates, and aqueous emulsions or emulsions in water, or mixtures thereof such as suspension-emulsions. As will be readily appreciated, any material to which this composition can be added may be used, provided they yield the desired utility without significant interference with the desired activity of the pesticidally active ingredients as pesticidal agents and improved residual lifetime or decreased effective concentration is achieved.

Wettable powders, which may be compacted to form water dispersible granules, comprise an intimate mixture of one or more of the pesticidally active ingredients, an inert carrier and surfactants. The concentration of the pesticidally active ingredient in the wettable powder is usually from about 10 percent to about 90 percent by weight based on the total weight of the wettable powder, more preferably about 25 weight percent to about 75 weight percent. In the preparation of wettable powder formulations, the pesticidally active ingredients can be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the pesticidally active ingredient comprise a convenient concentration, such as from about 10 weight percent to about 50 weight percent of the pesticidally active ingredient, in a suitable liquid, based on the total weight of the concentrate. The pesticidally active ingredients are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters esterified with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts of sulfated polyglycol ethers and appropriate salts of phosphated polyglycol ether.

Representative organic liquids which can be employed in preparing emulsifiable concentrates are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides; and glycol ethers such as the n-butyl ether, ethyl ether or methyl ether of diethylene glycol, and the methyl ether of triethylene glycol and the like. Mixtures of two or more organic liquids may also be employed in the preparation of the emulsifiable concentrate. Surface-active emulsifying agents are typically employed in liquid formulations and in an amount of from 0.1 to 20 percent by weight based on the combined weight of the emulsifying agents. The formulations can also contain other compatible additives, for example, plant growth regulators and other biologically active compounds used in agriculture.

Aqueous suspensions comprise suspensions of one or more water-insoluble pesticidally active ingredients dispersed in an aqueous vehicle at a concentration in the range from about 5 to about 50 weight percent, based on the total weight of the aqueous suspension. Suspensions are prepared by finely grinding one or more of the pesticidally active ingredients, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 50 weight percent, based on the total weight of the aqueous emulsion. If the pesticidally active ingredient is a solid it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compositions of the present invention can also be granular formulations, which are particularly useful for applications to the soil. Granular formulations usually contain from about 0.5 to about 10 weight percent, based on the total weight of the granular formulation of the pesticidally active ingredient(s), dispersed in an inert carrier which consists entirely or in large part of coarsely divided inert material such as attapulgite, bentonite, diatomite, clay or a similar inexpensive substance. Such formulations are usually prepared by dissolving the pesticidally active ingredients in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts can be prepared by intimately mixing one or more of the pesticidally active ingredients in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the pesticidally active ingredients onto the target site such as a crop or organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters of sulfosuccinic acids, ethoxylated organosilicones, ethoxylated fatty amines and blends of surfactants with mineral or vegetable oils.

The formulations may optionally include combinations that contain one or more other pesticidal compounds. Such additional pesticidal compounds may be fungicides, insecticides, nematicides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of the present invention, and the pesticidal compound in the combination can generally be present in a weight ratio of from 1:100 to 100:1.

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids.

Additionally, by way of non-limiting example, an acid function can form salts including those derived from alkali or alkaline earth metals and those derived from ammonia and amines. Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous NaOH, potassium carbonate, ammonia, and sodium bicarbonate. As an example, in many cases, a pesticide is modified to a more water soluble form e.g. 2,4-dichlorophenoxy acetic acid dimethyl amine salt is a more water soluble form of 2,4-dichlorophenoxy acetic acid, a well known herbicide.

The compounds disclosed in this invention can also form stable complexes with solvent molecules that remain intact after the non-complexed solvent molecules are removed from the compounds. These complexes are often referred to as "solvates".

Certain compounds disclosed in this document can exist as one or more stereoisomers. The various stereoisomers include geometric isomers, diastereomers, and enantiomers. Thus, the compounds disclosed in this invention include racemic mixtures, individual stereoisomers, and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

The compounds of the present invention can also be combined with other agricultural fungicides to form fungicidal mixtures and synergistic mixtures thereof. The fungicidal compounds of the present invention are often applied in conjunction with one or more other fungicides to control a wider variety of undesirable diseases. When used in conjunction with other fungicide(s), the presently claimed compounds can be formulated with the other fungicide(s), tank mixed with the other fungicide(s) or applied sequentially with the other fungicide(s). Such other fungicides include but are not limited to 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, BYF 1047, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, coumarin, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, isopyrazam, isotianil, kasugamycin, kasugamycin hydrochloride hydrate, kresoxim-methyl, mancopper, mancozeb, mandipropamid, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxinecopper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)-N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chloro-phenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenyl-itaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, IK-1140, and any combinations thereof.

Additionally, the compounds of the present invention can be combined with other pesticides, including insecticides, nematicides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present invention are often applied in conjunction with one or more other pesticides to control a wider variety of undesirable pests. When used in conjunction with other pesticides, the presently claimed compounds can be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad and spinetoram; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; diamide insecticides such as chlorantraniliprole, cyantraniliprole and flubendiamide; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethyl-amine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoatemethyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; oxadiazolone insecticides such as metoxadiazone; phthalimide insecticides such as dialifos, phosmet and tetramethrin; pyrazole insecticides such as acetoprole, cyenopyrafen, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cis-methrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetramic acid insecticides such as spirotetramat; tetronic acid insecticides such as spiromesifen; thiourea insecticides such as diafenthiuron; urea insecticides such as flucofuron and sulcofuron; and unclassified insecticides such as closantel, copper naphthenate, crotamiton, EXD, fenazaflor, fenoxacrim, hydramethylnon, isoprothiolane, malonoben, metaflumizone, nifluridide, plifenate, pyridaben, pyridalyl, pyrifluquinazon, rafoxanide, sulfoxaflor, triarathene, triazamate, and any combinations thereof.

Additionally, the compounds of the present invention may be combined with herbicides that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not limited to: amide herbicides such as allidochlor, beflubutamid, benzadox, benzipram, bromobutide, cafenstrole, CDEA, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; thioamide herbicides such as chlorthiamid; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; benzothiazole herbicides such as benzazolin; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glufosinate-P, glyphosate and piperophos; phenoxy herbicides such as bromofenoxim, clomeprop, 2,4-DEB, 2,4-DEP, difenopenten, disul, erbon, etnipromid, fenteracol and trifopsime; oxadiazoline herbicides such as methazole, oxadiargyl, oxadiazon; oxazole herbicides such as fenoxasulfone; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazole herbicides such as pyroxasulfone; benzoylpyrazole herbicides such as benzofenap, pyrasulfotole, pyrazolynate, pyrazoxyfen, and topramezone; phenylpyrazole herbicides such as fluazolate, nipyraclofen, pioxaden and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vemolate; thiocarbonate herbicides such as dimexano, EXD and proxan; thiourea herbicides such as methiuron; triazine herbicides such as dipropetryn, indaziflam, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, ipfencarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as benzfendizone, bromacil, butafenacil, flupropacil, isocil, lenacil, saflufenacil and terbacil; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, nicosulfuron, orthosulfamuron, oxasulfuron, primisulfuron, propyrisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, aminocyclopyrachlor, azafenidin, bentazone, benzobicyclon, bicyclopyrone, buthidazole, calcium cyanamide, cambendichlor, chlorfenac, chlorfenprop, chlorflurazole, chlorflurenol, cinmethylin, clomazone, CPMF, cresol, cyanamide, ortho-dichlorobenzene, dimepiperate, endothal, fluoromidine, fluridone, fluorochloridone, flurtamone, fluthiacet, indanofan, methyl isothiocyanate, OCH, oxaziclomefone, pentachlorophenol, pentoxazone, phenylmercury acetate, prosulfalin, pyribenzoxim, pyriftalid, quinoclamine, rhodethanil, sulglycapin, thidiazimin, tridiphane, trimeturon, tripropindan and tritac.

The compounds of the present invention may have broad ranges of efficacy as fungicides and insecticides. The exact amount of the active material to be applied is dependent not only on the specific active material being applied, but also on the particular action desired, the pathogen or pest to be controlled, and the stage of growth thereof, as well as the part of the plant, animal or other medium to be contacted with the compound. Thus, all the compounds, and formulations containing the same, may not be equally effective at similar concentrations or against the same pathogen and pest species.

The compounds are effective in use with plants in a phytologically acceptable amount. The term "phytologically acceptable amount" refers to an amount of a compound that kills or inhibits the pest or plant disease for which control is desired, but is not significantly toxic to the plant. This amount will generally be from about 0.1 to about 1000 ppm (parts per million), with 1 to 500 ppm being preferred.

The exact concentration of compound required varies with the pest or disease to be controlled, the type of formulation employed, the method of application, the particular plant or animal species, climate conditions, and the like. For fungicides, dilution and rate of application will depend upon the type of equipment employed, the method and frequency of application desired and diseases to be controlled, but the effective amount is usually from about 0.01 kilogram (kg) to about 20 kg, of active ingredient (a.i.) per hectare (ha). As a foliar fungicide, a compound of the present invention is usually applied to growing plants at a rate of about 0.1 to about 5 and preferably from about 0.125 to about 0.5 kg per hectare.

As a seed-applied fungicide, the amount of toxicant coated on the seed is usually at a dosage rate of about 0.1 to about 250 grams (g) and preferably from about 1 to about 60 g per 100 kilograms of seed. As a soil fungicide, the chemical can be incorporated in the soil or applied to the surface of the soil or a rice nursery box usually at a rate of about 0.1 to about 5 kg per hectare.

The actual amount of insecticide or miticide to be applied to loci of pests is generally not critical and can readily be determined by those skilled in the art. In general, concentrations from about 0.01 grams of pesticide per hectare to about 5000 grams of pesticide per hectare are expected to provide good control.

The locus to which a pesticide is applied can be any locus inhabited by an pest, for example, vegetable crops, fruit and nut trees, grape vines, ornamental plants, domesticated animals, the interior or exterior surfaces of buildings, and the soil around buildings. Controlling pests generally means that pest populations, activity, or both, are reduced in a locus. This can come about when: pest populations are repulsed from a locus; when pests are incapacitated, partially or completely, temporarily or permanently, in or around a locus; or pests are exterminated, in whole or in part, in or around a locus. Of course a combination of these results can occur. Generally, pest populations, activity, or both are desirably reduce more than fifty percent, preferably more than 90 percent, even more preferably 99 percent.

Generally, with baits, the baits are placed in the ground where, for example, termites can come into contact with the bait. Baits can also be applied to a surface of a building, (horizontal, vertical, or slant, surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant, or to a location where the root system of a plant can uptake pesticides. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention may be used with plants genetically transformed to express specialized traits, such as *Bacillus thuringiensis* or other insecticidal toxins, or those expressing herbicide resistance, or those with "stacked" foreign genes expressing insecticidal toxins, herbicide resistance, nutrition-enhancement or any other beneficial traits. An example of such a use is spraying such plants with the invention disclosed in this document.

The invention disclosed in this document may be suitable for controlling endoparasites and ectoparasites in the veterinary medicine sector or in the field of animal keeping. Compounds according to the invention are applied here in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document may also be employed advantageously in livestock keeping, for example, cattle, sheep, pigs, chickens, and geese. Suitable formulations may be administered orally to the animals with the drinking water or feed. The dosages and formulations that are suitable depend on the species.

In particular, the compounds of the present invention may effectively control a variety of undesirable insects and fungi that infect useful plant crops. Activity may be demonstrated for a variety of fungi, including those causing following the following plant diseases: Anthracnose of Cucumber (*Colletotrichum lagenarium*); Powdery Mildew of Cucumber (*Eysiphe* spp.); Glume Blotch of Wheat (*Septoria nodorum*); Downy Mildew of Cucumber (*Pseudoperonospora cubensis*); Rice Blast (*Magnaporthe grisea*); Brown Rust of Wheat (*Puccinia recondita tritici*); Stripe rust of wheat (*Puccinia striiformis*); Soybean rust (*Phakopspora pachyrhizi*); *Septoria* Blotch of Wheat (*Septoria tritici*); Apple scab (*Venturia inaequalis*); Downy mildew of grape (*Plasmopara viticola*); Powdery mildew of barley (*Erysiphe hordei*); Powdery mildew of wheat (*Erysiphe graminis*); Powdery mildew of grape (*Uncinula necator*); Late blight (*Phytophthora infestans*); Early blight (*Alternaria solani*); Peanut leaf spot (*Cercospora arachidicola*); Net blotch of barley (*Pyrenophora teres*); Barley scald (*Rhynchosporium secalis*); Spot blotch of cereals (*Cochliobolus sativus*); and Maize smut (*Ustilago maydis*).

Activity may be demonstrated by these compounds on a variety of insects, including Beet Armyworm (*Spodoptera exigua*), Mosquito (*Aedes aegypti*), Colorado Potato Beetle (*Leptinotarsa decemlineata*). Fruit Fly (*Drosophila melanogaster*), Green peach aphid (*Myzus persicae*), Cotton aphid (*Aphis gossypii*), and Bollworm/corn earworm (*Helicoverpa zea*).

It will be understood by those in the art that the efficacy of the compound on the foregoing fungi and insects establishes the general utility of the compounds as fungicides and insecticides.

PREPARATION 1

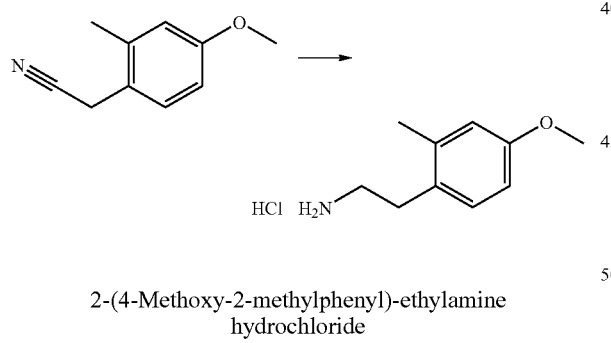

2-(4-Methoxy-2-methylphenyl)-ethylamine hydrochloride

4-Methoxy-2-methylphenylacetonitrile (3.0 g, 18.6 mmol) was dissolved in 2B ethanol (65 mL). To the solution was added con. HCl (2.4 mL) and 10% Pd/C (300 mg). The suspension was deaerated in a 500 mL Parr hydrogenation bottle and then pressurized with 55 psi $H_2$, and shaken. After 20 h, the reaction was recharged with hydrogen and 10% Pd/C. After a total of 96 h, the reaction mixture was filtered through Celite and the filtrate was concentrated in vacuo. The off-white solid residue was recrystallized from isopropanol and collected by suction filtration to afford 1.86 g (50% yield) 2-(4-methoxy-2-methylphenyl)-ethylamine hydrochloride as a white solid, melting point (M.P.) 220-222° C. (gradual softening and discoloration from 104-220° C.). The filtrate was concentrated in vacuo and the residue was washed with ethyl acetate and filtered, providing an additional 1.34 g for a total yield of 3.2 g (85% yield). GC/MS: m/z 165; $^1$H NMR (DMSO) 8.25 (bs, 3H), 7.09 (d, 1H), 6.75 (m, 2H), 3.71 (s, 3H), 2.87 (m, 4H), 2.27 (s, 3H).

PREPARATION 2

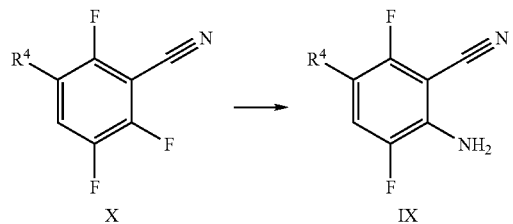

2-Amino-3,6-difluorobenzonitrile 2,3,6-Trifluorobenzonitrile (15 g) in ammonium hydroxide solution (28% in water; 80 mL) and acetonitrile (40 mL) was stirred at 70° C. in a pressure vessel for 16 h and the reaction was complete based on GC-MS. Acetonitrile was removed under reduced pressure, and water was added. The white solid precipitate was suction filtered, washed with water and dried under house vacuum over a weekend at room temperature to give 13.7 g (93%) of the crude product; M.P. 90-92° C. GC/MS: m/z 154. $^1$H NMR (CDCl$_3$): δ 7.07-7.16 (m, 1H), 6.36-6.43 (m, 1H), 4.65 (br s, 2H).

2-Amino-3,5,6-trifluorobenzonitrile was prepared in the same way, from 2,3,5,6-tetrafluorobenzonitrile (81% yield). GC/MS: m/z 172; $^1$H NMR (CDCl$_3$): δ 7.13 (m, 1H), 4.47 (br s, 2H); M.P. 112-115°.

PREPARATION 3

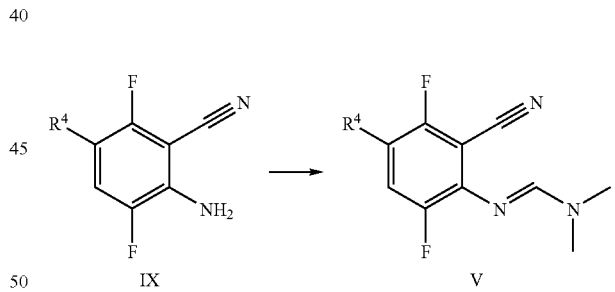

N'-(2-Cyano-3,6-difluorophenyl)-N,N-dimethylformamidine

A solution of 2-amino-3,6-difluorobenzonitrile (1.92 g, 12.5 mmol) and N,N-dimethylformamide dimethyl acetal (2.2 mL, 1.3 mmol) in 15 mL of toluene was heated to reflux for 1 h. The reaction was complete based on GC-MS. The solvent was removed in vacuo and the oily residue was suspended in hexane and a small amount of ether. The mixture was then cooled in a freezer for 20 min. The resulting solid was suction filtered, washed with hexane and dried to give 2.17 g (83% yield) of the product as a tan solid, M.P. 56-60°; GC/MS: m/z 209. $^1$H NMR (CDCl$_3$): δ 7.86 (s, 1H), 7.16 (m, 1H), 6.63 (m, 1H), 3.12 (s, 3H), 3.10 (s, 3H).

N'-(2-Cyano-3,4,6-trifluorophenyl)-N,N-dimethylformamidine was prepared in the same way, as a mixture of geometric isomers, from 2-amino-3,5,6-trifluorobenzonitrile (93% yield). ¹H NMR (CDCl₃): δ 7.80 (2s, integrate to 1H), 7.07-7.27 (m, 1H), 3.10 and 3.09 (2s, integrate to 6H); M.P. 83-86°.

PREPARATION 4

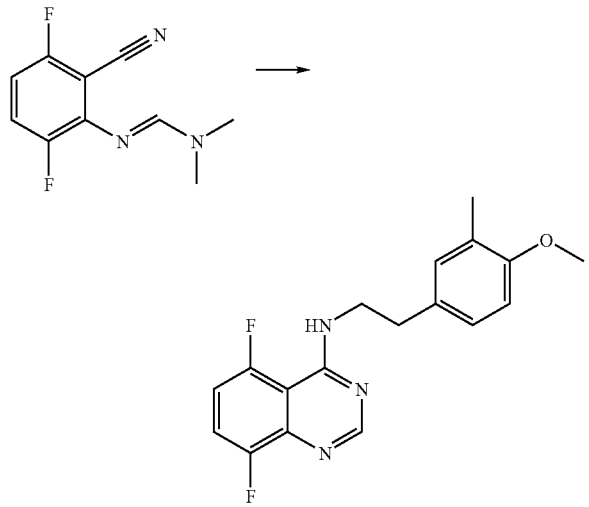

(5,8-Difluoroquinazolin-4-yl)-[2-(4-methoxy-3-methylphenyl)-ethyl]-amine

N'-(2-Cyano-3,6-difluorophenyl)-N,N-dimethylformamidine (1.65 g, 7.9 mmol) and 3-methyl-4-methoxyphenethylamine hydrochloride (2.4 g, 11.8 mmol) were combined in acetic acid (2.55 mL) and absolute ethanol (15 mL) and heated to reflux for 16 h. Upon cooling, the solvent was removed under reduced pressure and the remaining solid was slurried with water, suction filtered and washed with water, dried in vacuum at 45° C. to give 1.51 g (58%) of (5,8-difluoroquinazolin-4-yl)-[2-(4-methoxy-3-methylphenyl)-ethyl]-amine as an off-white solid. LC/MS: 330.18 (M⁺+1). ¹H NMR (CDCl₃): δ 8.67 (s, 1H), 7.35 (m, 1H), 6.94-7.09 (m, 3H), 6.79 (d, J=9.0 Hz, 1H), 6.65-6.80 (br, 1H), 3.87 (q, J=6.9 Hz, 2H), 3.83 (s, 3H), 2.93 (t, J=6.9 Hz, 2H), 2.22 (s, 3H). M.P. 162-169° C.

PREPARATION 5

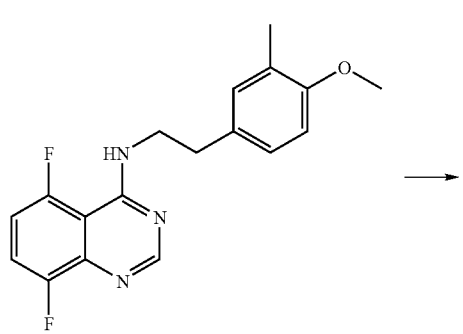

-continued

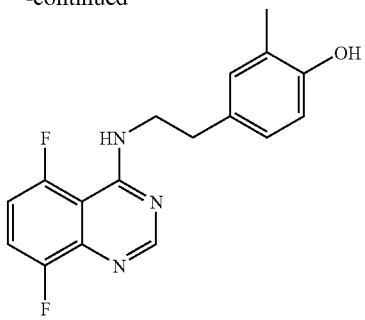

4-[2-(5,8-Difluoroquinazolin-4-ylamino)-ethyl]-2-methylphenol

To a solution of (5,8-difluoroquinazolin-4-yl)-[2-(4-methoxy-3-methylphenyl)-ethyl]-amine (0.86 g, 2.6 mmol) in CH₂Cl₂ (10 mL) cooled to −50° C., was added 7.8 mL BBr₃ (1 M in CH₂Cl₂, 7.8 mmol). The solution was allowed to warm to room temperature and stirred overnight, and then quenched slowly with methanol. The solvent was removed by rotary evaporation, and the residue was diluted with water and stirred for a few min. The pale yellow solid precipitate was collected by suction filtration, washed with water, and dried in vacuum at 50° C. overnight to give 0.83 g (quantitative yield) of 4-[2-(5,8-difluoroquinazolin-4-ylamino)-ethyl]-2-methylphenol. ¹H NMR (d₄-DMSO+d₆-acetone): δ 9.5-8.5 (m, 3H), 7.97 (m, 1H), 7.61 (m, 1H), 6.99 (s, 1H), 6.91 (d, J=8.1 Hz, 1H), 6.75 (d, J=8.1 Hz, 1H), 3.92 (m, 2H), 2.88 (t, J=7.8 Hz, 2H), 2.11 (s, 3H). LC/MS: 316.04 (M⁺+1). The product was used in the following reaction without further purification. M.P. 244-251° C.

EXAMPLE 1

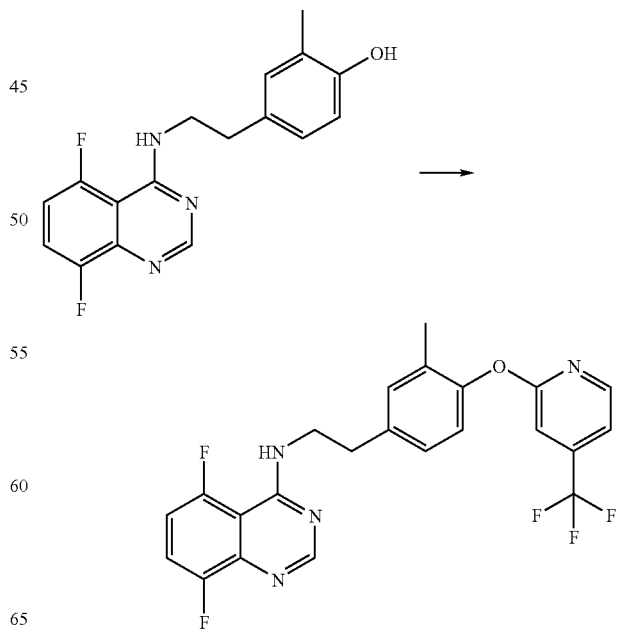

(5,8-Difluoroquinazolin-4-yl)-{2-[3-methyl-4-(4-trifluoromethylpyridin-2-yloxy)-phenyl]-ethyl}-amine A mixture of 4-[2-(5,8-difluoroquinazolin-4-ylamino)-ethyl]-2-methylphenol (0.47 g, 1.5 mmol), 2-fluoro-4-trifluoromethylpyridine (0.371 g, 2.25 mmol), and potassium carbonate (0.31 g, 2.25 mmol) in DMSO (7 mL) was heated at 90° C. overnight. The reaction was complete, as determined by LC-MS. After cooling to room temperature, water was added and the mixture was stirred for 10 min. The solid precipitate was collected by filtration, washed with water, and dried under vacuum at 50° C. to provide 0.533 g (77%) of (5,8-difluoroquinazolin-4-yl)-{2-[3-methyl-4-(4-trifluoromethylpyridin-2-yloxy)-phenyl]-ethyl}-amine as an off-white solid, M.P. 108-110° C. $^1$H NMR (CDCl$_3$): δ 8.69 (s, 1H), 8.31 (d, J=5.1 Hz, 1H), 7.34 (m, 1H), 7.13-7.21 (m, 4H), 6.96-7.03 (m, 2H), 6.71-6.84 (br, 1H), 3.94 (m, 2H), 3.02 (t, J=6.9 Hz, 2H), 2.17 (s, 3H). LC/MS: 461.13 (M$^+$+1).

PREPARATION 6

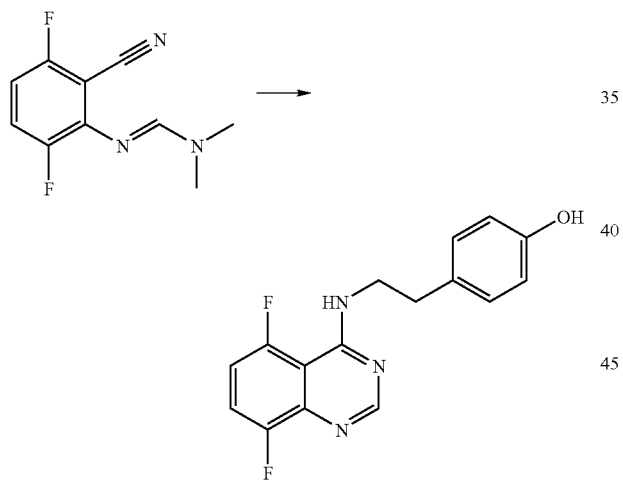

4-[2-(5,8-Difluoroquinazolin-4-ylamino)-ethyl]-phenol

A mixture of tyramine (2.62 g, 19 mmol), N'-(2-cyano-3,6-difluorophenyl)-N,N-dimethylformamidine (2.0 g, 9.56 mmol), acetic acid (3.4 mL, 60 mmol) and ethanol (50 mL) was heated at 75° C. for 16 h. Upon cooling, the solvent was removed under reduced pressure and the remaining solid was stirred in water for a few minutes, collected by suction filtration and washed with water. The filter cake was dried under vacuum to give 2.25 g (78%) of 4-[2-(5,8-difluoroquinazolin-4-ylamino)-ethyl]-phenol as an off-white solid, M.P. 221-222° C. $^1$H NMR (d$_6$-DMSO): δ 9.16 (s, 1H), 8.53 (s, 1H), 7.73 (m, 1H), 7.59 (m, 1H), 7.52 (m, 1H), 7.05 (d, J=8.4 Hz, 2H), 6.69 (d, J=8.4 Hz, 2H), 3.74 (q, J=7.8, 5.7 Hz, 2H), 2.84 (t, J=7.8 Hz, 2H). LC/MS: 302.04 (M$^+$+1).

EXAMPLE 2

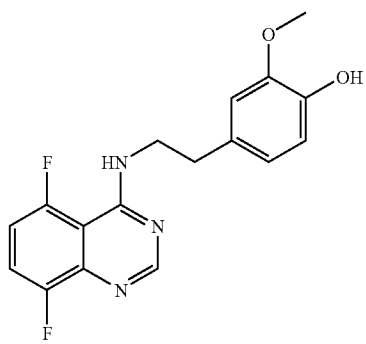

(5,8-Difluoroquinazolin-4-yl)-{2-[3-methoxy-4-(5-trifluoromethylpyridin-2-yloxy)-phenyl]-ethyl}-amine To a solution of 4-[2-(5,8-difluoroquinazolin-4-ylamino)-ethyl]-2-methoxyphenol (3.73 g, 11.25 mmol) in DMF (25 mL) in a dry 250 mL round bottom flask equipped with a dry nitrogen line and a magnetic stir bar was added sodium hydride (324 mg, 13.5 mmol). After gas evolution had subsided, 2-fluoro-5-trifluoromethyl-pyridine (2.05 g, 12.3 mmol) was added, and the reaction mixture was stirred at 25° C. After 20 h, additional sodium hydride (50 mg, 2.1 mmol) and 2-fluoro-5-trifluoromethyl-pyridine (100 mg, 0.6 mmol) were added. After 20 min, the reaction mixture was quenched by addition of sat. aq. NH$_4$Cl (30 mL) and concentrated in vacuo. The residue was suspended in water (50 mL) and stirred vigorously to break up chunks. The solid product was collected by suction filtration and washed on the filter with water. The filter cake again was suspended in water (50 mL) and stirred vigorously to break up chunks. The solid product was collected by suction filtration and washed with water. The filter cake was dried with suction on the filter overnight to provide 5.26 g (98% yield) of (5,8-difluoroquinazolin-4-yl)-{2-[3-methoxy-4-(5-trifluoromethylpyridin-2-yloxy)-phenyl]-ethyl}-amine as an off-white powder, M.P. 119-121° C. LC-MS: 477 (M$^+$+1); $^1$H NMR (CDCl$_3$): δ 8.69 (s, 1H), 8.4

(m, 1H), 7.89 (dd, 1H), 7.36 (m, 1H), 7.12 (m, 1H), 7.01 (m, 2H), 6.93 (m, 2H), 6.78 (bd, 1H), 3.97 (m, 2H), 3.75 (s, 3H), 3.06 (m, 2H).

PREPARATION 7

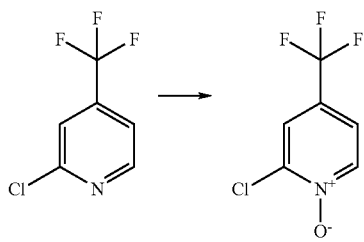

2-Chloro-4-trifluoromethylpyridine N-oxide

To a solution of 2-chloro-4-trifluoromethylpyridine (1.81 g, 10 mmol) in trifluoroacetic acid (12 mL) was added 30% hydrogen peroxide (8 mL), and the mixture was stirred at 50° C. over a weekend. The reaction mixture was poured into ice-cold water, neutralized with solid $Na_2CO_3$ with stirring, and extracted with ethyl acetate three times. The combined organic layer was dried over anhydrous $Na_2SO_4$, filtered, concentrated, and dried to give 1.67 g of analytically pure 2-chloro-4-trifluoromethylpyridine N-oxide as a brown oil. $^1$H NMR ($CDCl_3$): δ 8.45 (d, J=6.9 Hz, 1H), 7.77 (d, J=2.4 Hz, 1H), 7.47 (dd, J=6.9, 2.4 Hz, 1H). GC/MS: 197 [M]$^+$.

EXAMPLE 3

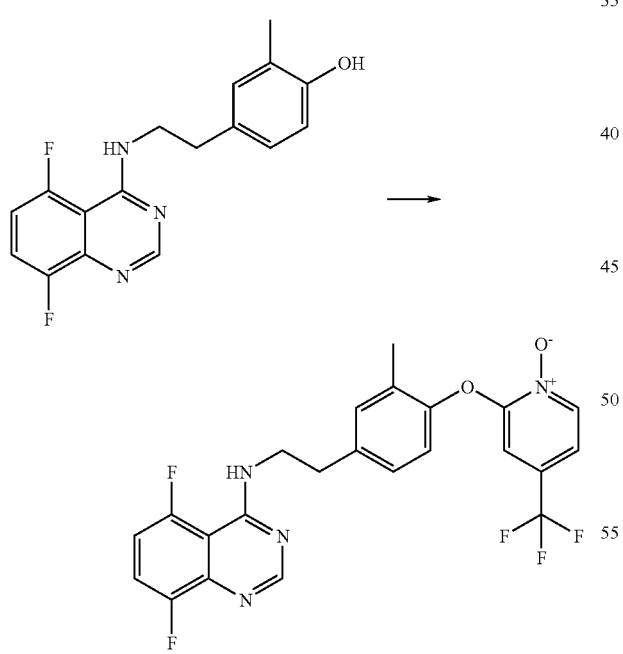

(5,8-Difluoroquinazolin-4-yl)-{2-[3-methyl-4-(1-oxy-4-trifluoromethylpyridin-2-yloxy)-phenyl]-ethyl}-amine A mixture of 4-[2-(5,8-difluoroquinazolin-4-ylamino)-ethyl]-2-methylphenol, (0.315 g, 1.0 mmol), 2-chloro-4-trifluoromethylpyridine N-oxide (0.20 g, 1.1 mmol) and potassium carbonate (0.207 g, 1.5 mmol) in DMSO (12 mL) was heated at 85° C. with microwave irradiation for 3 h. Water was added and the mixture was extracted with $CH_2Cl_2$. The pooled organic fraction was washed with brine, dried with $Na_2SO_4$, filtered, concentrated in vacuo, passed through a silica gel plug, and further eluted with EtOAc. The organic fractions were pooled and concentrated in vacuo to give 0.326 g of the product as a yellow gum. The product was redissolved in $CH_2Cl_2$ and washed with water to remove DMSO, dried with $Na_2SO_4$, filtered, and concentrated to give 0.286 g (60%) of (5,8-difluoroquinazolin-4-yl)-{2-[3-methyl-4-(1-oxy-4-trifluoromethylpyridin-2-yloxy)-phenyl]-ethyl}-amine (5,8-difluoroquinazolin-4-yl)-{2-[3-methyl-4-(1-oxy-4-trifluoromethylpyridin-2-yloxy)-phenyl]-ethyl}-amine as a yellow solid, M.P. 140-150°; MS m/z 476. $^1$H NMR ($CDCl_3$): δ 8.67 (s, 1H), 8.42 (d, J=6.6 Hz, 1H), 7.34 (m, 1H), 7.21-7.24 (m, 2H), 7.14-7.18 (m, 1H), 6.94-7.03 (m, 2H), 6.80 (d, J=2.4 Hz, 1H), 6.62-6.75 (br, 1H), 3.94 (q, J=7.2 Hz, 2H), 3.03 (t, J=7.2 Hz, 2H), 2.23 (s, 3H).

EXAMPLE 4

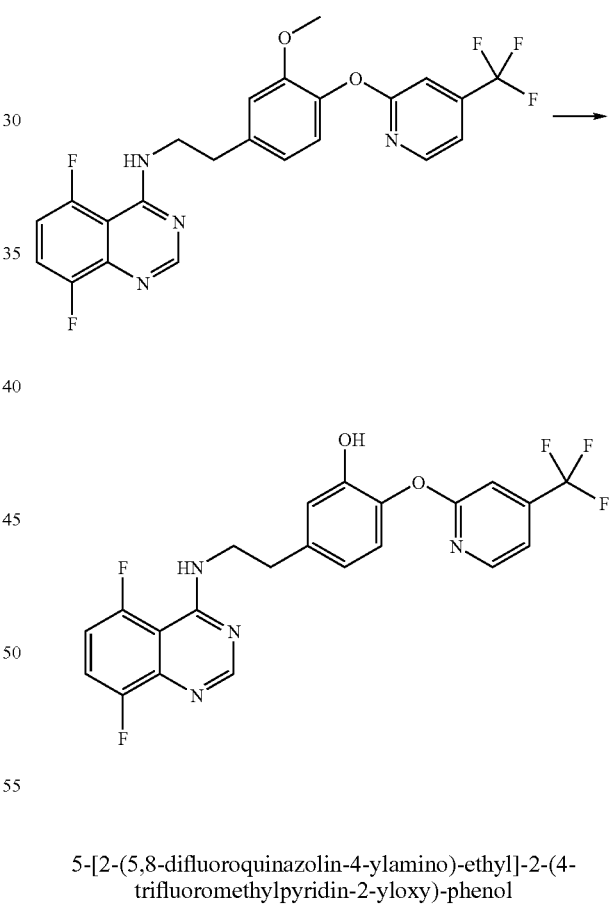

5-[2-(5,8-difluoroquinazolin-4-ylamino)-ethyl]-2-(4-trifluoromethylpyridin-2-yloxy)-phenol To a solution of (5,8-difluoroquinazolin-4-yl)-{2-[3-methoxy-4-(4-trifluoromethylpyridin-2-yloxy)-phenyl]-ethyl}-amine (2.71 g, 5.69 mmol) in $CH_2Cl_2$ (25 mL) cooled to −50° C., was added 1 M $BBr_3$ in $CH_2Cl_2$ (17 mL, 17 mmol). The solution was allowed to warm to room temperature and stirred overnight, and then quenched slowly with methanol. The solvent was removed by rotary evaporation and the residue was suspended in chloroform. The product was collected by suction filtration to give 2.70 g (quantitative) of 5-[2-(5,8-difluoroquinazolin-4-ylamino)-ethyl]-2-(4-trifluoromethylpyridin-2-yloxy)-phenol. The product was used in the following reaction without further purification. $^1$H NMR (CD$_3$OD): δ 8.78 (s, 1H), 8.39 (d, J=5.4 Hz, 1H), 7.93 (m, 1H), 7.54 (m, 1H), 7.45 (d, J=5.4 Hz, 1H), 7.19 (s, 1H), 7.08 (d, J=7.8 Hz, 1H), 6.96 (d, J=2.1 Hz, 1H) 6.87 (dd, J=7.8, 2.1 Hz, 1H), 4.12 (t, J=7.5 Hz, 2H), 3.05 (t, J=7.5 Hz, 2H). LC/MS: 460.97 (M$^+$−1).

EXAMPLE 5

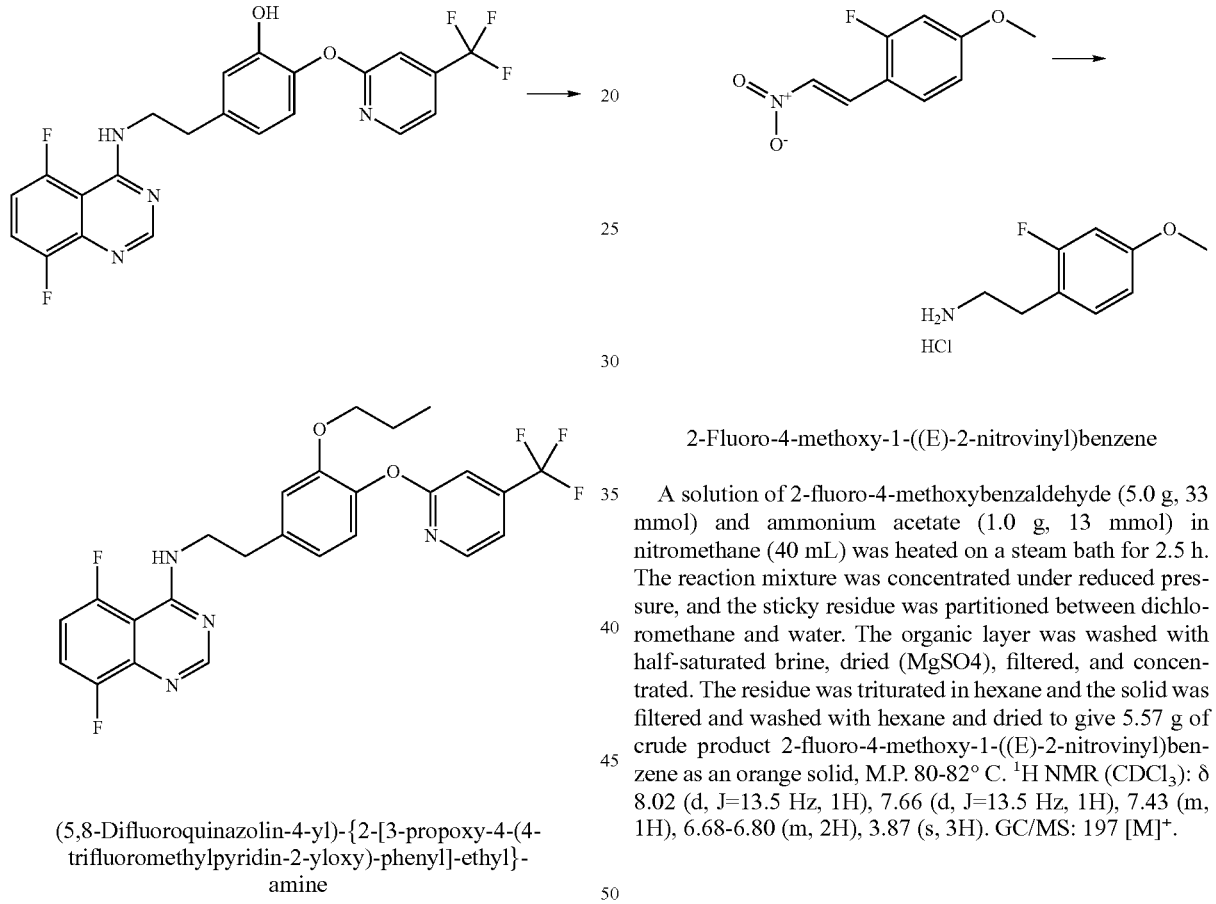

(5,8-Difluoroquinazolin-4-yl)-{2-[3-propoxy-4-(4-trifluoromethylpyridin-2-yloxy)-phenyl]-ethyl}-amine To a solution of 5-[2-(5,8-difluoroquinazolin-4-ylamino)-ethyl]-2-(4-trifluoromethylpyridin-2-yloxy)-phenol (0.462 g, 0.5 mmol) in DMSO (5 mL) was added 1-iodopropane (0.204 g, 1.2 mmol) and K$_2$CO$_3$ (0.207 g, 1.5 mmol). The reaction mixture was stirred at 50° C. overnight and then at 70° C. for another 24 h. After cooling to room temperature, the mixture was poured into water and the gum-like material was separated via suction filtration and washed with water. The gum-like product then was partitioned between CH$_2$Cl$_2$ and brine. The organic phase was dried over sodium sulfate and concentrated in vacuo, and the product was purified by preparative reverse phase HPLC to give 0.161 g (32%) of (5,8-difluoroquinazolin-4-yl)-{2-[3-propoxy-4-(4-trifluoromethylpyridin-2-yloxy)-phenyl]-ethyl}-amine as a brown gum; MS m/z 504. $^1$H NMR (CDCl$_3$): δ 8.68 (s, 1H), 8.26 (d, J=4.8 Hz, 1H), 7.33 (m, 1H), 7.08-7.15 (m, 3H), 6.87-7.03 (m, 3H), 6.70-6.83 (br, 1H), 3.89-3.97 (m, 2H), 3.80-3.86 (m, 2H), 3.02 (t, J=6.9 Hz, 2H), 1.51 (m, 2H), 0.66 (t, J=7.2 Hz, 3H). LC/MS: 506.10 (M$^+$+1).

PREPARATION 8

2-Fluoro-4-methoxy-1-((E)-2-nitrovinyl)benzene

A solution of 2-fluoro-4-methoxybenzaldehyde (5.0 g, 33 mmol) and ammonium acetate (1.0 g, 13 mmol) in nitromethane (40 mL) was heated on a steam bath for 2.5 h. The reaction mixture was concentrated under reduced pressure, and the sticky residue was partitioned between dichloromethane and water. The organic layer was washed with half-saturated brine, dried (MgSO4), filtered, and concentrated. The residue was triturated in hexane and the solid was filtered and washed with hexane and dried to give 5.57 g of crude product 2-fluoro-4-methoxy-1-((E)-2-nitrovinyl)benzene as an orange solid, M.P. 80-82° C. $^1$H NMR (CDCl$_3$): δ 8.02 (d, J=13.5 Hz, 1H), 7.66 (d, J=13.5 Hz, 1H), 7.43 (m, 1H), 6.68-6.80 (m, 2H), 3.87 (s, 3H). GC/MS: 197 [M]$^+$.

2-(2-Fluoro-4-methoxyphenyl)ethylamine hydrochloride

Under a nitrogen atmosphere, 2-fluoro-4-methoxy-1-((E)-2-nitrovinyl)benzene (26.5 g, 134.5 mmol) was added in portions to a suspension of LiAlH$_4$ (16 g, 195 mmol) in THF (1 L) at 0° C. The mixture then was heated at reflux, and after 3.5 h, the reaction was complete as indicated by GC. The mixture was cooled to 0° C. and quenched carefully with water (34.6 mL) and 10% aqueous NaOH (28 mL). After removal of green precipitates by suction filtration, the filtrate was dried over MgSO$_4$, filtered and evaporated under reduced pressure. The oily residue was dissolved in EtOAc (150 mL) and then conc. HCl was added until pH reached 1, to form the hydrochloride salt. Ether was added (1 L) with stirring and the solid was collected by suction filtration and washed with a small amount of acetone, then dried under vacuum to give 2-(2- fluoro-4-methoxyphenyl)ethylamine hydrochloride as a white solid weighing 12.3 g, M.P. 162-165° C. The filtrate was concentrated under reduced pressure. Toluene was added and evaporated to azeotropically remove the remaining water. The residue was dissolved in MeOH, and EtOAc was added to precipitate the product which was filtered and washed with ethyl acetate, affording another 7.3 g of product. The total yield was 19.6 g (72%). $^1$H NMR (CDCl$_3$): δ 8.29 (br, 3H), 7.24 (t, J=8.7 Hz, 1H), 6.73-6.84 (m, 2H), 3.74 (s, 3H), 2.83-2.99 (m, 4H). LC/MS: 169.9 [M]$^+$-HCl.

EXAMPLE 6

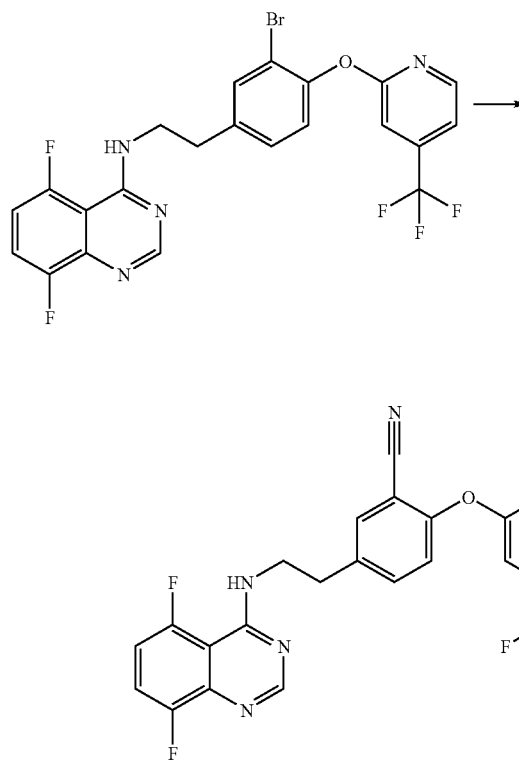

5-[2-(5,8-Difluoroquinazolin-4-ylamino)-ethyl]-2-(4-trifluoromethylpyridin-2-yloxy)-benzonitrile A suspension of {2-[3-bromo-4-(4-trifluoromethylpyridin-2-yloxy)-phenyl]-ethyl}-(5,8-difluoroquinazolin-4-yl)-amine) (137 mg, 0.26 mmol), CuCN (164 mg, 1.83 mmol) and DMF (10 mL) was heated at 126° for 3 h, then heated at reflux overnight. After addition of more CuCN (100 mg), the reaction was heated at reflux 2 h, then concentrated in vacuo. The residue was partitioned between water (10 mL) and EtOAc (10 mL). The aqueous layer was extracted with EtOAc (2×10 mL) and the pooled organic fractions were dried (Na$_2$SO$_4$), filtered through a silica gel/Celite plug and concentrated in vacuo to provide 5-[2-(5,8-difluoroquinazolin-4-ylamino)-ethyl]-2-(4-trifluoromethylpyridin-2-yloxy)-benzonitrile (70 mg) as an off-white powder (94% purity by LC), 57% yield, M.P. 157-159°. $^1$H NMR (CDCl$_3$): δ 8.7 (bs, 1H), 8.29 (d, 1H), 7.62 (d, 1H), 7.57 (dd, 1H), 7.38 (m, 1H), 7.29 (s, 1H), 7.27 (s, 1H), 7.26 (m, 1H), 7.04 (m, 1H), 6.76 (bm, 1H), 3.96 (m, 2H), 3.10 (t, 2H). MS: m/z 471.

EXAMPLE 7

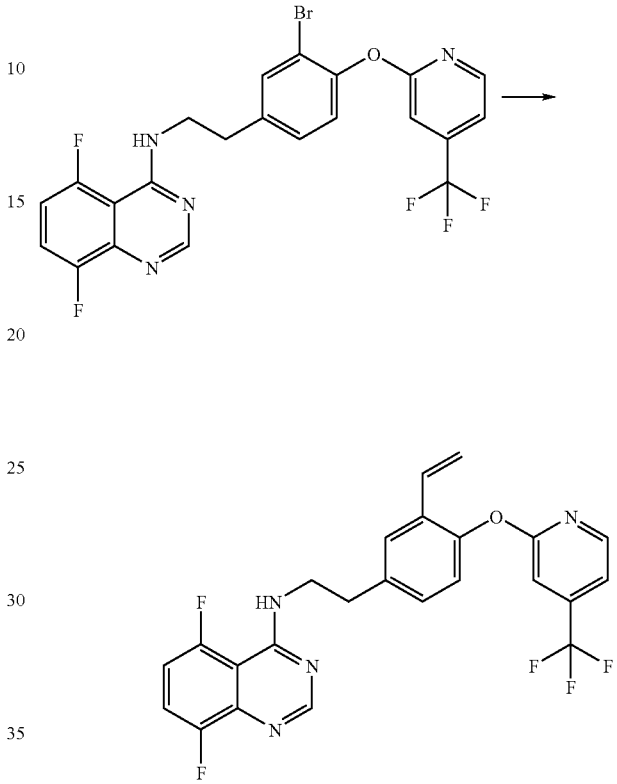

(5,8-Difluoroquinazolin-4-yl)-{2-[4-(4-trifluoromethylpyridin-2-yloxy)-3-vinylphenyl]-ethyl}-amine {2-[3-Bromo-4-(4-trifluoromethylpyridin-2-yloxy)-phenyl]-ethyl}-(5,8-difluoroquinazolin-4-yl)-amine (890 mg, 1.7 mmol), vinyl tri-n-butyltin (591 mg, 544 µL, 1.9 mmol), 1,4-bis(diphenylphosphino)butane (145 mg, 0.3 mmol), 2,6-di-tert-butyl-4-methylphenol (75 mg, 0.3 mmol) and Pd(OAc)$_2$ (49 mg, 0.22 mmol) were added to a Carousel reactor tube containing toluene (5 mL) and fitted with a magnetic stir bar and a dry nitrogen gas line. The reaction mixture was heated to reflux. After 20 h, more Pd(OAc)$_2$ (49 mg, 0.22 mmol) was added, and heating was continued. After another 20 h, the reaction was cooled. The reaction mixture was washed sequentially with water and brine, then dried (Na$_2$SO$_4$), filtered through a silica gel and Celite plug, and concentrated in vacuo. The residue was partitioned between acetonitrile (30 mL) and pentane (5×20 mL). The acetonitrile fraction then was purified by normal phase chromatography (silica gel with ethyl acetate/cyclohexane eluent) and reverse phase chromatography (C-18 solid phase with acetonitrile/water eluent, 0.5% H$_3$PO$_4$) to provide (5,8-difluoroquinazolin-4-yl)-{2-[4-(4-trifluoromethylpyridin-2-yloxy)-3-vinylphenyl]-ethyl}-amine as a white powder (375 mg), M.P. 86°. $^1$H NMR (CDCl$_3$): δ 8.7 (s, 1H), 8.31 (d, 1H), 7.54 (d, 1H), 7.35 (m, 1H), 7.24 (m, 1H), 7.18 (m, 1H), 7.14 (s, 1H), 7.06 (d, 1H), 6.78 (bm, 2H), 5.76 (d, 1H), 5.26 (d, 1H), 3.97 (m, 2H), 3.07 (t, 2H). MS: m/z 472.

(m, 2H), 7.13 (s, 1H), 7.00 (m, 2H), 6.76 (bm, 1H), 3.95 (m, 2H), 3.04 (t, 2H), 2.55 (q, 2H), 1.16 (t, 3H). MS: m/z 474.

EXAMPLE 8

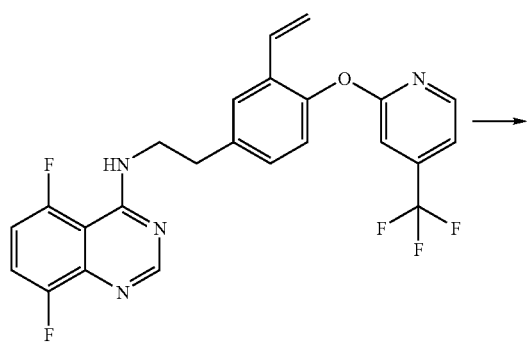

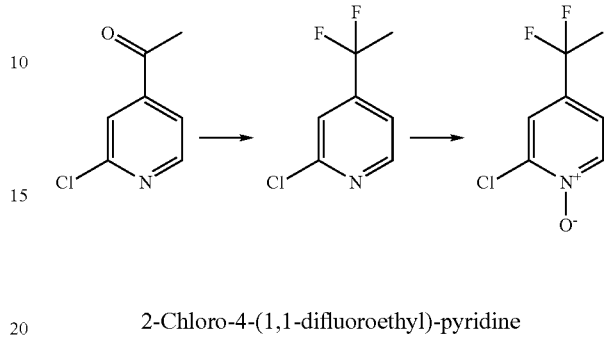

PREPARATION 9

2-Chloro-4-(1,1-difluoroethyl)-pyridine

To a solution of 2-chloro-4-acetylpyridine (2.6 g, 17.2 mmol) in $CH_2Cl_2$ (50 mL) was added diethylamino-sulfurtrifluoride (8 mL, 60 mmol) at 25° C. and the mixture was stirred 16 h. The reaction was quenched by addition of saturated aqueous $NaHCO_3$ dropwise at 0° C. After separation of the two phases, the organic phase was dried over $Na_2SO_4$, filtered, and concentrated in vacuo. The residue was purified by column chromatography over silica gel with 10% EtOAc in hexane to yield 2-chloro-4-(1,1-difluoroethyl)pyridine (1.72 g) as a light brown oil. GC/MS: m/z 177 [M$^+$].

2-Chloro-4-(1,1-difluoroethyl)-pyridine 1-oxide

To a solution of 2-chloro-4-(1,1-difluoro)ethylpyridine (1.27 g, 7 mmol) in trifluoroacetic acid was added 30% hydrogen peroxide (6 mL) and the solution was heated at reflux 2.5 h. The reaction was concentrated in vacuo and the residue poured into ice-cold water. The mixture was neutralized with $Na_2CO_3$ and then extracted with EtOAc and $CH_2Cl_2$. The pooled organic layers were filtered and concentrated in vacuo to give 2-chloro-4-(1,1-difluoroethyl)-pyridine 1-oxide (1.00 g) as a brown oil. $^1$H NMR (CDCl$_3$): δ 8.39 (d, J=6.6 Hz, 1H), 7.63 (d, J=2.4 Hz, 1H), 7.33 (dd, J=6.6, 2.4 Hz, 1H), 1.94 (t, J=18 Hz, 3H). GC/MS: m/z 193 [M$^+$].

PREPARATION 10

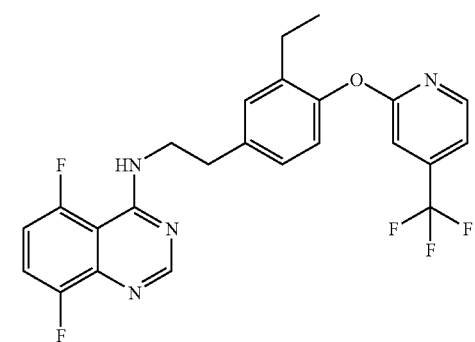

(5,8-Difluoroquinazolin-4-yl)-{2-[3-ethyl-4-(4-trifluoromethylpyridin-2-yloxy)-phenyl]-ethyl}-amine (5,8-Difluoroquinazolin-4-yl)-{2-[4-(4-trifluoromethyl-pyridin-2-yloxy)-3-vinylphenyl]-ethyl}-amine (250 mg), 10% Pd—C (100 mg) and ethyl acetate (10 mL) were added to a 230 mL Corning shaker bottle filled with nitrogen gas. The bottle was evacuated, then charged with hydrogen (55 psi starting pressure) and shaken overnight. The reaction mixture was filtered through Celite, and concentrated in vacuo. The residue was purified by reverse phase chromatography (C-18 solid phase with acetonitrile/water eluent, 0.5% $H_3PO_4$) to provide (5,8-difluoroquinazolin-4-yl)-{2-[3-ethyl-4-(4-trifluoromethylpyridin-2-yloxy)-phenyl]-ethyl}-amine as a white powder (77 mg), M.P. 121-122°. $^1$H NMR (CDCl$_3$): δ 8.69 (s, 1H), 8.31 (d, 1H), 7.36 (m, 1H), 7.22 (m, 1H), 7.17

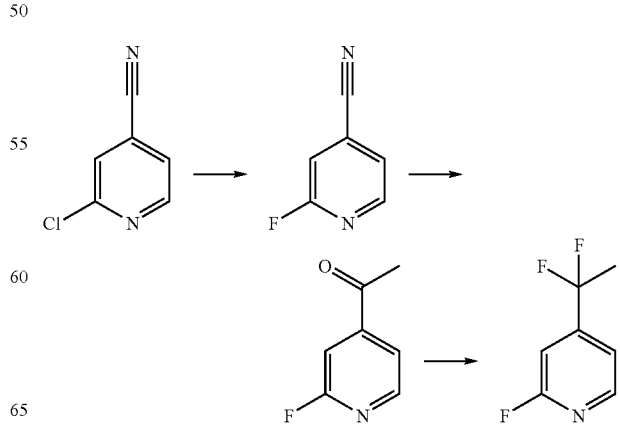

2-Fluoroisonicotinonitrile

Cesium fluoride (30 g, 0.22 mmol) was slurried in 150 mL dry sulfolane and concentrated via vacuum distillation at 0.5 mm Hg. After removal of 20% of the solvent, the suspension was cooled and 2-chloroisonicotinonitrile (15 g, 0.11 mmol) was added then stirred and heated at 100° C. for 20 h. It was cooled to 25° C., poured into 200 mL water and extracted with Et$_2$O. The ether phase was washed with water, then brine, dried over Na$_2$SO$_4$, filtered and concentrated in vacuo. The residue was purified by column chromatography over silica gel with CH$_2$Cl$_2$ to give 12.0 g of 2-fluoroisonicotinonitrile as a low-melting colorless solid. MS m/z 122. $^1$H NMR (CDCl$_3$): δ 8.45 (dd, 1H), 7.47 (dd, 1H), 7.24 (m, 1H).

1-(2-Fluoropyridin-4-yl)-ethanone

To a solution of 2-fluoroisonicotinonitrile (10 g, 82 mmol) in anhydrous Et$_2$O (250 mL) cooled in an ice-water bath was slowly added 3M methyl magnesium bromide in hexane (40 mL, 120 mmol). The mixture was stirred at 25° C. overnight. The reaction was quenched slowly with 1N aq. citric acid solution at 0° C. until all solids dissolved. Brine was added and the two phases were separated. The organic phase was dried over Na$_2$SO$_4$, filtered, and concentrated in vacuo to give 1-(2-fluoropyridin-4-yl)-ethanone (6.2 g) as a brown oil. The aqueous phase was stirred at 25° C. for 3 h, then extracted with CH$_2$Cl$_2$. The dichloromethane layer was dried over Na$_2$SO$_4$, filtered, and concentrated in vacuo to give an additional 1.1 g of the product, for a total of 7.3 g, used in the next step without further purification. MS m/z 139. $^1$H NMR (CDCl$_3$): δ 8.25 (dd, 1H), 7.47 (d, 1H), 7.21 (m, 1H).

2-Fluoro-4-(1,1-difluoroethyl)pyridine 1-(2-Fluoropyridin-4-yl)-ethanone (6.2 g, 44.6 mmol) from the previous reaction was treated with diethylaminosulfurtrifluoride (17 mL, 130 mmol), as in Preparation 9, to yield 3.5 g of 2-fluoro-4-(1,1-difluoroethyl)pyridine (45% yield), as a light yellow oil. GC/MS: m/z 161 [M$^+$].

EXAMPLE 9

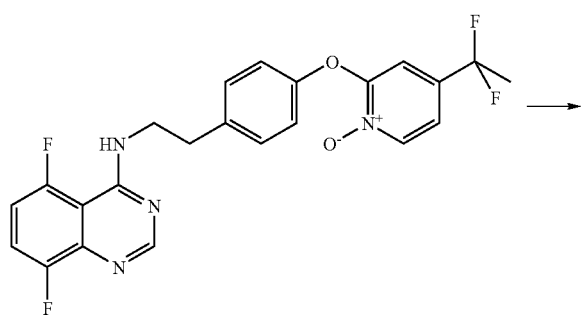

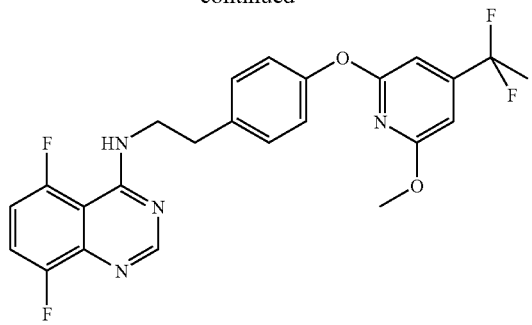

(2-{4-[4-(1,1-Difluoroethyl)-6-methoxypyridin-2-yloxy]-phenyl}-ethyl)-(5,8-difluoroquinazolin-4-yl)-amine To an ice-cold solution of (2-{4-[4-(1,1-difluoroethyl)-1-oxypyridin-2-yloxy]phenyl}ethyl)-(5,8-difluoroquinazolin-4-yl)amine (0.37 g, 0.85 mmol) and ethyl chloroformate (0.22 g, 2.0 mmol) in MeOH (10 mL) was added triethylamine (0.48 mL, 3.4 mmol) with stirring. The reaction mixture was heated at reflux for 40 h. The solvent was removed under reduced pressure, and the residue was then dissolved in chloroform. The solution was washed with water, dried over Na$_2$SO$_4$, filtered, concentrated, and the residue was purified by column chromatography over silica gel with 10% EtOAc in hexane to yield 0.128 g (33% yield) of the product as a pale brown oil. $^1$H NMR (CDCl$_3$): δ 8.69 (s, 1H), 7.27-7.39 (m, 3H), 7.14 (d, J=8.4 Hz, 2H), 7.00 (m, 1H), 6.65-6.79 (br, 1H), 6.54 (s, 1H), 6.43 (s, 1H), 3.96 (q, J=6.9 Hz, 2H), 3.79 (s, 3H), 3.05 (t, J=6.9 Hz, 2H), 1.85 (t, J=18.3 Hz, 3H). LC/MS: 473.2 (M$^+$+1).

EXAMPLE 10

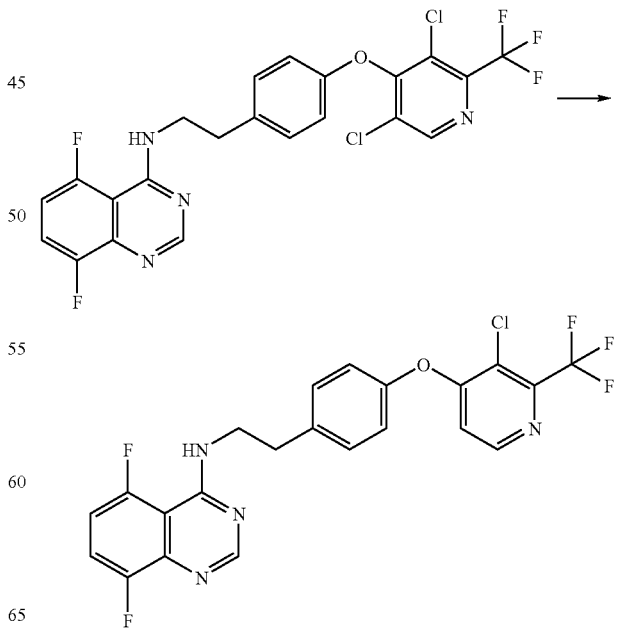

{2-[4-(3-Chloro-2-trifluoromethylpyridin-4-yloxy)-phenyl]-ethyl}-(5,8-difluoroquinazolin-4-yl)-amine {2-[4-(3,5-dichloro-2-trifluoromethylpyridin-4-yloxy)-phenyl]-ethyl}-(5,8-difluoroquinazolin-4-yl)-amine (700 mg, 1.4 mol) was dissolved in 2B EtOH (100 mL) under nitrogen in a Parr shaker bottle. Triethylamine (130 mg) and 10% Pd/C (200 mg) were added and the bottle was charged with H$_2$ to an initial pressure of 50 psi. After shaking for approx. 10 min (approx 1 psi H$_2$ uptake), the reaction was filtered through Celite and concentrated in vacuo to provide a white solid. The solid was partitioned between water and EtOAc twice, and the pooled fractions were dried and concentrated in vacuo. The residue was triturated with Et$_2$O, to afford 310 mg of {2-[4-(3-chloro-2-trifluoromethylpyridin-4-yloxy)-phenyl]-ethyl}-(5,8-difluoroquinazolin-4-yl)-amine as a white crystalline solid, M.P. 129-131°. $^1$H NMR (400 MHz, CDCl$_3$) δ 8.69 (s, 1 H), 8.35 (d, J=5.4 Hz, 1 H), 7.40-7.31 (m, 3 H), 7.12-7.06 (m, 2 H), 7.05-6.97 (m, 1 H), 6.85-6.66 (m, 2 H), 4.01-3.92 (m, 2 H), 3.09 (t, J=7.1 Hz, 2 H); MS: m/z 480.

EXAMPLE 11

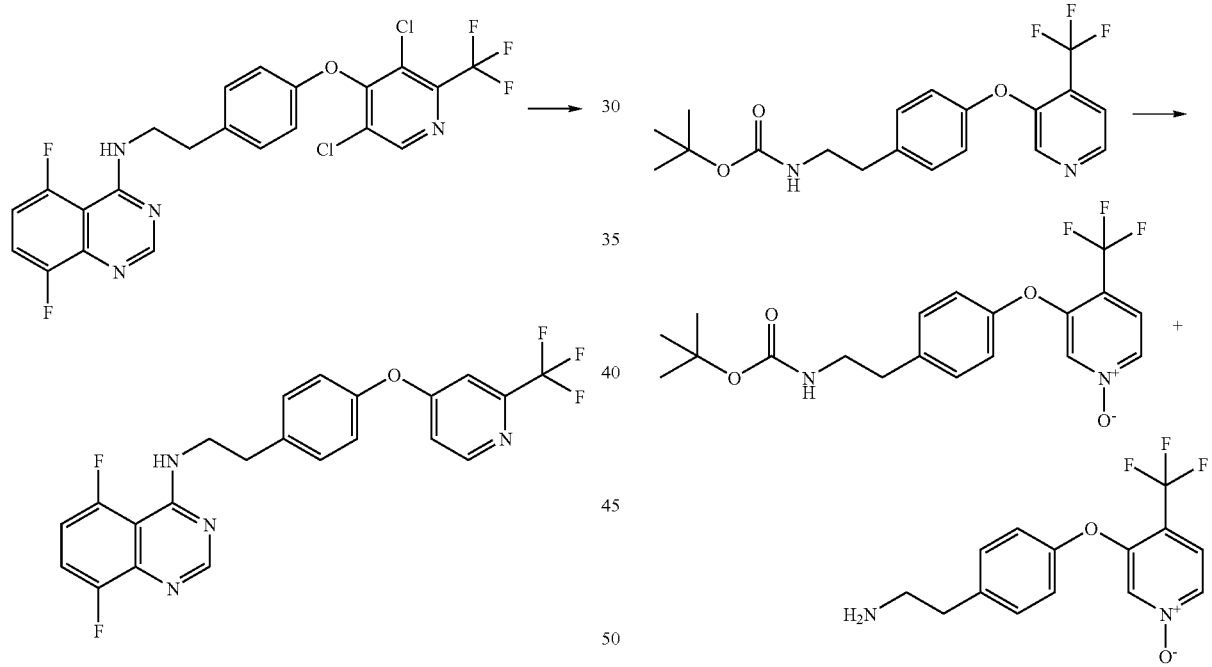

(5,8-Difluoroquinazolin-4-yl)-{2-[4-(2-trifluoromethylpyridin-4-yloxy)-phenyl]-ethyl}-amine To a suspension of 20% Pd(OH)$_2$ (500 mg) and sodium acetate (368 mg, 4.5 mmol) and absolute EtOH (100 mL) under N$_2$ in a 230 mL Corning shaker bottle was added {2-[4-(3,5-dichloro-2-trifluoromethylpyridin-4-yloxy)-phenyl]-ethyl}-(5,8-difluoroquinazolin-4-yl)-amine (1.15 g, 2.2 mmol). After deaerating, the bottle was charged with H$_2$ (57 psig initial pressure) and shaken at room temp on Parr apparatus. After 24 h, another aliquot of 20% Pd(OH)$_2$ was added, and the bottle was recharged with H$_2$. After another 24 h, the reaction mixture was degassed, placed under nitrogen gas, and then filtered through Celite. The filtrate was evaporated and the residue was purified via preparative reverse phase LC (70% CH$_3$CN/H$_2$O, 0.5% H$_3$PO$_4$ eluant) to provide 390 mg of (5,8-difluoroquinazolin-4-yl)-{2-[4-(2-trifluoromethylpyridin-4-yloxy)-phenyl]-ethyl}-amine as an off-white powder, M.P. 95-96°. $^1$H NMR (400 MHz, CDCl$_3$) δ 8.69 (s, 1 H), 8.56 (d, J=5.7 Hz, 1 H), 7.40-7.31 (m, 3 H), 7.19 (d, J=2.4 Hz, 1 H), 7.10-7.05 (m, 2 H), 7.04-6.95 (m, 2 H), 6.73 (dt, J=16.6, 5.4 Hz, 1 H), 3.97 (q, J=6.9 Hz, 2 H), 3.09 (t, J=7.1 Hz, 1 H); MS: m/z 446.

PREPARATION 11

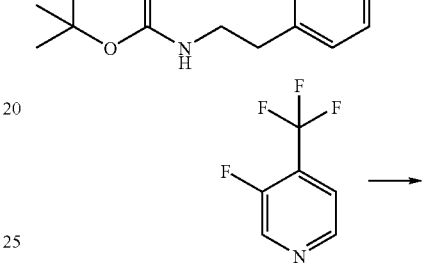

{2-[4-(4-Trifluoromethylpyridin-3-yloxy)-phenyl]-ethyl}-carbamic acid tert-butyl ester To a solution of 3-fluoro-4-trifluoromethylpyridine (1 g, 6.1 mmol) and [2-(4-hydroxyphenyl)-ethyl]-carbamic acid tert-butyl ester (1.44 g, 6.1 mmol) in DMSO (10 mL) was added K$_2$CO$_3$ (5 g, 36.2 mmol), and the mixture was heated at 100° C. for 30 min. After cooling, the solids were removed by suction filtration and washed with Et$_2$O. The pooled filtrates were diluted with Et$_2$O (75 mL) and washed with 0.01 N HCl. The organic layer was concentrated in vacuo. The residue was dissolved in Et$_2$O/hexane and washed with 10% NaOH. The organic layer was filtered and vacuum dried to provide 1.4 g (60% yield) of {2-[4-(4-trifluoromethyl-pyridin-3-yloxy)-phenyl]-ethyl}-carbamic acid tert-butyl ester as a clear, colorless oil.

2-[4-(1-Oxy-4-trifluoromethylpyridin-3-yloxy)-phenyl]-ethylamine

To a solution of {2-[4-(4-trifluoromethylpyridin-3-yloxy)-phenyl]-ethyl}-carbamic acid tert-butyl ester (0.87 g, 2.3 mmol) in DCM (40 mL) was added pulverized commercial urea/hydrogen peroxide (0.45 g, 4.8 mmol) and trifluoroacetic anhydride (1.2 g, 5.7 mmol). After 4 h, water (120 mL) was added. After 15 h, concentrated aqueous sodium bisulfite solution was added to achieve a negative peroxide test. The reaction mixture was extracted with $Et_2O$ and the pooled organics were filtered and concentrated in vacuo to provide 0.89 g of a semi-solid. This material was boiled in hexane, and the hexane supernatant was decanted to leave 290 mg (43% yield) of 2-[4-(1-oxy-4-trifluoromethylpyridin-3-yloxy)-phenyl]-ethylamine as a yellow gum, used without further purification in the next step.

The hexane solution was concentrated in vacuo, and the residue was dissolved in minimal diethyl ether, then diluted with 3 volumes of pentane. Glassy crystals formed and were collected by suction filtration to provide {2-[4-(1-oxy-4-trifluoromethylpyridin-3-yloxy)-phenyl]-ethyl}-carbamic acid tert-butyl ester as a crystalline solid (150 mg, 16% yield), M.P. 97-99°. $^1$H NMR (400 MHz, $CDCl_3$) δ 7.95 (d, J=6.4 Hz, 1 H), 7.76 (s, 1 H), 7.48 (d, J=6.8 Hz, 1 H), 7.29-7.23 (m, 2 H), 7.07-7.00 (m, 2 H), 4.60 (br, 1 H), 3.43-3.33 (m, 2H), 2.83 (t, J=7.0 Hz, 2 H), 1.45 (s, 9 H); MS m/z 398.

EXAMPLE 12

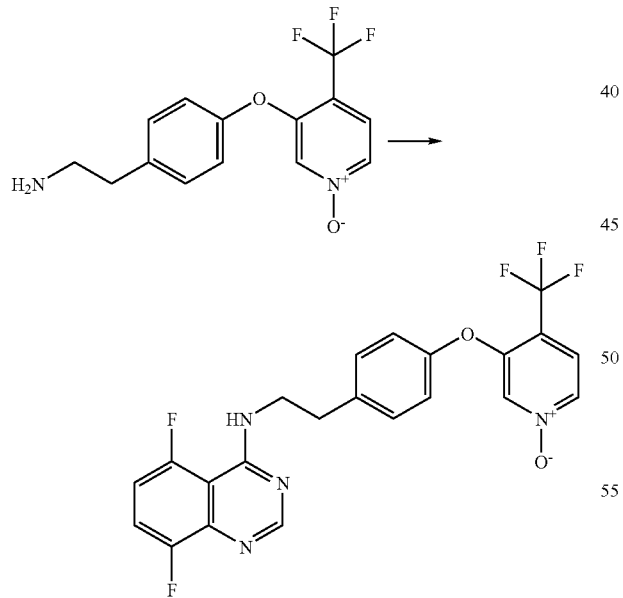

(5,8-Difluoroquinazolin-4-yl)-{2-[4-(1-oxy-4-trifluoromethylpyridin-3-yloxy)-phenyl]-ethyl}-amine A solution of 2-[4-(1-oxy-4-trifluoromethylpyridin-3-yloxy)-phenyl]-ethylamine (0.23 g, 0.77 mmol) and N'-(2-cyano-3,6-difluorophenyl)-N,N-dimethylformamidine (0.14 g) in glacial acetic acid (6 mL) was heated on a steam bath for 24 h, and then concentrated in vacuo. The residue was partitioned between water (100 mL) and EtOAc. The organic layer was filtered and then concentrated in vacuo to provide a brown gum. The gum was dissolved in $CH_2Cl_2$, and precipitated by addition of hexane while boiling off $CH_2Cl_2$. The supernatant was decanted to leave 0.16 g of (5,8-difluoroquinazolin-4-yl)-{2-[4-(1-oxy-4-trifluoromethylpyridin-3-yloxy)-phenyl]-ethyl}-amine as a tan solid, M.P. 165-170°; MS m/z 462; $^1$H NMR (400 MHz, $CDCl_3$) δ 8.70 (s, 1 H), 7.97 (d, J=6.6 Hz, 1 H), 7.77 (s, 1 H), 7.49 (d, J=6.7 Hz, 1 H), 7.39-7.31 (m, 3 H), 7.12-7.06 (m, 2 H), 7.06-6.99 (m, 1 H), 6.78-6.67 (m, 1 H), 3.99-3.90 (m, 2 H), 3.08 (t, J=6.8 Hz, 2 H).

EXAMPLE 13

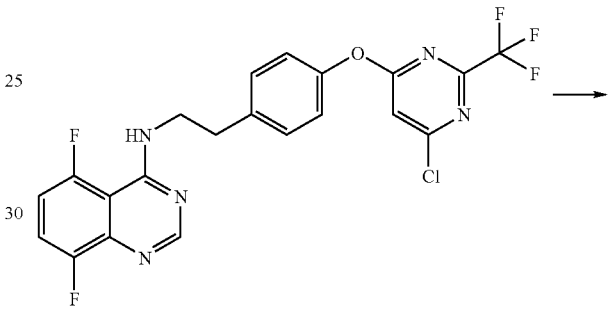

(5,8-Difluoroquinazolin-4-yl)-{2-[4-(2-trifluoromethylpyrimidin-4-yloxy)-phenyl]-ethyl}-amine A mixture of {2-[4-(6-chloro-2-trifluoromethylpyrimidin-4-yloxy)-phenyl]-ethyl}-(5,8-difluoroquinazolin-4-yl)-amine (0.205 g, 0.46 mmol), 10% Pd on activated carbon (0.030 g) and triethylamine (0.60 mL, 4.3 mmol) in EtOH (15 mL) was charged with hydrogen to an initial pressure of 40 psi in a Parr bottle and shaken overnight. The catalyst was removed by filtration on Celite and the filtrate was concentrated in vacuo. The residue was purified on silica gel to give 0.087 g (42% yield) of (5,8-difluoroquinazolin-4-yl)-{2-[4-(2-trifluoromethylpyrimidin-4-yloxy)-phenyl]-ethyl}-amine as a white foam, $^1$H NMR ($CDCl_3$): δ 8.71 (d, J=6.3 Hz, 1H), 8.69 (s, 1H), 7.32-7.40 (m, 3H), 7.16 (d, J=8.7 Hz, 2H), 6.97-7.04 (m, 2H), 6.68-6.82 (br, 1H), 3.97 (q, J=6.9 Hz, 2H), 3.08 (t, J=6.9 Hz, 2H). LC/MS: 448.18 (M++1).

PREPARATION 12

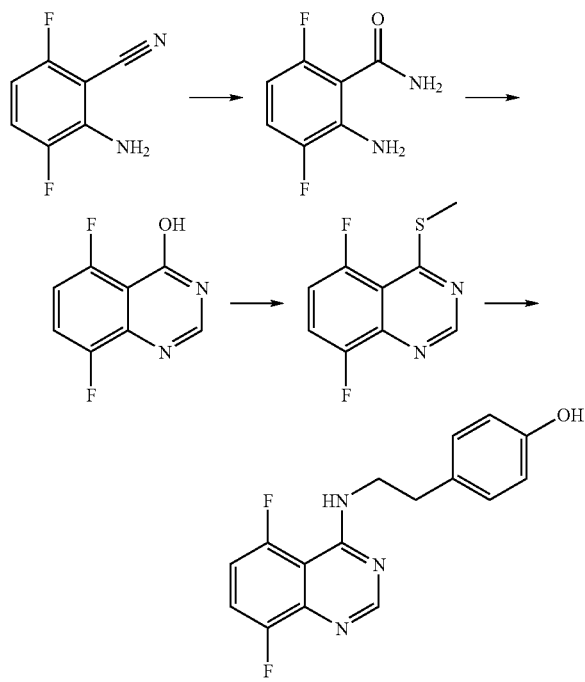

2-Amino-3,6-difluorobenzamide

2-Amino-3,6-difluorobenzonitrile (2.3 g, 15 mmol) was added to concentrated sulfuric acid (5 mL) in a 25 mL 2-necked flask equipped with a thermometer with good stirring. The temperature rose to around 40° C. and the mixture became homogeneous. The solution was heated to 70° C. for 2 hours, cooled to room temperature, poured over ice, neutralized with concentrated NH$_4$OH using water and NH$_4$OH to rinse the flask and adding ice as necessary to keep the mixture cold. The separated solid was collected by filtration, washed with water and dried to give 2-amino-3,6-difluorobenzamide, 2.2 g. A second crop of 0.24 g was collected from the cold, concentrated filtrate, 95% overall. M.P. 121-123° C., LC/MS (ESI) m/z 172, $^1$H NMR (300 MHz, d$_6$-DMSO) δ 7.70 (bs, 1H), 7.63 (bs, 1H), 7.10 (m, 1H), 6.32 (m, 1H), 6.05 (bs, 2H).

5,8-Difluoroquinazolin-4-ol

2-Amino-3,6-difluorobenzamide (2.0 g, 11.6 mmol), ammonium sulfate (0.15 g, 1.16 mmol), triethylorthoformate (4.3 g, 4.8 mL, 29.1 mmol) and acetic anhydride (3.0 g, 2.8 mL, 29.1 mmol) were combined in a 100 mL round bottomed flask and the mixture heated to 145° C. on a heating mantle, becoming nearly homogeneous around 90° C., then precipitating additional solid. After 1 h, the mixture was cooled to room temperature and diluted with water and stirred. The precipitated solids were collected by filtration, washed with water and dried to give 1.95 g of 5,8-difluoroquinazolin-4-ol as a white solid. A second crop of 0.13 g was collected from the cold concentrated filtrate, 98% overall. M.P. 257-258° C., LC/MS (ESI) m/z 182, $^1$H NMR (300 MHz, d$_6$-DMSO) δ 12.48 (bs, 1H), 8.13 (s, 1H), 7.70 (m, 1H), 7.27 (m, 1H).

5,8-Difluoro-4-thiomethylquinazoline 5,8-Difluoroquinazolin-4-ol (0.215 g, 1.18 mmol) and Ph$_3$P (0.619 g, 2.36 mmol) were weighed into an oven-dried, nitrogen-swept 100 mL round bottomed flask. Dichloroethane (5 mL) and CCl$_4$ (0.381 g, 2.48 mmol) were added via syringe and the mixture was heated at reflux under nitrogen for 2 h, then cooled to room temperature. Sodium methane thiolate (0.165 g, 2.36 mmol) was added to the colorless, homogeneous solution and the resulting mixture stirred briefly at room temperature. The crude reaction mixture was transferred directly to a silica gel column (transfer aided by a small volume rinse of the reaction flask with methylene chloride) and purified by flash chromatography (CH$_2$Cl$_2$:MeOH/ 20:1→10:1) to give 0.221 g (88%) as a pale orange solid. M.P. 117-118° C., LC/MS (ESI) m/z 212, $^1$H NMR (300 MHz, CDCl$_3$) δ 9.01 (s, 1H), 7.47 (m, 1H), 7.19 (m, 1H), 2.68 (s, 3H).

4-[2-(5,8-Difluoroquinazolin-4-ylamino)-ethyl]-phenol 5,8-Difluoro-4-thiomethylquinazoline (0.1 g, 0.47 mmol) and tyramine (0.071 g, 0.52 mmol) were weighed into a 15 mL round bottomed flask. CH$_3$CN (2 mL) was added and the resulting slurry heated to reflux under nitrogen to give a homogeneous solution. After 2 days, the reaction was cooled, treated with an additional tyramine (0.071 g, 0.52 mmol) and again heated to reflux overnight. The reaction was cooled and diluted with water and the resulting tan solid was collected by filtration and dried to give 0.11 g (77% yield) of 4-[2-(5,8-difluoroquinazolin-4-ylamino)-ethyl]-phenol as a tan solid.

PREPARATION 13

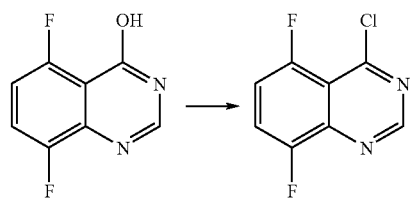

4-Chloro-5,8-difluoroquinazoline 5,8-Difluoroquinazolin-4-ol (0.25 g, 1.4 mmol) was weighed into an oven dried, nitrogen flushed 25 mL round bottomed flask. Thionyl chloride (2 mL) was added along with DMF (2 drops) and the mixture heated to reflux under nitrogen for 1 h giving a clear, yellow homogeneous solution. After cooling to room temperature, the excess SOCl$_2$ was removed from the precipitated substrate in vacuo to afford 4-chloro-5,8-difluoroquinazoline as a yellow solid, used without further purification.

Biological Testing

The following Table I shows representative compounds of formula (I), together with characterizing physical and biological data.

TABLE 1

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 1 | [structure] | 446 | *** | *** | *** | *** | + |
| 2 | [structure] | 403 | *** | *** | *** | * | + |
| 3 | [structure] | 447 | *** | *** | ** | *** | + |
| 4 | [structure] | 301 | ** | ** | * | * | − |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 5 | 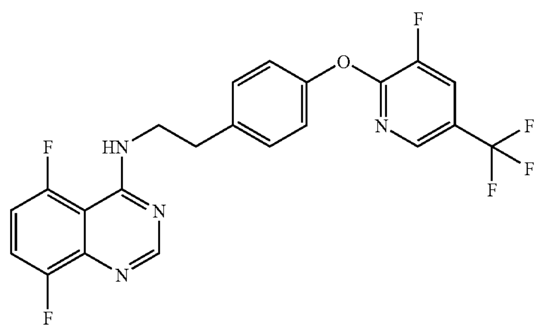 | 464 | * | * | * | *b | + |
| 6 | 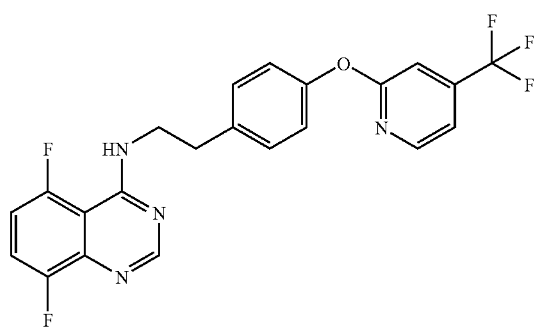 | 446 | * | * | * | * | + |
| 7 | 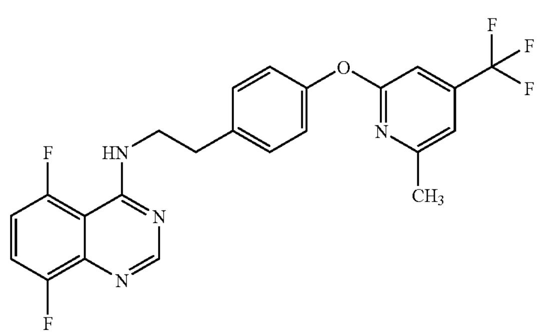 | 460 | * | * | * | * | + |
| 8 | 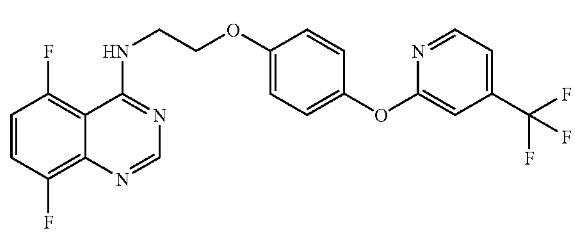 | 462 | * | * | * |  | − |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 9 | 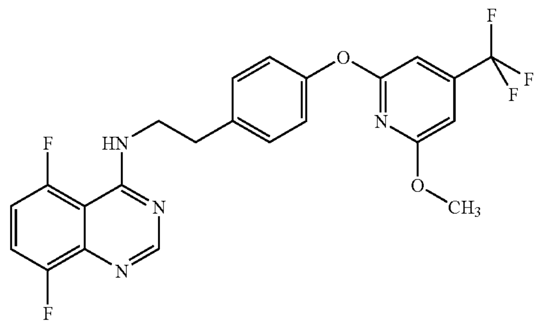 | 476 | * | * | * |  | + |
| 10 | 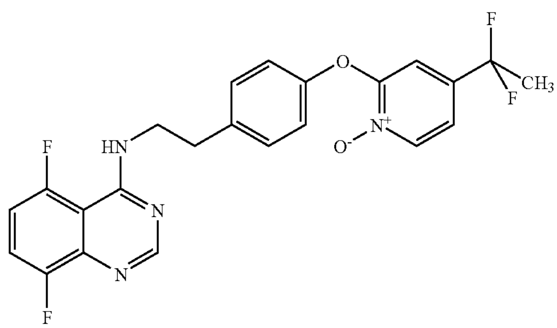 | 458 | * | * |  | * | − |
| 11 | 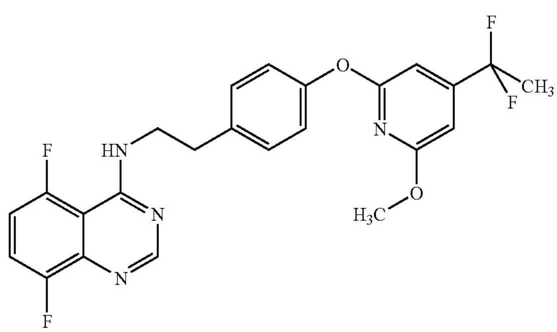 | 472 | * | * |  | * | + |
| 12 | 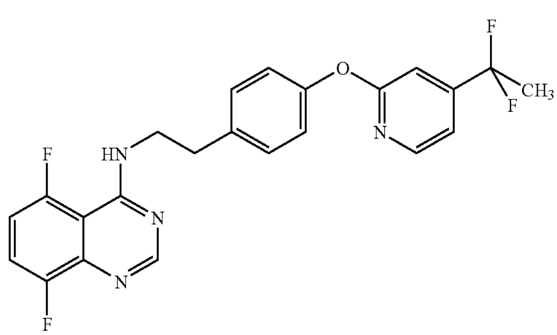 | 442 | * | * | * | * | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 13 | 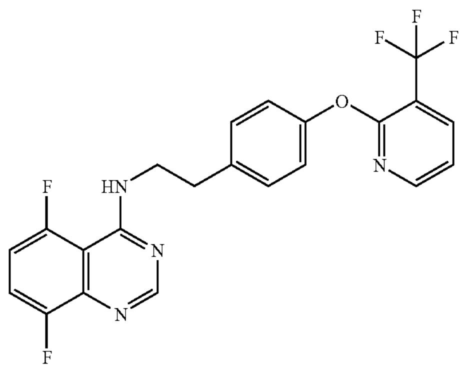 | 446 | NT | *a | NR | *b | + |
| 14 | 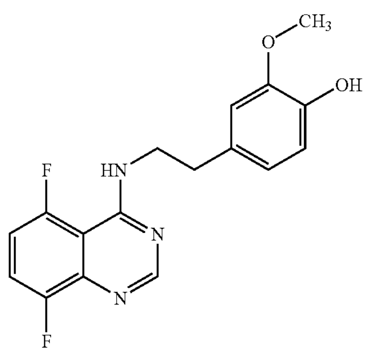 | 331 | ** | * | * | *b | − |
| 15 | 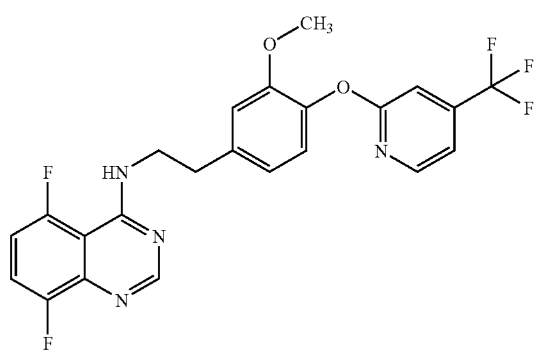 | 476 | * | * | * | * | + |
| 16 | 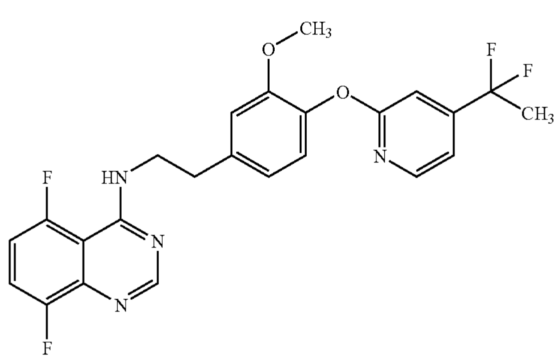 | 472 | * | * | * | * | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 17 | (structure) | 343 | *** | *** | ** | * | + |
| 18 | (structure) | 329 | * | ** | * | * | − |
| 19 | (structure) | 474 | *** | *** | *** | *** | + |
| 20 | (structure) | 343 | *** | *** | ** | ** | − |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 21 | 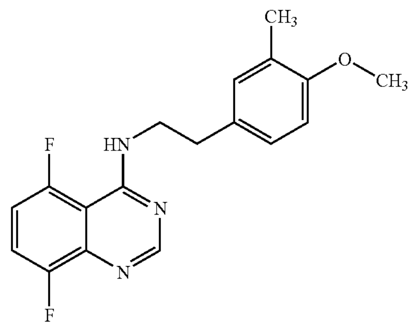 | 329 | * |  | ** | *b | − |
| 22 | 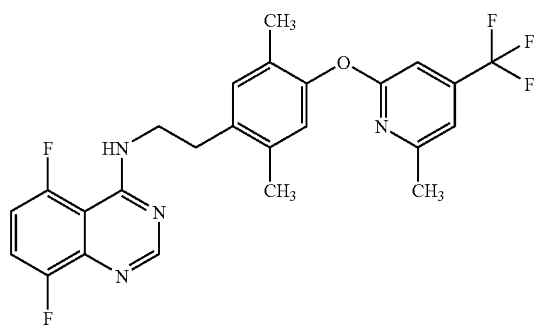 | 488 | NT | * |  | ***b | + |
| 23 | 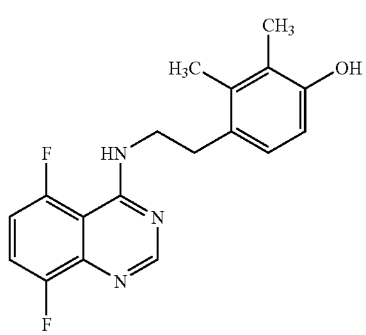 | 329 | * |  | ** | * | − |
| 24 | 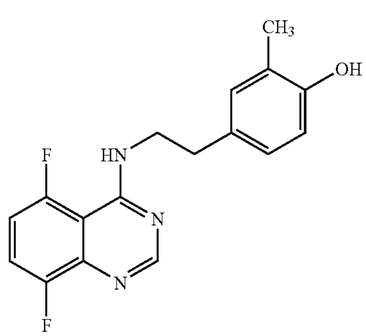 | 315 | * | * | * | * | − |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 25 | [structure] | 460 | *** | *** | *** | *** | + |
| 26 | [structure] | 474 | *** | *** | ** | *** | + |
| 27 | [structure] | 319 | * | * | * | * | − |
| 28 | [structure] | 504 | *** | *** | *** | ***b | + |

TABLE 1-continued
Examples of compounds of formula (I) including mass spectrometry results (MS; m/z), and biological activity against representative fungal diseases and insects.
| Com- pound | Structure | MS m/z | Activity against fungal diseases | | | | Activity against insects |
|---|---|---|---|---|---|---|---|
| | | | PSPECU | PUCCRT | PYRIOR | SEPTTR | |
| 29 | 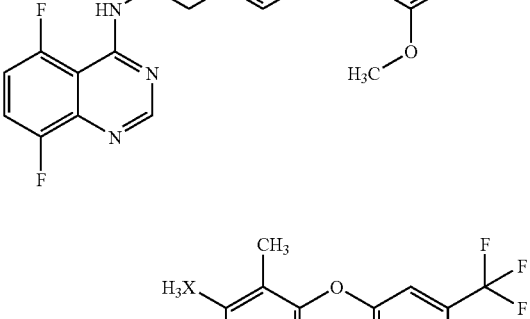 | 490 | * | * |  | * | + |
| 30 | 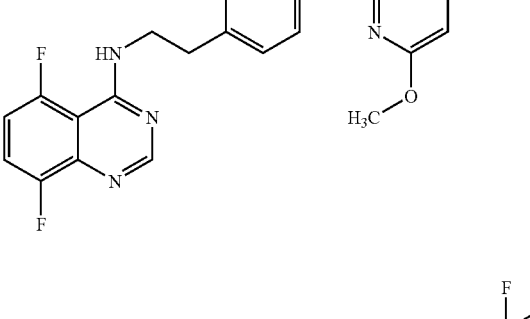 | 504 |  | * | ** | * | − |
| 31 | 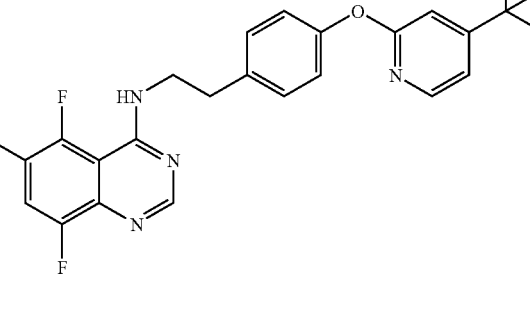 | 464 | * | * | * | * | + |
| 32 | 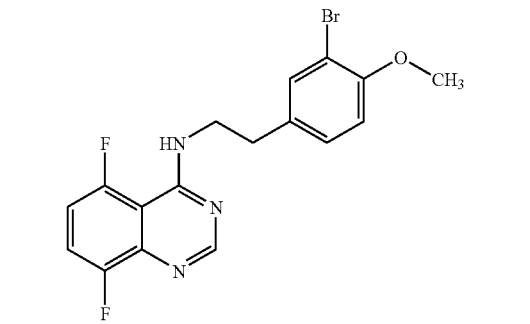 | 394 | * | * | ** | * | − |

TABLE 1-continued

Examples of compounds of formula (I) including mass spectrometry results (MS; m/z), and biological activity against representative fungal diseases and insects.

| Compound | Structure | MS m/z | PSPECU | PUCCRT | PYRIOR | SEPTTR | Activity against insects |
|---|---|---|---|---|---|---|---|
| 33 | 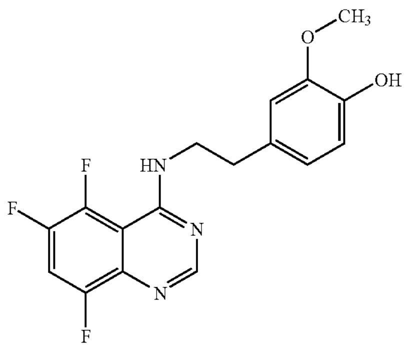 | 349 | NT | *a | NT | *b | NT |
| 34 | 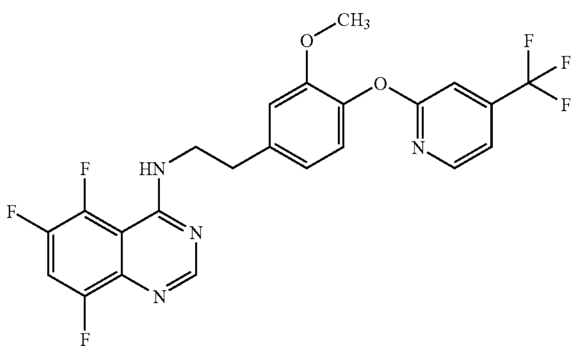 | 494 | * | * | * | * | + |
| 35 | 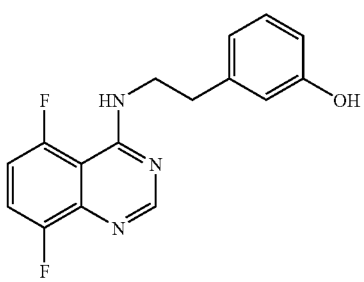 | 301 | * |  | NT | NT | − |
| 36 | 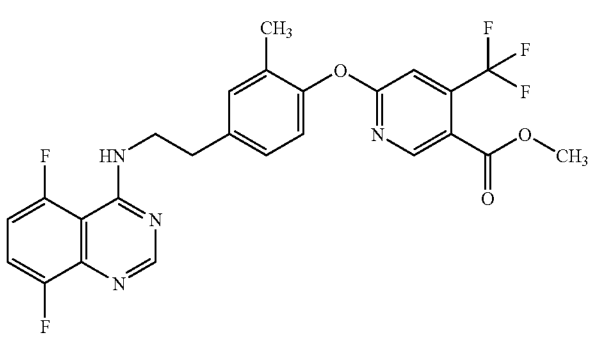 | 518 | * | * | NT | *b | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 37 | 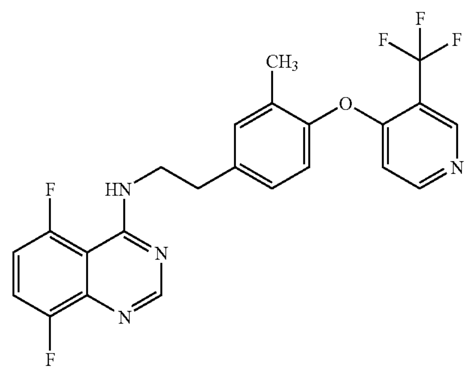 | 460 | * | * | *a | b | + |
| 38 | 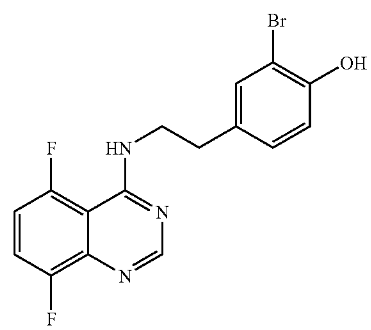 | 380 | * | * | * | NT | − |
| 39 | 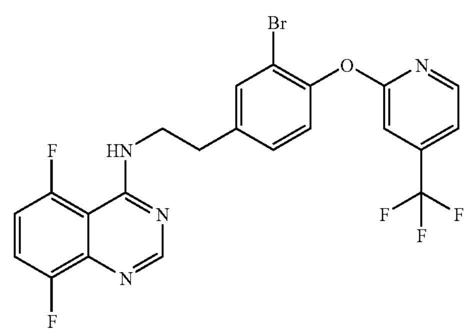 | 525 | * | * | * | *b | + |
| 40 | 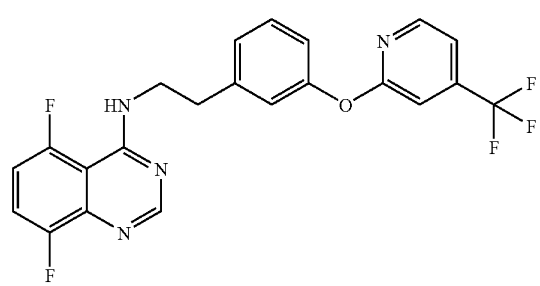 | 446 | * | * | * | b | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 41 | 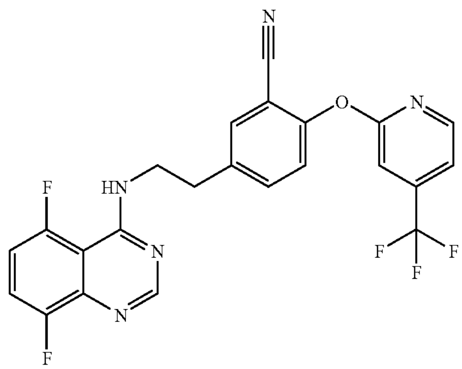 | 471 | * | * | * | b | + |
| 42 | 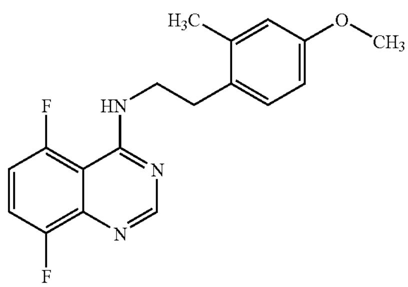 | 329 | * | * | * | * | + |
| 43 | 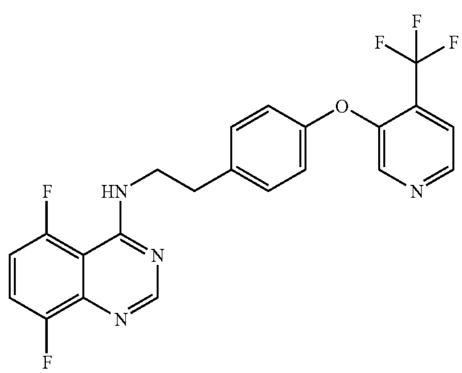 | 446 | * | * |  | * | + |
| 44 | 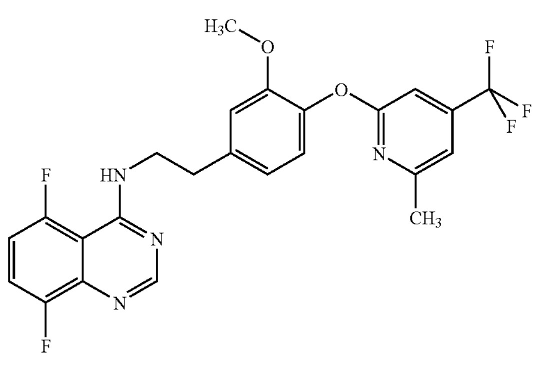 | 490 | * | * | * | *** | + |

TABLE 1-continued

Examples of compounds of formula (I) including mass spectrometry results (MS; m/z), and biological activity against representative fungal diseases and insects.

| Com-pound | Structure | MS m/z | Activity against fungal diseases | | | | Activity against insects |
|---|---|---|---|---|---|---|---|
| | | | PSPECU | PUCCRT | PYRIOR | SEPTTR | |
| 45 | 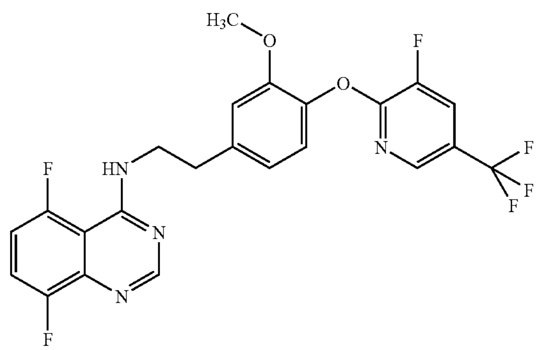 | 494 | * | * | * | *** | + |
| 46 | 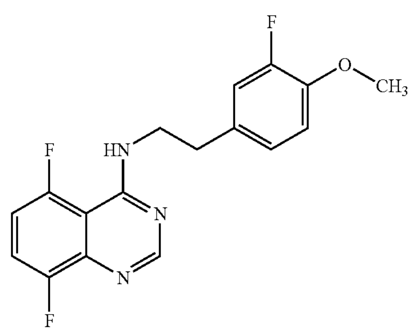 | 333 | * | * | * | * | + |
| 47 | 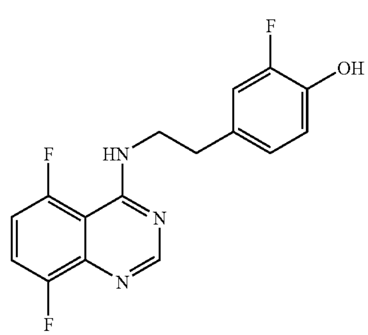 | 319 | * | * | ** | * | − |
| 48 | 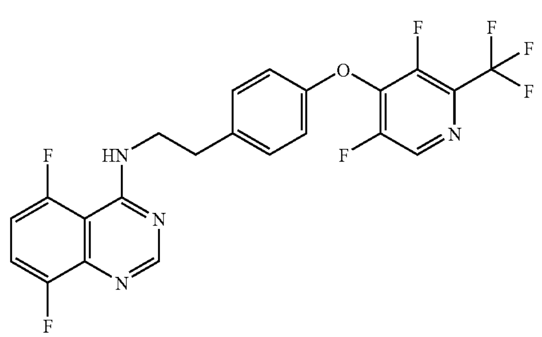 | 482 | * | * | * | * | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 49 | 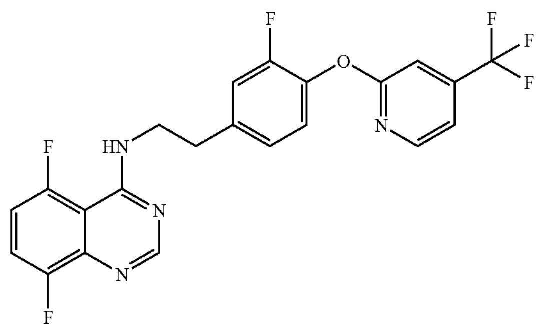 | 464 | * | * | * | * | + |
| 50 | 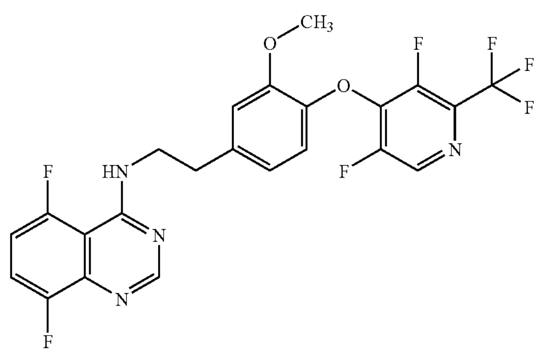 | 512 | * | * | * | * | + |
| 51 | 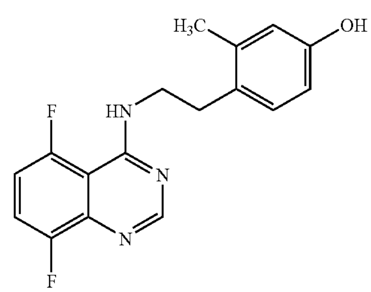 | 315 | * | * | ** | * | − |
| 52 | 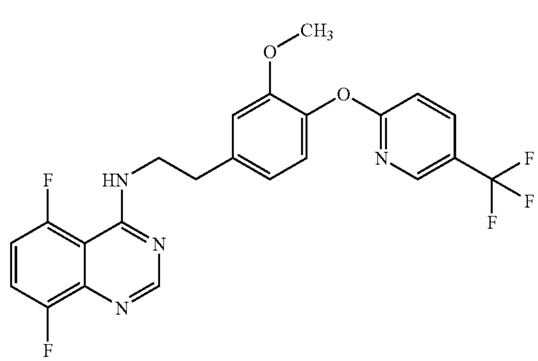 | 460 | * | * | * | * | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 53 | 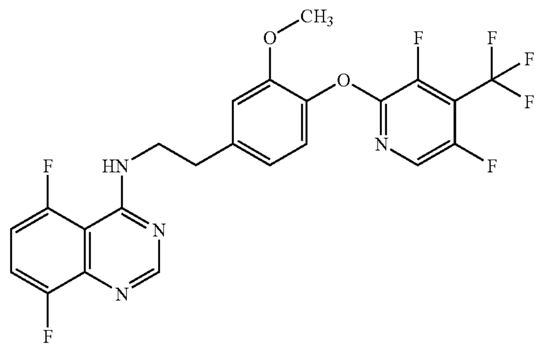 | 512 | * | * | * | * | + |
| 54 | 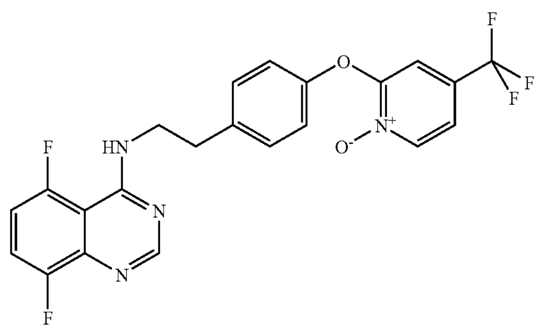 | 462 | * | * | * | * | + |
| 55 | 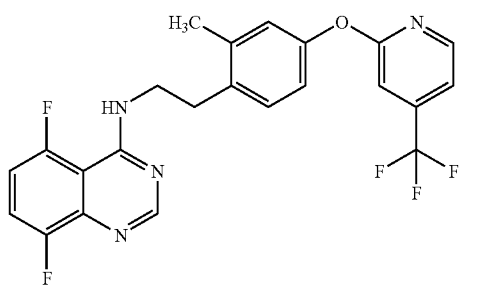 | 476 | * | * | * | * | + |
| 56 | 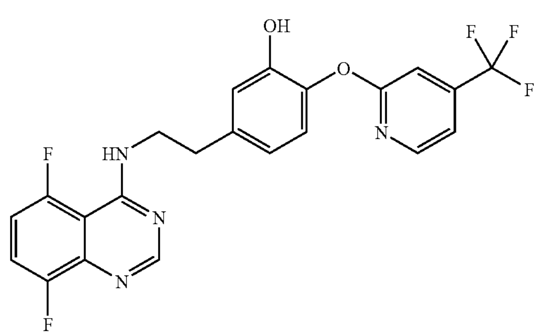 | 462 | * | * | * |  | − |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 57 | 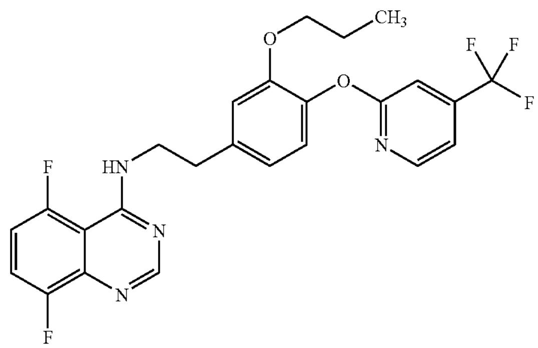 | 504 | * | * | * | * | + |
| 58 | 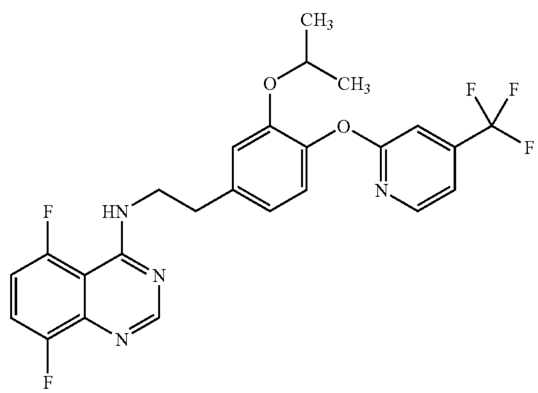 | 504 | * | * | * | * | + |
| 59 | 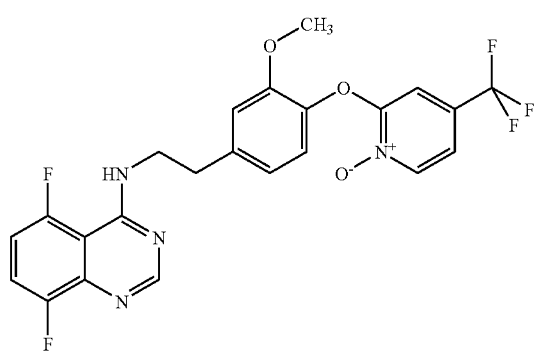 | 492 | * | * | * | * | + |
| 60 | 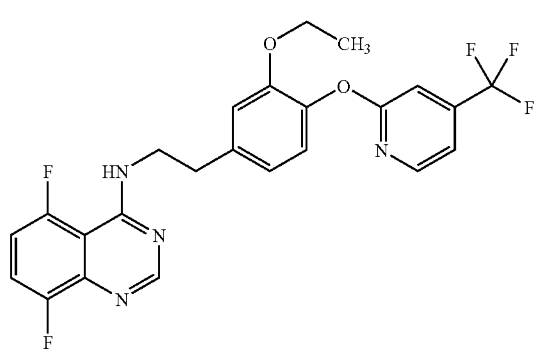 | 490 | * | * | * | * | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 61 | 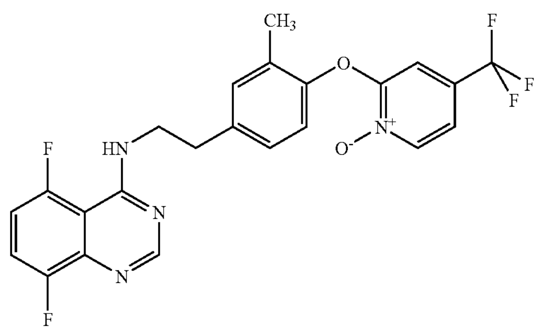 | 476 | * | * |  | * | − |
| 62 | 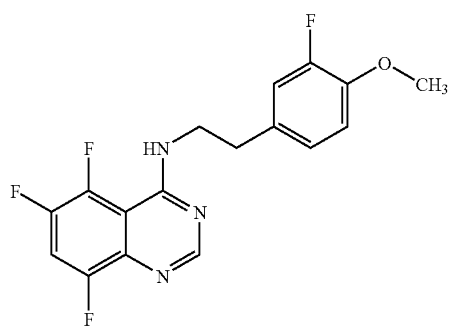 | 351 | NT | NT | NT | NT | NT |
| 63 | 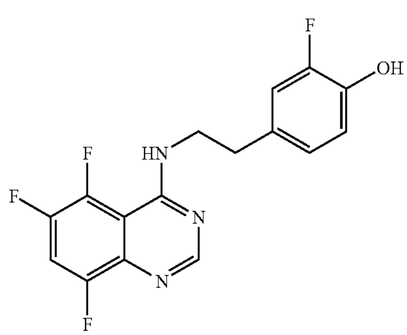 | 337 | NT | NT | NT | NT | NT |
| 64 | 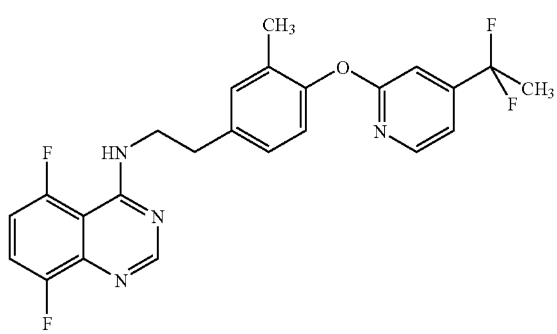 | 456 | * | * | * | * | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 65 | 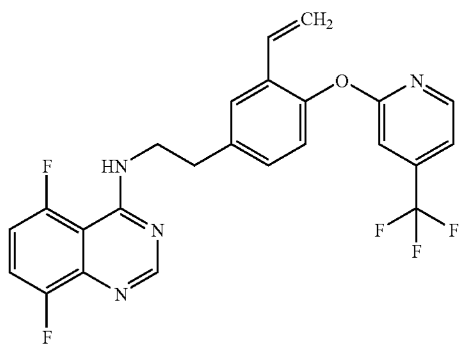 | 474 | * | * | * | * | + |
| 66 | 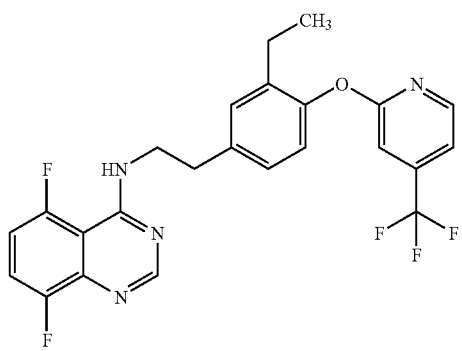 | 472 | * | * | * | * | + |
| 67 | 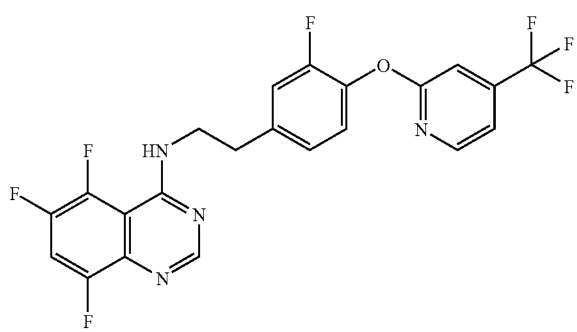 | 482 | * | * | * | * | + |
| 68 | 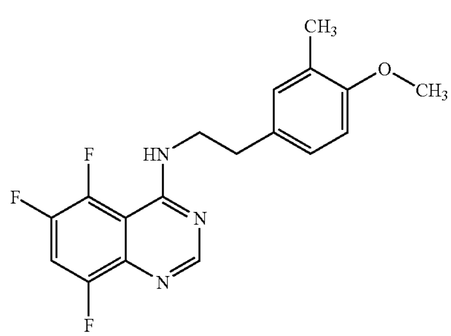 | 347 | ** | * | *** | * | − |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 69 | 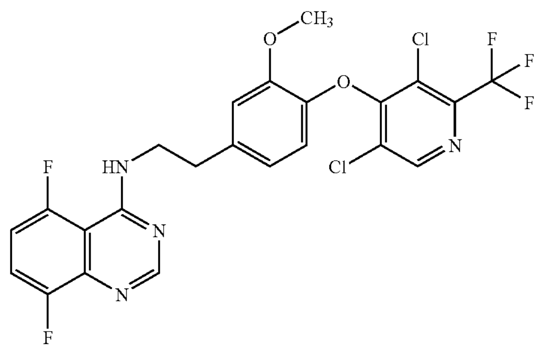 | 545 | * | * | * | * | + |
| 70 | 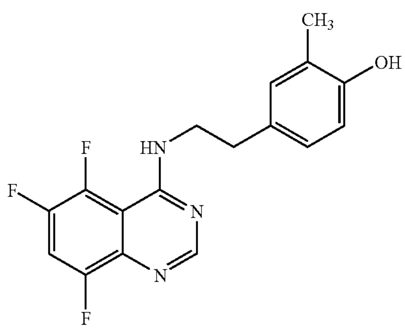 | 333 | * |  |  | ** | − |
| 71 | 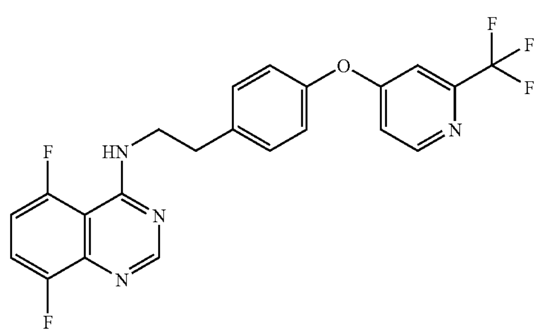 | 446 | NT | *a | NT | *b | NT |
| 72 | 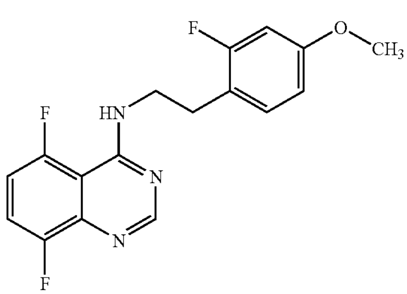 | 333 | * | * | *** | *b | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 73 | 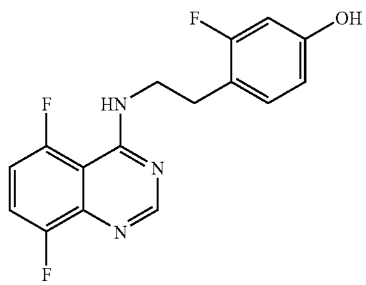 | 319 | NT | NT | NT | NT | NT |
| 74 | 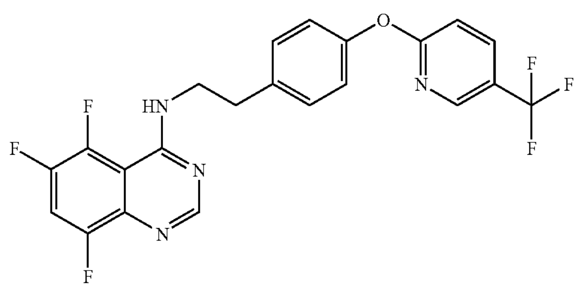 | 464 | * | * | * | * | + |
| 75 | 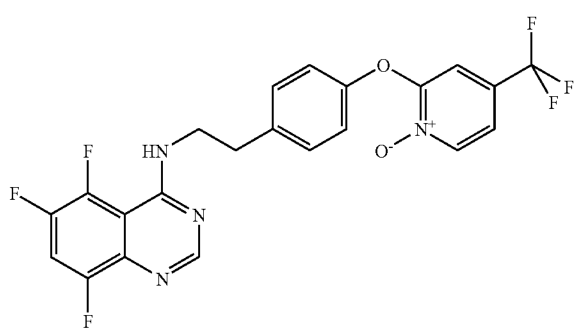 | 480 | * | * | * | * | − |
| 76 | 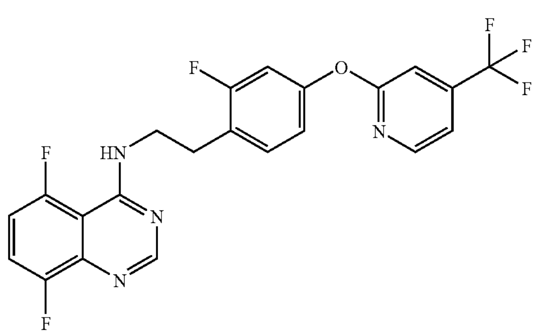 | 464 | * | * | * | * | + |

TABLE 1-continued
Examples of compounds of formula (I) including mass spectrometry results (MS; m/z), and biological activity against representative fungal diseases and insects.
| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 77 | 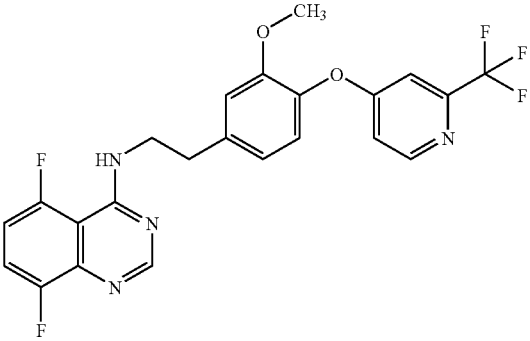 | 476 | * | * | * | * | + |
| 78 | 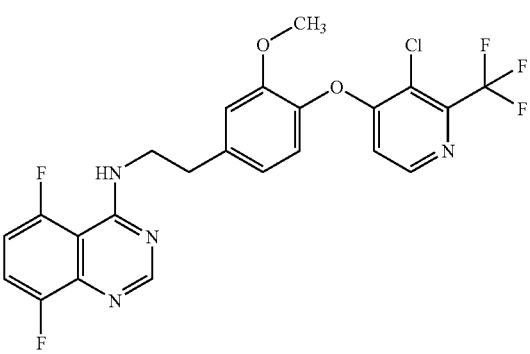 | 510 | * | * | * | * | NT |
| 79 | 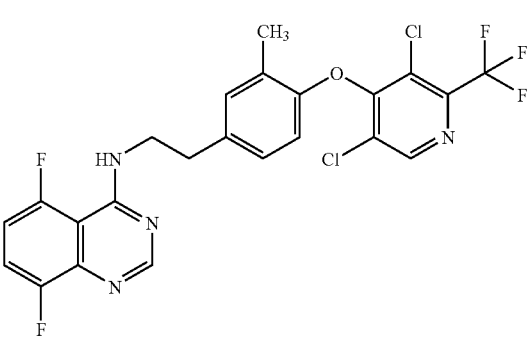 | 529 |  | * | * | * | + |
| 80 | 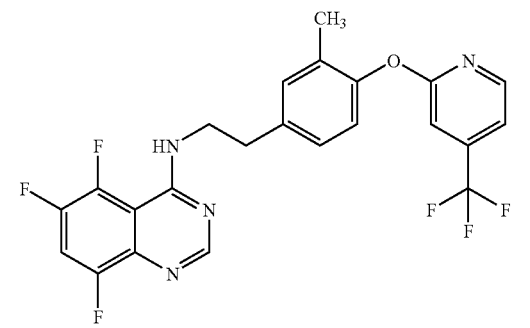 | 478 | * | * | * | * | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 81 | 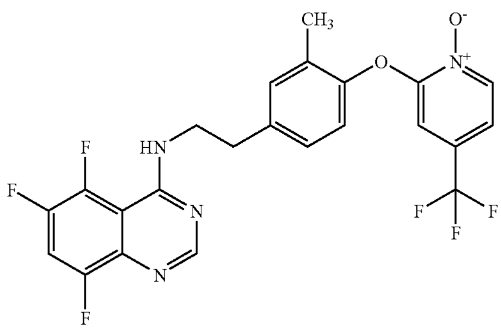 | 494 | * | * | * | * | + |
| 82 | 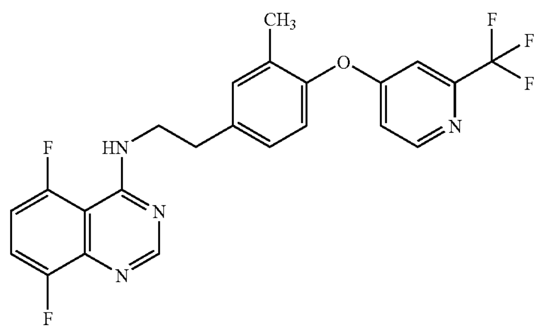 | 460 | * | * | * | * | + |
| 83 | 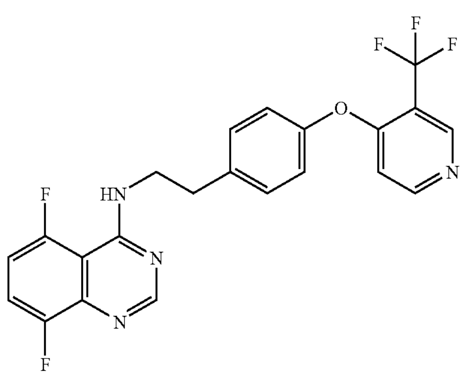 | 446 | * | * | * | * | + |
| 84 | 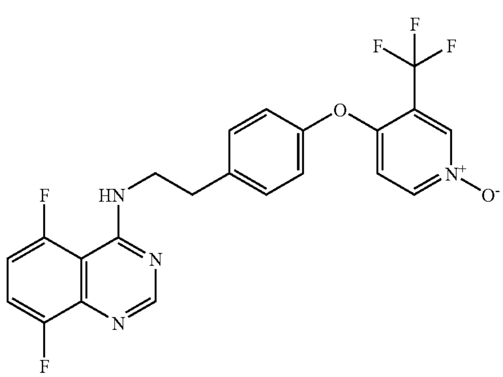 | 462 | * | * | * | * | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 85 | 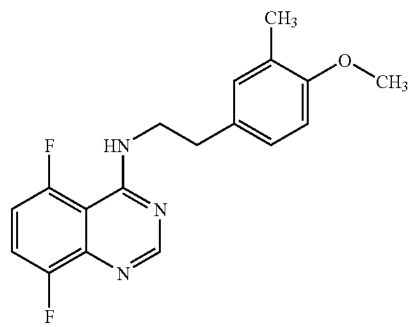 | 349 | *** | * | ** | * | — |
| 86 | 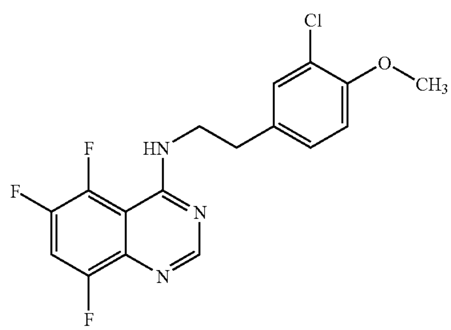 | 367 | *** | * | * | * | — |
| 87 | 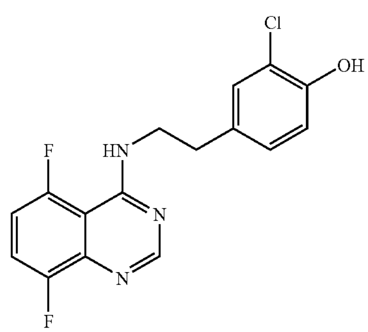 | 335 | ** | * | * | * | — |
| 88 | 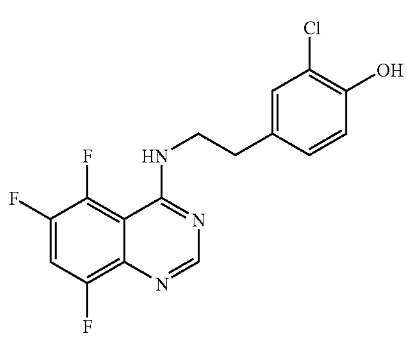 | 353 | *** | * | * | * | — |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 89 | 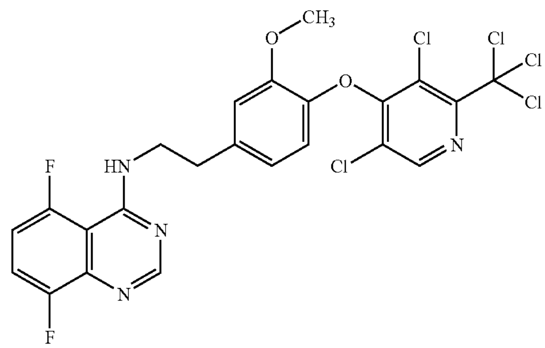 | 594 |  | * |  |  | + |
| 90 | 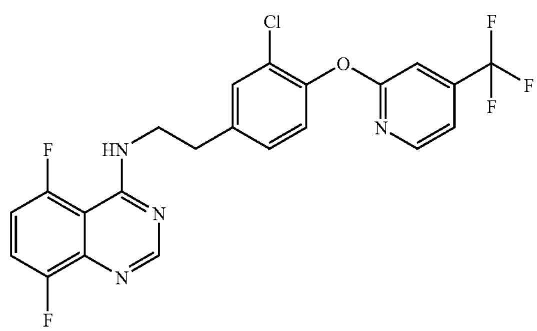 | 480 | * | * | * | * | + |
| 91 | 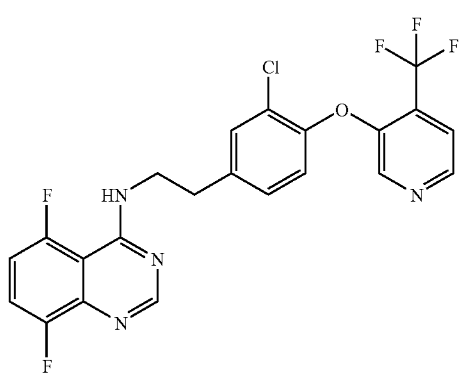 | 480 | * | * | * | * | + |
| 92 | 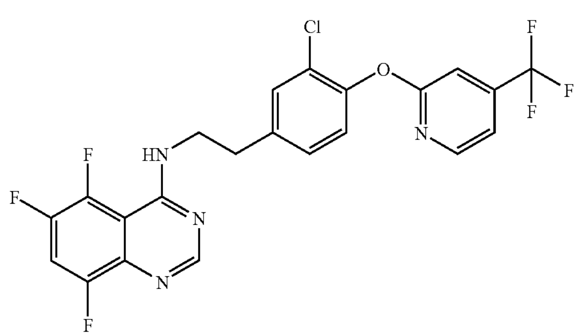 | 498 | NT |  | * | ** | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 93 | | 498 | NT | *** | *** | *** | + |
| 94 | | 285 | *** | *** | * | ** | + |
| 95 | | 515 | *** | *** | *** | *** | − |
| 96 | | 480 | *** | *** | *** | *** | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 97 | 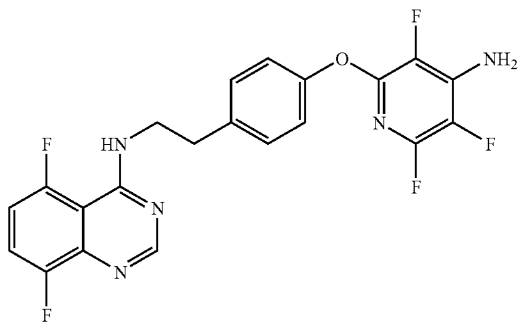 | 447 | * | * | * |  | + |
| 98 | 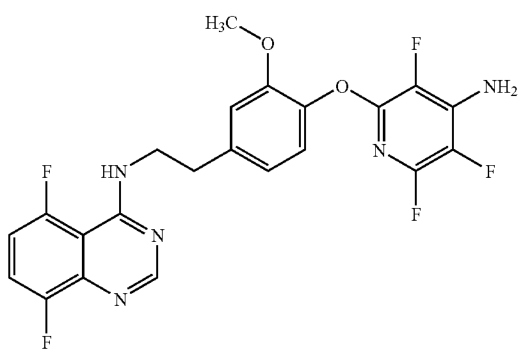 | 477 | * | * | *** | * | + |
| 99 | 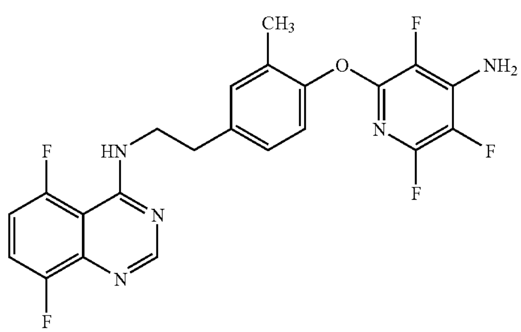 | 461 | * | * | *** | * | + |
| 100 | 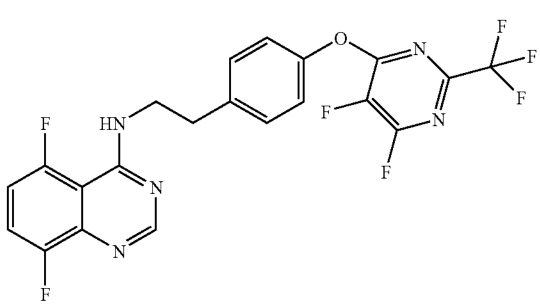 | 483 | *** | * | * | * | − |

TABLE 1-continued

Examples of compounds of formula (I) including mass spectrometry results (MS; m/z), and biological activity against representative fungal diseases and insects.

| Com-pound | Structure | MS m/z | Activity against fungal diseases | | | | Activity against insects |
|---|---|---|---|---|---|---|---|
| | | | PSPECU | PUCCRT | PYRIOR | SEPTTR | |
| 101 | 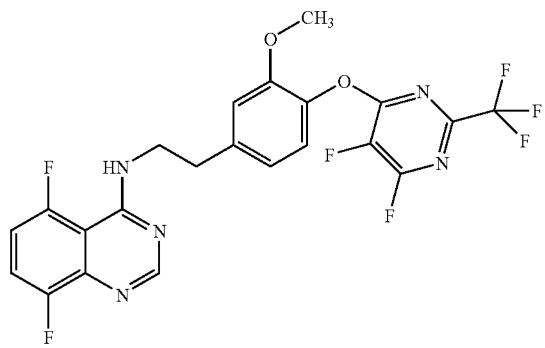 | 513 | * |  | * | * | — |
| 102 | 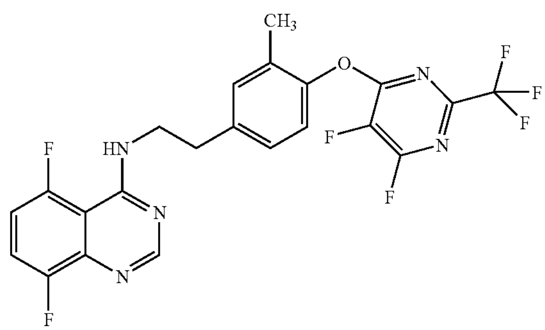 | 497 | NT | * | * | * | — |
| 103 | 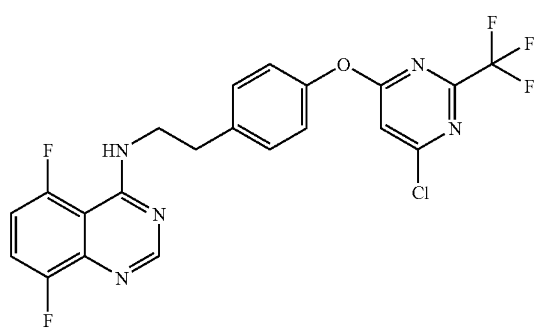 | 481 | NT | * | * | * | — |
| 104 | 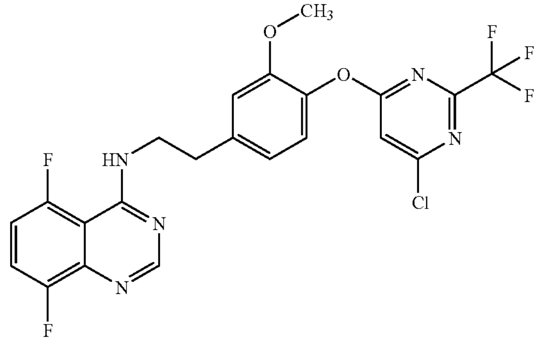 | 511 | NT | * | * | * | — |

TABLE 1-continued

Examples of compounds of formula (I) including mass spectrometry results (MS; m/z), and biological activity against representative fungal diseases and insects.

| Compound | Structure | MS m/z | Activity against fungal diseases ||||  Activity against insects |
|---|---|---|---|---|---|---|---|
| | | | PSPECU | PUCCRT | PYRIOR | SEPTTR | |
| 105 | 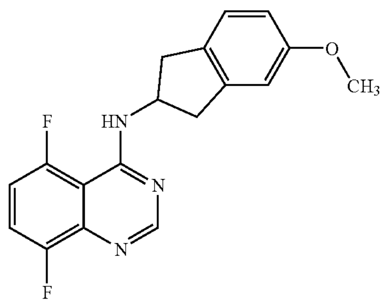 | 327 | NT | * | * | * | + |
| 106 | 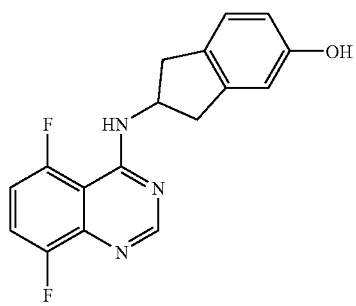 | 313 |  |  | ** | * | − |
| 107 | 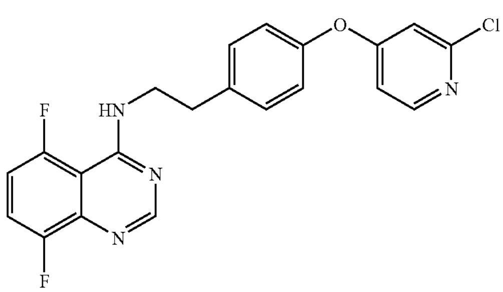 | 412 | * | * | * | *b | + |
| 108 | 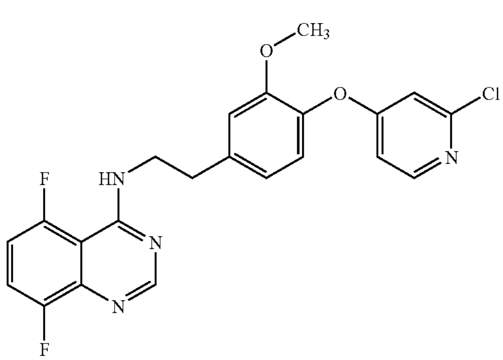 | 442 | * | *** | * | *** | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 109 | 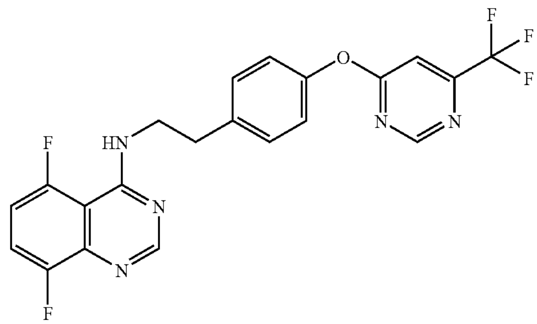 | 447 | NT | * | * | *** | + |
| 110 | 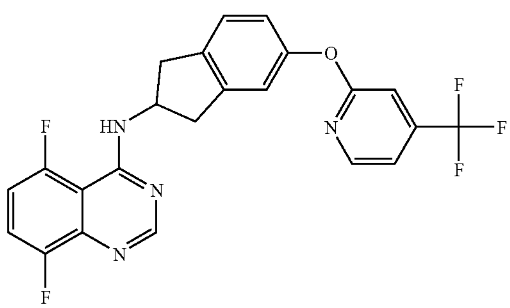 | 458 | * | * | * | * | + |
| 111 | 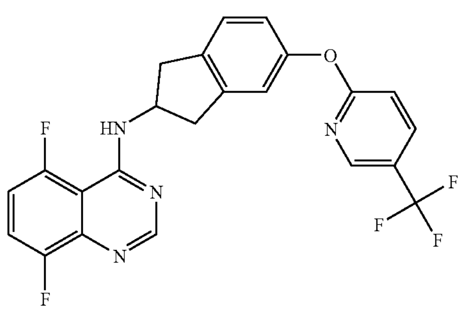 | 458 | * | * | * | * | + |
| 112 | 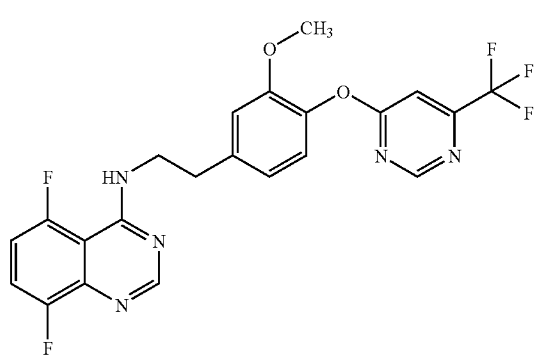 | 477 | * | * | * | *b | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 113 | 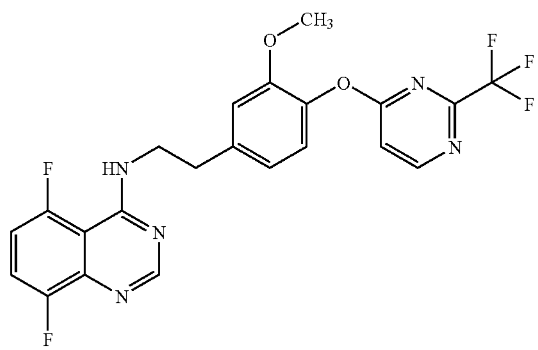 | 477 | * | * | * | *b | + |
| 114 | 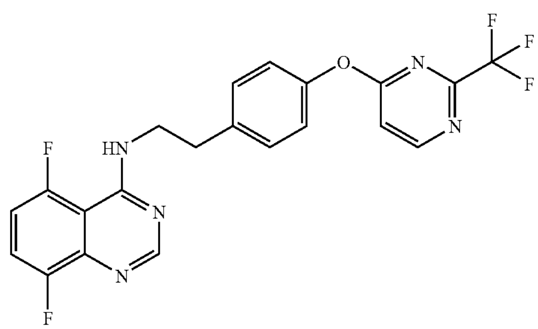 | 447 | * | * | * | b | + |
| 115 | 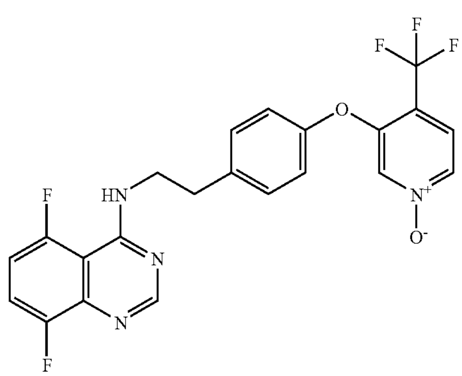 | 462 | * | * | * | * | + |
| 116 | 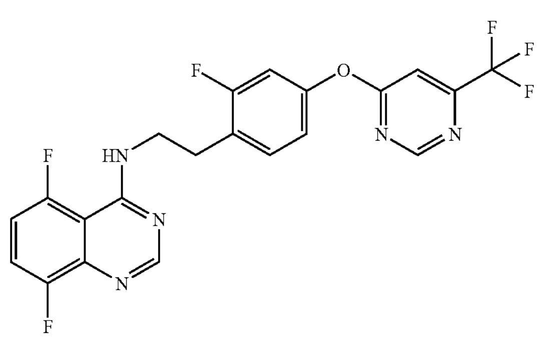 | 465 | * | * | * | *b | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 117 | 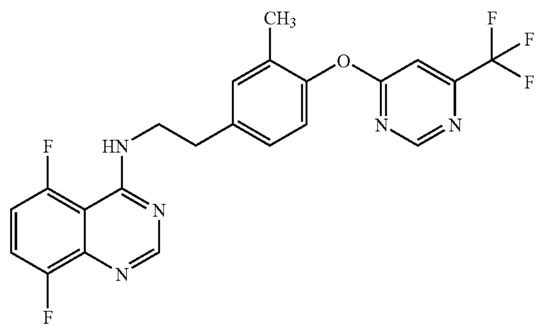 | 461 | * | * | * | *b | + |
| 118 | 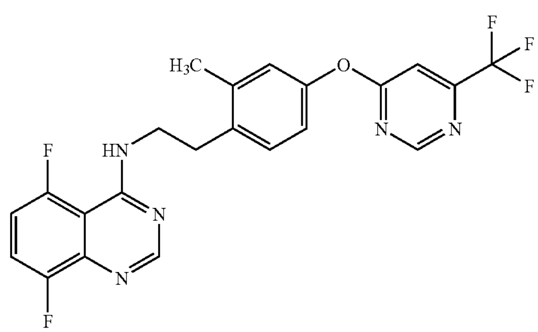 | 461 | * | * | * | *b | + |
| 119 | 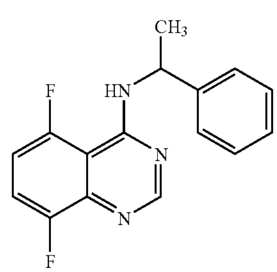 | 285 | * | * | * | * | − |
| 120 | 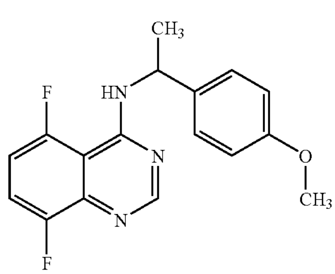 | 315 | NT | *** | NT | * | − |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 121 | 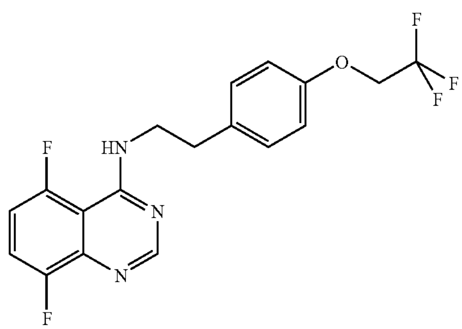 | 384 | NT | *a | NT | **b | + |
| 122 | 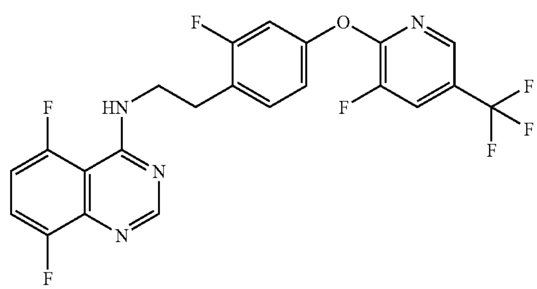 | 482 | * | * |  | *b | + |
| 123 | 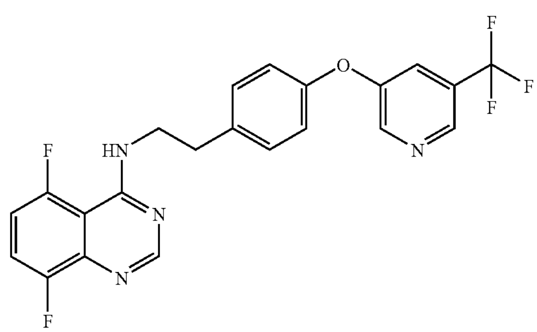 | 446 | NT | *a | NT | *b | NT |
| 124 | 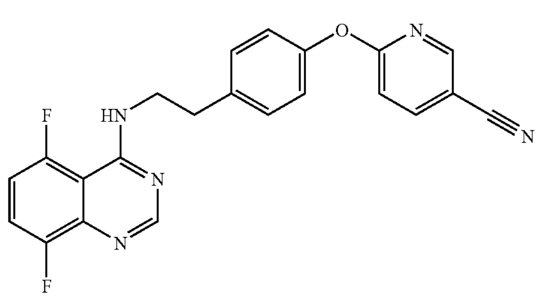 | 429 | * | * | * | b | + |

TABLE 1-continued
Examples of compounds of formula (I) including mass spectrometry results (MS; m/z), and biological activity against representative fungal diseases and insects.
| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 125 | 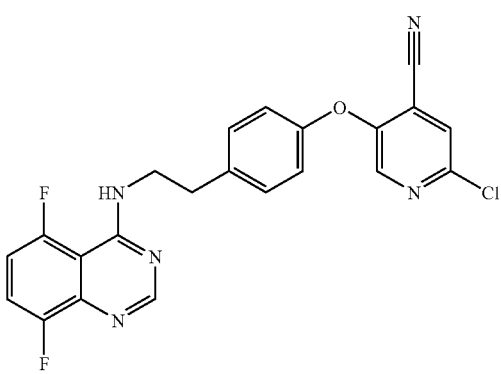 | 437 | * | * | * | * | + |
| 126 | 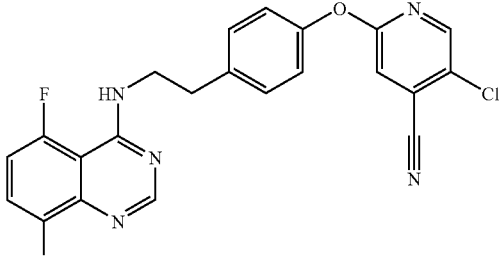 | 437 | * | * | * | *b | + |
| 127 | 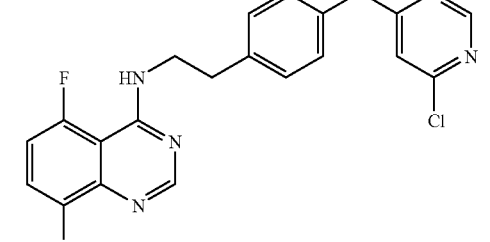 | 413 | * | * | *** | * | + |
| 128 | 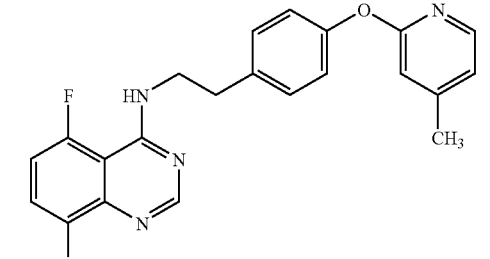 | 392 | NT | *a | NT | b | NT |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 129 | 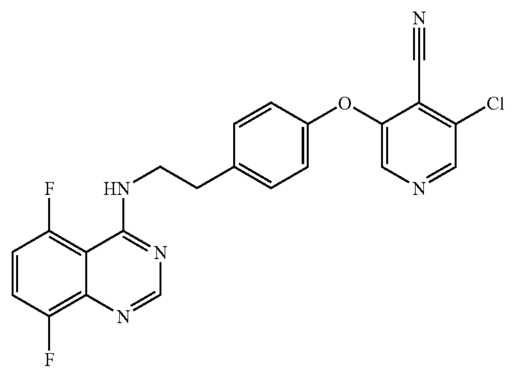 | 437 | * | * | * |  | − |
| 130 | 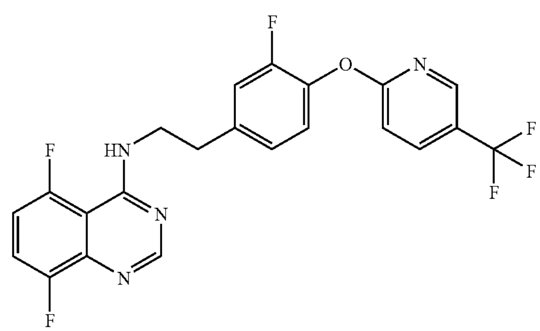 | 464 | * | * | * | * | + |
| 131 | 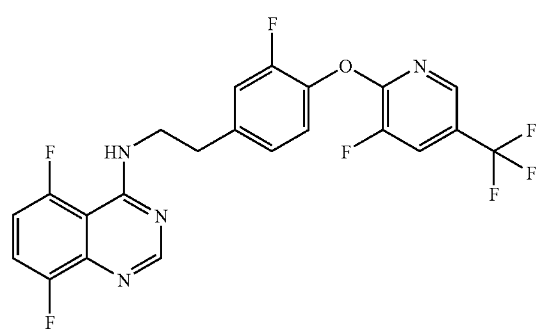 | 482 | * | * | * | * | + |
| 132 | 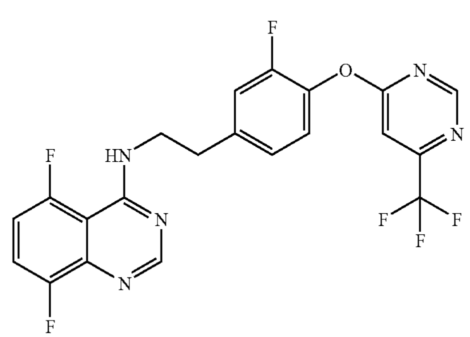 | 465 | * | * | * | * | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 133 | 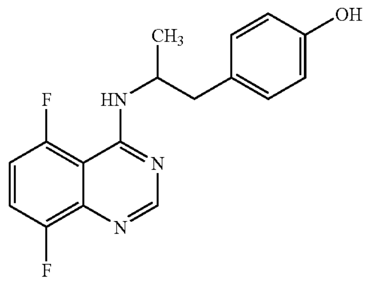 | 315 | NT | NT | NT | NT | NT |
| 134 | 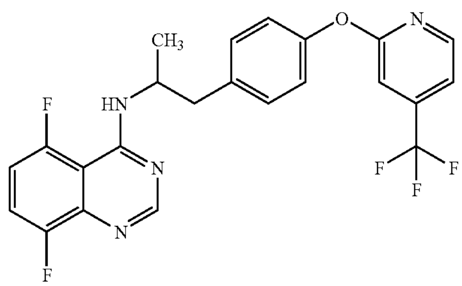 | 460 | NT | *a | NT | *b | + |
| 135 | 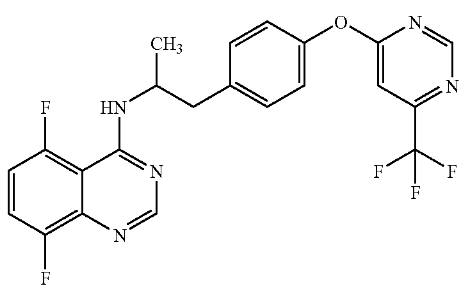 | 461 | NT | *a | NT | *b | + |
| 136 | 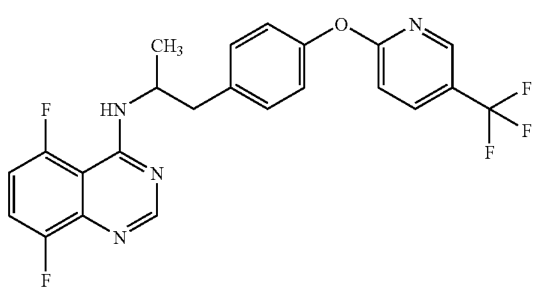 | 460 | NT | *a | NT | *b | + |
| 137 | 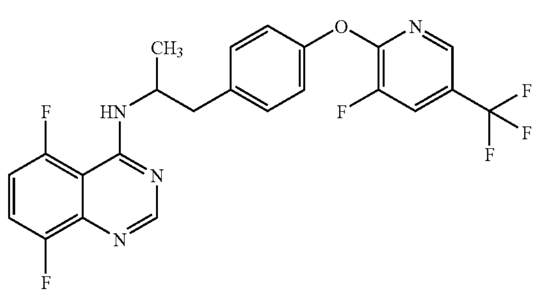 | 478 | NT | a | NT | *b | + |

TABLE 1-continued

Examples of compounds of formula (I) including mass spectrometry results (MS; m/z), and biological activity against representative fungal diseases and insects.

| Compound | Structure | MS m/z | Activity against fungal diseases | | | | Activity against insects |
|---|---|---|---|---|---|---|---|
| | | | PSPECU | PUCCRT | PYRIOR | SEPTTR | |
| 138 | 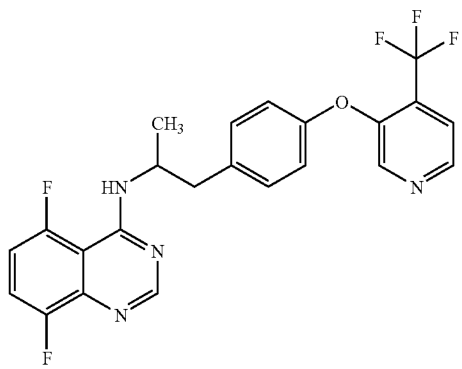 | 460 | NT | *a | NT | *b | + |
| 139 | 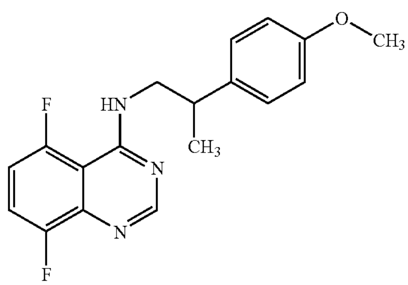 | 329 | NT | *a | NT | *b | − |
| 140 | 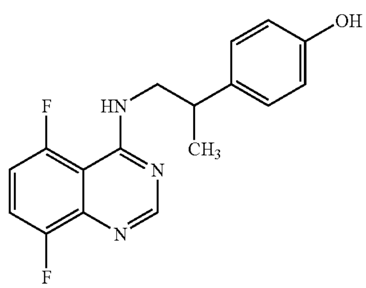 | 315 | NT | NT | NT | NT | − |
| 141 | 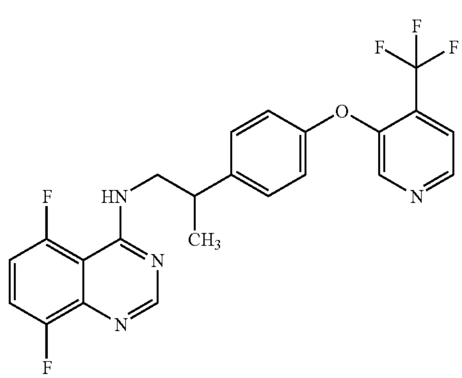 | 460 | NT | *a | NT | *b | + |

TABLE 1-continued

Examples of compounds of formula (I) including mass spectrometry results (MS; m/z), and biological activity against representative fungal diseases and insects.

| Compound | Structure | MS m/z | Activity against fungal diseases ||||  Activity against insects |
|---|---|---|---|---|---|---|---|
| | | | PSPECU | PUCCRT | PYRIOR | SEPTTR | |
| 142 | 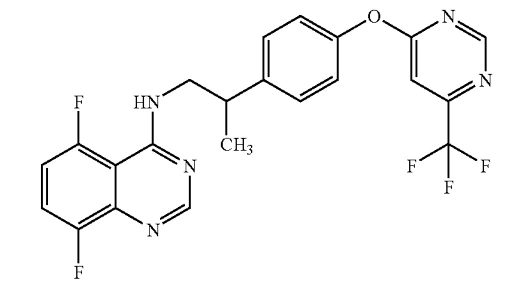 | 461 | NT | *a | NT | *b | + |
| 143 | 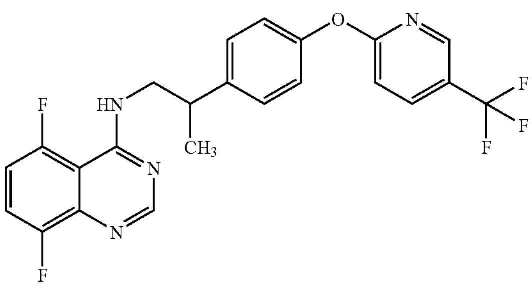 | 460 | NT | *a | NT | ***b | + |
| 144 | 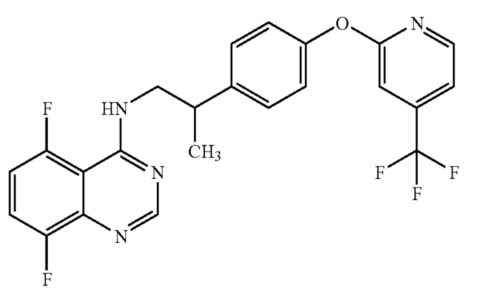 | 460 | NT | *a | NT | *b | + |
| 145 | | 478 | NT | *a | NT | **b | + | a = Tested at 3 ppm
b = Tested at 25 ppm
NT = Not tested

Fungicide activity data are the level (in percent) at which the given disease was controlled when the given compound was applied to the foliage of the plants at 200 ppm. In a few cases (noted in the table) the compound was applied to the plants at 25 ppm or 3 ppm. The plants were inoculated with the fungus one day after treatment. *=80-100% control; =50-79% control; *=0-49% control.

Insect activity data; if any species was controlled at 80% or more, the compound was considered active. "+" indicates activity; "−" indicates lack of activity.

Fungicidal Activity

The compounds of the present invention have been found to have significant fungicidal effect, particularly for agricultural use. Many of the compounds are particularly effective for use with agricultural crops and horticultural plants. In particular, the compounds effectively control a variety of undesirable fungi that infect useful plant crops. Activity has been demonstrated for a variety of fungi, including for example the following representative fungi species: Downy Mildew of Cucumber (*Pseudoperonospora cubensis*—

PSPECU), Rice Blast (*Magnaporthe grisea*-PYRIOR), Brown Rust of Wheat (*Puccinia recondita tritici*—PUCCRT); *Septoria* Blotch of Wheat (*Septoria tritici*—SEPTTR).

It will be understood by those in the art that the efficacy of the compounds against the foregoing fungi establishes the general utility of the compounds as fungicides. The activity of the compounds as effective fungicides was determined by applying the compounds to plants and observing control of fungal disease. The compounds were formulated at 200 ppm in 10 vol. % acetone plus 90 vol. % Triton X water (deionized water 99.99 wt %+0.01 wt % Triton X100), giving a "formulated test compound." In a few cases, compounds were formulated at 25 or 3 ppm rather than 200 ppm in 10 vol. % acetone plus 90 vol. % Triton X water (deionized water 99.99 wt. %+0.01 wt. % Triton X100), giving a "formulated test compound." Formulated test compounds were applied to plants using a turn table sprayer fitted with two opposing air atomization nozzles which delivered approximately 1500 L/ha of spray volume.

All plants were inoculated with spores of the fungus the day after treatment, then incubated in an environment conducive to disease development. Disease severity was evaluated 4 to 25 days later, depending on the speed of disease development. The following experiments were performed in the laboratory to determine the fungicidal efficacy of the compounds of the invention.

Leaf Rust of Wheat (causal agent *Puccinia recondita tritici=Puccinia triticina*; Bayer code PUCCRT): Wheat plants (variety 'Yuma') were grown from seed in a soil-less peat-based potting mixture (Metromix) until the seedlings had a fully expanded first leaf. Each pot contained 3-8 seedlings. These plants were sprayed until wet with the formulated test compounds. On the following day, the leaves were inoculated with an aqueous spore suspension of *Puccinia recondita tritici* and the plants were kept in high humidity overnight to permit spores to germinate and infect the leaf. The plants were then transferred to a greenhouse until disease developed on untreated control plants.

Cucumber Downy Mildew (causal agent *Pseudoperonospora cubensis*; Bayer code PSPECU): Cucumber plants (variety "Bush Champion' or 'Bush Pickle Hybrid') were grown from seed in a soil-less peat-based potting mixture (Metromix) until the first true leaf was 20-80% expanded. Each pot contained 1 seedling. These plants were sprayed until wet with the formulated test compound. On the following day, the leaves were inoculated with an aqueous suspension of downy mildew sporangia and the plants were kept in high humidity for one day to permit sporangia to germinate and infect the leaf. The plants were then incubated in a growth chamber until disease developed on untreated control plants.

Rice Blast (causal agent *Magnaporthe grisea=Pyricularia oryzae*; Bayer code PYRIOR): Rice plants (variety 'M202') were grown from seed in a soil-less peat-based potting mixture (Metromix) until the seedlings had a partly to fully expanded second leaf. Each pot contained 5-20 seedlings. These plants were sprayed until wet with the formulated test compound. On the following day, the leaves were inoculated with an aqueous spore suspension of *Pyricularia oryzae* and the plants were kept in high humidity overnight to permit spores to germinate and infect the leaf. The plants were then transferred to a growth chamber until disease developed on untreated control plants.

*Septoria* Blotch of Wheat (causal agent *Septoria tritici*; Bayer code SEPTTR): Wheat plants (variety 'Yuma') were grown from seed in a 50% pasteurized soil/50% soil-less mix until the seedlings had a fully expanded first leaf. Each pot contained 3-10 seedlings. These plants were sprayed until wet with the formulated test compound. On the following day, the leaves were inoculated with an aqueous spore suspension of *Septoria tritici* and the plants were kept in high humidity (one day in a dark dew chamber followed by three days in a lighted dew chamber) to permit spores to germinate and infect the leaf. The plants were then transferred to a greenhouse until disease developed on untreated control plants.

Table 1 presents the activity of typical compounds of the present invention when evaluated in these experiments. The effectiveness of the test compounds at controlling disease when sprayed on leaves was determined by assessing the severity of disease on treated plants, then converting the severity to percent control based on the level of disease on untreated, inoculated plants.

Insecticidal Activity

The compounds of the present invention have been found to have insecticidal activity. Activity may be demonstrated for a variety of insects, including for example the following representative insect species: Beet Armyworm (*Spodoptera exigua*—LAPHEG); Mosquito (*Aedes aegypti*—AEDSAE), Fruit Fly (*Drosophila melanogaster*—DROSME), and Colorado Potato Beetle (*Leptinotarsa decemlineata*—LPTNDE). It will be understood by those in the art that the efficacy of the compounds against the foregoing insects establishes the general utility of the compounds as insecticides.

The activity of the compounds as effective insecticides was determined by applying the compounds to diet or water, placing insects in the water or on the diet, and observing mortality after an appropriate incubation time. The compounds were formulated at 4000 ppm in DMSO giving a "formulated test compound." Formulated test compounds were diluted in 96-well plates with acetone:water solutions and applied to species-specific diet or water. The plates were infested and evaluated as described below. Results were averaged over 2-6 replications.

DROSME: Formulated test compounds were applied to microtiter plates containing fruit fly agar (10% sugar/water) to give a dose of 80 μg test compound/well. Plates were infested by placing at least three flies in each well and sealing the plate. Mortality was evaluated after incubation for two days at room temperature.

AEDSAE: Plates containing formulated test compounds at 6 μg per well were diluted with water containing mosquito larvae. Each well contained at least two larvae. Mortality was evaluated after incubation for three days at room temperature.

LAPHEG: Formulated test compounds were applied to 96-well plates containing Lepidoptera diet at 12 μg per well. Plates were infested by placing at least four fresh armyworm eggs in each well and sealing the plate with cotton batting and plastic. Mortality was evaluated after incubation for seven days at 28° C.

LPTNDE: Formulated test compounds were diluted and sprayed onto leaves of tomato plants. When dry, plant foliage was removed from the plant and placed in 8-well agar trays. Five L2 Colorado potato beetle larvae were placed in each well, and the trays were sealed and incubated at 26° C. Mortality was evaluated after three days.

Table 1 presents the activity of typical compounds of the present invention when evaluated in these experiments. The effectiveness of the test compounds at controlling insects was determined by assessing the mortality in treated test plates, then converting the average mortality to percent control. If any of the three species DROSME, AEDSAE, or LAPHEG was controlled at 80% or more, the compound was considered active (shown as "+" in Table 1). If no species was controlled at 80% or more, the compound was considered inactive (shown as "−" in Table 1).

Synergy Activity

The compound was evaluated in mixtures with pyraclostrobin, or epoxiconazole for protectant and curative activity against wheat leaf rust (*Puccinia triticina*, PUCCRT), and *Septoria* blotch (*Septoria tritici*, SEPTTR). Synergistic interactions were observed for the tested fungicides against wheat leaf rust and *Septoria* blotch in both curative and protectant evaluations in the greenhouse.

The compound was formulated at six rates (8.1, 2.7, 0.9, 0.3, 0.1, 0.03 ppm) and applied to wheat plants alone and in all combinations of it with pyraclostrobin or epoxiconazole using the methods described in section "Fungicidal Activity" above. Plants were inoculated three days before treatment (3DC) or one day after treatment (1DP), incubated in a greenhouse until disease was expressed, and visually rated (reported as % DC Obs) as described above. The expected control was calculated using the Colby equation (Colby, S. R. Calculation of the synergistic and antagonistic response of herbicide combinations. *Weeds* 1967 15, 20-22.).

The following equation was used to calculate the expected activity of mixtures containing two active ingredients, A and B:

Expected=$A+B-(A\times B/100)$

A=observed efficacy of active ingredient A at the same concentration as used in the mixture B=observed efficacy of active ingredient B at the same concentration as used in the mixture Results are shown in Tables 2 and 3. In both protectant and curative applications, the experimental compound had synergistic activity with pyraclostrobin and epoxiconazole against both wheat leaf rust and wheat leaf blotch.

TABLE 2

Synergistic control of Septoria blotch (SEPTTR) by the compound and pyraclostrobin or epoxiconazole. Expected disease control (% DC Exp) was calculated using the Colby equation.

| Compound | Rate (ppm) | | | % DC Obs | % DC Exp |
|---|---|---|---|---|---|
| | Compound | Pyraclostrobin | Epoxiconazole | | |
| 1DP SEPTTR | | | | | |
| 15 | 2.7 | | | 31 | |
| pyraclostrobin alone | | 0.3 | | 49 | |
| epoxiconazole alone | | | 0.3 | 36 | |
| 15 + pyraclostrobin | 2.7 | 0.3 | | 93 | 65 |
| 15 + epoxiconazole | 2.7 | | 0.3 | 93 | 56 |
| 3DC SEPTTR | | | | | |
| 15 | 0.9 | | | 22 | |
| pyraclostrobin alone | | 0.1 | | 14 | |
| epoxyconazole alone | | | 0.3 | 35 | |
| 15 + pyraclostrobin | 0.9 | 0.1 | | 69 | 34 |
| 15 + epoxiconazole | 0.9 | | 0.3 | 91 | 49 |

TABLE 3

Synergistic control of wheat leaf rust (PUCCRT) by the experimental compound and pyraclostrobin or epoxiconazole. Expected disease control (% DC Exp) was calculated using the Colby equation.

| Compound | Rate (ppm) | | | % DC Obs | % DC Exp |
|---|---|---|---|---|---|
| | Compound | Pyraclostrobin | Epoxiconazole | | |
| 1DP PUCCRT | | | | | |
| 15 | 0.3 | | | 33 | |
| pyraclostrobin alone | | 0.1 | | 8 | |
| epoxiconazole alone | | | 0.1 | 0 | |
| 15 + pyraclostrobin | 0.3 | 0.1 | | 73 | 39 |
| 15 + epoxiconazole | 0.3 | | 0.1 | 76 | 33 |
| 3DC PUCCRT | | | | | |
| 15 | 0.9 | | | 52 | |
| 15 | 0.3 | | | 6 | |
| pyraclostrobin alone | | 0.3 | | 4 | |
| epoxiconazole alone | | | 0.1 | 13 | |
| 15 + pyraclostrobin | 0.9 | 0.3 | | 83 | 54 |
| 15 + epoxiconazole | 0.3 | | 0.1 | 50 | 18 |

Animal Health Activity

The compounds of the present invention have been found to have significant potential as anti-parasitics for animal health. Table 4, shown below, presents the activity of typical compounds of the present invention when evaluated in these experiments. Activity has been demonstrated by four out of six compounds screened against *Caenorhabditis elegans*, a free-living nematode that is an indicator species for animal parasites. It will be understood by those in the art that the efficacy of four compounds against *Caenorhabditis elegans*, which at 10 μg/mL was equivalent to the commercial anti-parasitic product ivermectin, establishes the potential utility of these compounds to control parasites that attack animals.

The activity of the compounds against *Caenorhabditis elegans* was determined by dissolving compounds in DMSO, then applying them to petri dishes containing Nematode Growth Medium agar to a final concentration of 10 μg compound per milliliter agar. *Escherichia coli* bacteria were grown on the plates to provide a food source for the larvae of *Caenorhabditis elegans*. The bacteria were heat-killed at 65° C. before compounds were added to the plates.

The plates with compound and heat-killed bacteria were infested with 10 microliter drops containing eggs from wild-type *Caenorhabditis elegans* worms. Adult worms were dissolved in KOH and bleach and washed in Ringers solution to generate the egg suspension. Each compound was screened with approximately 400 eggs, divided between two petri dishes. Egg hatching was evaluated after 24 h at 20° C. Mortality was averaged over the two plates.

TABLE 4

Activity of compounds of the formula (I) against *Caenorhabditis elegans*.

| Compound | Percent mortality |
| --- | --- |
| 3 | 100 |
| 42 | 6 |
| 76 | 100 |
| 93 | 100 |
| 115 | 100 |
| 125 | 0 |
| Ivermectin | 95 |
| Untreated | <2 |

Application rate is 10 micrograms per milliliter agar.

Other Activity

The effect on mice of oral exposure was determined for compounds differing only in the number of fluorine substituents on the quinazoline ring, as shown in Table 5. Three CD-1/Swiss derived albino female mice were administered compounds by gavage as a 5% w/v mixture in 0.5% carboxymethylcellulose solution. The animals were monitored for 14 days.

TABLE 5

Effect of number of F substituents on quinazoline ring on mice. Compounds in bold are shown in TABLE 1.

| Compound | Number of F substituents on quinazoline ring | Mouse Oral $LD_{50}$ |
| --- | --- | --- |
|  | 1 | <100 mg/kg |
| 6 | 2 | 100-500 mg/kg |
| 31 | 3 | >500 mg/kg |

The effect of fluorine substitution was examined for additional compound sets using an insect as a model, as shown in Table 6. Colorado Potato Beetle (LPTNDE) sensitivity paralleled mouse sensitivity and showed that the relationship of fluorine substitution to animal sensitivity was general.

TABLE 6

Effect of number of F substituents on quinazoline ring on Colorado Potato Beetle.
Compounds in bold are shown in TABLE 1.

| Compound | Number of F substituents on quinazoline ring | Colorado Potato Beetle LC90 (ppm) |
|---|---|---|
| [structure: 8-F quinazoline-NH-CH₂CH₂-phenyl-O-pyridyl-CF₃ (4-CF₃)] | 1 | 31-12.5 |
| 6 | 2 | 12.5-50 |
| 31 | 3 | 50-200 |
| [structure: 8-F quinazoline-NH-CH₂CH₂-phenyl-O-pyridyl-CF₃ (5-CF₃)] | 1 | 0.12 |
| 1 | 2 | 0.49 |
| 74 | 3 | 1.0 |
| [structure: 8-F quinazoline-NH-CH₂CH₂-phenyl-O-pyridyl-CN] | 1 | <3.1 |
| 124 | 2 | 3.1-12.5 |

The invention claimed is:

1. A compound of formula (I)

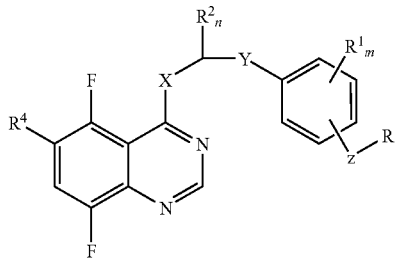

wherein:
R represents H, CH$_3$, or a heterocycle selected from the group consisting of pyridinyl, pyrazinyl, pyrimidinyl, and pyridazinyl wherein the heterocycle may be optionally substituted with one or more groups selected from halo, lower alkyl, lower alkenyl, lower alkynyl, lower alkoxy, haloalkyl, haloalkoxy, NO$_2$, CN, lower alkoxycarbonyl, and lower alkyl-SO$_q$, when q is an integer from 0 to 2;
Z represents a C—C single bond, CH$_2$, NH, O, S, —CH$_2$O—, or —OCH$_2$—;
m is 4;
R$^1$ are independently H, halo, lower alkyl, lower alkenyl, lower alkynyl, hydroxy, lower alkoxy, haloalkyl, haloalkoxy, NO$_2$, CN, lower alkoxycarbonyl, mercapto, or lower alkylthio;
Y is a C—C single bond, C(R$^7_n$)O or C(R$^7_n$);
n is 2;
R$^2$ are independently H or lower alkyl;
R$^7$ are independently H or lower alkyl;
X is NR$^3$ or O, where R$^3$ is selected from H, lower alkyl, lower alkyl-carbonyl, lower alkoxycarbonyl, hydroxy, lower alkoxy, lower alkyl-SO$_q$, phenyl-SO$_q$ or substituted phenyl-SO$_q$ when q is an integer from 0 to 2; and
R$^4$ is H or F;
with the proviso that when Y is C(R$^7_n$), R$^2_n$ and one of R$^1$ may be taken together to form a compound of formula (II)

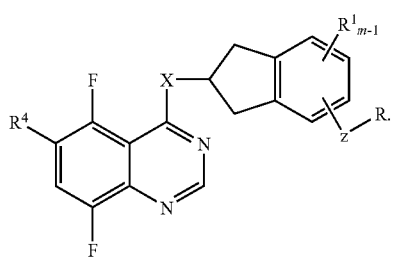

2. A composition comprising a compound according to claim 1 in the form of bait, concentrated emulsion, dust, emulsifiable concentrate, fumigant, gel, granule, microencapsulation, seed treatment, suspension concentrate, suspoemulsion, tablet, water soluble liquid, water dispersible granule, wettable powder, or ultra low volume solution.

* * * * *